United States Patent
Verheesen et al.

(10) Patent No.: US 12,403,175 B2
(45) Date of Patent: Sep. 2, 2025

(54) METHODS FOR TREATING PEMPHIGUS DISORDERS

(71) Applicant: argenx BV, Zwijnaarde (BE)

(72) Inventors: Peter Verheesen, Zwijnaarde (BE); Patrick Dupuy, Zwijnaarde (BE)

(73) Assignee: argenx BV, Zwijnaarde (BE)

( * ) Notice: Subject to any disclaimer, the term of this patent is extended or adjusted under 35 U.S.C. 154(b) by 569 days.

(21) Appl. No.: 17/144,481

(22) Filed: Jan. 8, 2021

(65) Prior Publication Data

US 2021/0236596 A1    Aug. 5, 2021

Related U.S. Application Data

(60) Provisional application No. 62/960,647, filed on Jan. 13, 2020, provisional application No. 62/958,543, filed on Jan. 8, 2020.

(51) Int. Cl.
*A61P 37/06* (2006.01)
*A61K 9/00* (2006.01)
*A61K 31/573* (2006.01)
*A61K 38/17* (2006.01)
*A61K 47/68* (2017.01)
*A61P 17/00* (2006.01)

(52) U.S. Cl.
CPC ........ *A61K 38/1709* (2013.01); *A61K 9/0019* (2013.01); *A61K 31/573* (2013.01); *A61K 47/6811* (2017.08); *A61P 17/00* (2018.01); *A61P 37/06* (2018.01)

(58) Field of Classification Search
CPC .............. A61K 38/1709; A61K 9/0019; A61K 31/573; A61K 47/6811; A61P 17/00; A61P 37/06
USPC ....................................................... 424/133.1
See application file for complete search history.

(56) References Cited

U.S. PATENT DOCUMENTS

| | | |
|---|---|---|
| 5,326,856 A | 7/1994 | Coughlin et al. |
| 5,624,821 A | 4/1997 | Winter et al. |
| 5,648,260 A | 7/1997 | Winter et al. |
| 5,677,425 A | 10/1997 | Bodmer et al. |
| 5,869,046 A | 2/1999 | Presta et al. |
| 5,885,573 A | 3/1999 | Bluestone et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,528,624 B1 | 3/2003 | Idusogie et al. |
| 6,737,056 B1 | 5/2004 | Presta et al. |
| 6,795,661 B2 | 9/2004 | Kanesawa et al. |
| 6,821,505 B2 | 11/2004 | Ward |
| 6,992,234 B2 | 1/2006 | Roopenian et al. |
| 7,083,784 B2 | 8/2006 | Dall'Acqua et al. |
| 7,183,387 B1 | 2/2007 | Presta |
| 7,670,600 B2 | 3/2010 | Dall'Acqua et al. |
| 7,683,784 B2 | 3/2010 | Nagai et al. |
| 7,704,497 B2 | 4/2010 | Dall'Acqua et al. |
| 8,012,476 B2 | 9/2011 | Dall'Acqua et al. |
| 8,021,856 B2 | 9/2011 | Umaña et al. |
| 8,067,232 B2 | 11/2011 | Kanda |
| 8,101,186 B2 | 1/2012 | Mezo et al. |
| 8,163,881 B2 | 4/2012 | Ober et al. |
| 8,195,661 B2 | 6/2012 | Asawaree |
| 8,216,805 B2 | 7/2012 | Carter et al. |
| 8,273,351 B2 | 9/2012 | Tenhoor et al. |
| 8,323,962 B2 | 12/2012 | Dall'Acqua et al. |
| 8,475,792 B2 | 7/2013 | Dall'Acqua et al. |
| 8,680,237 B2 | 3/2014 | Strome et al. |
| 8,795,661 B2 | 8/2014 | Dall'Acqua et al. |
| 8,815,246 B2 | 8/2014 | Tenhoor et al. |
| 8,834,871 B2 | 9/2014 | Ober |
| 9,260,520 B2 | 2/2016 | Tenhoor et al. |
| 10,316,073 B2 | 6/2019 | Ulrichts |
| 11,505,585 B2 * | 11/2022 | Ulrichts .................... A61P 7/06 |
| 11,591,388 B2 | 2/2023 | Borgions et al. |
| 12,202,900 B2 | 1/2025 | de Haard et al. |
| 12,240,875 B2 | 3/2025 | de Haard et al. |
| 2004/0002587 A1 | 1/2004 | Watkins et al. |
| 2004/0010124 A1 | 1/2004 | Johnson et al. |
| 2004/0047862 A1 | 3/2004 | Lazarus et al. |
| 2004/0265321 A1 | 12/2004 | Johnson et al. |
| 2005/0053598 A1 | 3/2005 | Burke et al. |
| 2006/0210557 A1 | 9/2006 | Luisi et al. |
| 2007/0041907 A1 | 2/2007 | Ober |
| 2007/0092507 A1 | 4/2007 | Balthasar et al. |
| 2009/0252729 A1 | 10/2009 | Farrington et al. |

(Continued)

FOREIGN PATENT DOCUMENTS

EP    0227110 A2    7/1987
EP    0904107 B1    3/1999

(Continued)

OTHER PUBLICATIONS

Soheil Tavakolpour (International Immunopharmacology, 2017, 53: 133-142).*

(Continued)

*Primary Examiner* — Yan Xiao

(74) *Attorney, Agent, or Firm* — Dechert LLP; Andrew T. Wilkins; Sharla F. Flohr

(57) ABSTRACT

Provided are methods for treating pemphigus using an FcRn antagonist such as efgartigimod. The methods of the invention provide a rapid onset of action to enable early disease control and maintenance of clinical remission, with or without a minimal dose of corticosteroids.

21 Claims, 20 Drawing Sheets

Specification includes a Sequence Listing.

(56) References Cited

U.S. PATENT DOCUMENTS

| | | |
|---|---|---|
| 2011/0066111 A1 | 3/2011 | Teschner et al. |
| 2011/0081345 A1 | 4/2011 | Moore |
| 2011/0243966 A1 | 10/2011 | Farrington et al. |
| 2012/0219551 A1 | 8/2012 | Johnson |
| 2013/0142802 A1 | 6/2013 | Chang et al. |
| 2013/0156765 A1 | 6/2013 | Block et al. |
| 2014/0302028 A1 | 10/2014 | Zha et al. |
| 2015/0218239 A1 | 8/2015 | Ulrichts et al. |
| 2016/0252497 A1 | 9/2016 | Ling |
| 2016/0264669 A1 | 9/2016 | Ulrichts et al. |
| 2017/0260238 A1 | 9/2017 | Abrahmsen et al. |
| 2019/0194277 A1 | 6/2019 | de Haard et al. |
| 2020/0024344 A1 | 1/2020 | de Haard et al. |
| 2022/0275035 A1 | 9/2022 | Ulrichts et al. |
| 2022/0298241 A1* | 9/2022 | Blumberg ............ C07K 16/283 |
| 2023/0357382 A1 | 11/2023 | Borgions et al. |
| 2024/0325528 A1 | 10/2024 | Van Bragt et al. |
| 2024/0369467 A1 | 11/2024 | Verheesen et al. |
| 2025/0051453 A1 | 2/2025 | Verheesen et al. |
| 2025/0084171 A1 | 3/2025 | van der Woning et al. |
| 2025/0101111 A1 | 3/2025 | Brinkhaus et al. |
| 2025/0122288 A1 | 4/2025 | Bobkov et al. |
| 2025/0122310 A1 | 4/2025 | Bobkov et al. |

FOREIGN PATENT DOCUMENTS

| | | |
|---|---|---|
| EP | 1355919 B1 | 11/2010 |
| EP | 1896503 B1 | 10/2014 |
| JP | 2013-507128 A | 3/2013 |
| WO | WO 1994/029351 A2 | 12/1994 |
| WO | WO 1996/022024 A1 | 7/1996 |
| WO | WO 1997/034631 A1 | 9/1997 |
| WO | 1998023289 A1 | 6/1998 |
| WO | WO 1999/004813 A1 | 2/1999 |
| WO | WO 1999/058572 A1 | 11/1999 |
| WO | WO 2000/042072 A2 | 7/2000 |
| WO | WO 2001/058957 A2 | 8/2001 |
| WO | WO 2002/043658 A2 | 6/2002 |
| WO | WO 2002/060919 A2 | 8/2002 |
| WO | WO 2004/016750 A2 | 2/2004 |
| WO | WO 2004/029207 A2 | 4/2004 |
| WO | WO 2004/035752 A1 | 4/2004 |
| WO | WO 2004/063343 A2 | 7/2004 |
| WO | WO 2004/063351 A2 | 7/2004 |
| WO | WO 2004/099249 A2 | 11/2004 |
| WO | WO 2005/040217 A2 | 5/2005 |
| WO | 2006028936 A2 | 3/2006 |
| WO | 2006122787 A1 | 11/2006 |
| WO | WO 2006/118772 A2 | 11/2006 |
| WO | WO 2006/130834 A2 | 12/2006 |
| WO | WO 2007/098420 A2 | 8/2007 |
| WO | WO 2009/100105 A2 | 8/2009 |
| WO | WO 2009/131702 A2 | 10/2009 |
| WO | WO 2010/014909 A1 | 2/2010 |
| WO | WO 2010/106180 A2 | 9/2010 |
| WO | WO2010111254 A1 | 9/2010 |
| WO | WO 2011/044368 A1 | 4/2011 |
| WO | 2011/080209 A2 | 7/2011 |
| WO | 2012160448 A2 | 11/2012 |
| WO | 2012175400 A1 | 12/2012 |
| WO | WO2012167039 A1 | 12/2012 |
| WO | WO 2013/000702 A1 | 1/2013 |
| WO | WO 2013/063186 A2 | 5/2013 |
| WO | WO 2013/074598 A1 | 5/2013 |
| WO | WO 2013/100702 A1 | 7/2013 |
| WO | 2013166604 A1 | 11/2013 |
| WO | 2013192504 A1 | 12/2013 |
| WO | WO 2014/008391 A1 | 1/2014 |
| WO | WO 2014/019727 A1 | 2/2014 |
| WO | WO2014140366 A1 | 9/2014 |
| WO | WO 2014/204280 A1 | 12/2014 |
| WO | 2015073721 A1 | 5/2015 |
| WO | WO2015071330 A1 | 5/2015 |
| WO | WO 2015/081073 A2 | 6/2015 |
| WO | WO 2015/100299 A1 | 7/2015 |
| WO | WO 2016/042083 A1 | 3/2016 |
| WO | WO 2016/123521 A2 | 8/2016 |
| WO | WO 2016/142782 A1 | 9/2016 |
| WO | WO 2016/180765 A1 | 11/2016 |
| WO | WO 2016/183352 A1 | 11/2016 |
| WO | WO 2017/012959 A1 | 1/2017 |
| WO | WO 2017/121330 A1 | 7/2017 |
| WO | 2017189959 A1 | 11/2017 |
| WO | WO2018023136 A1 | 2/2018 |
| WO | WO 2018/083122 A1 | 5/2018 |
| WO | 2018187057 A1 | 10/2018 |
| WO | WO 2019/110823 A1 | 6/2019 |
| WO | WO2019118791 A1 | 6/2019 |
| WO | WO 2019/234713 A2 | 12/2019 |
| WO | 2020/078905 A1 | 4/2020 |
| WO | WO2020097099 A1 | 5/2020 |
| WO | 2020208177 A1 | 10/2020 |
| WO | 2020227515 A1 | 11/2020 |
| WO | WO 2020/236695 A1 | 11/2020 |
| WO | WO2020245420 A1 | 12/2020 |
| WO | WO2021022249 A1 | 2/2021 |
| WO | WO2020245420 A9 | 4/2021 |
| WO | WO2021140202 A1 | 7/2021 |
| WO | 2021216756 A1 | 10/2021 |
| WO | WO2022098955 A1 | 5/2022 |
| WO | WO2023012515 A2 | 2/2023 |
| WO | WO2023135321 A1 | 7/2023 |
| WO | WO2023156614 A1 | 8/2023 |
| WO | WO2023209036 A1 | 11/2023 |
| WO | WO2023242361 A1 | 12/2023 |
| WO | WO2023242362 A1 | 12/2023 |
| WO | WO2023242371 A1 | 12/2023 |
| WO | WO2023242372 A1 | 12/2023 |
| WO | 2024052358 A1 | 3/2024 |
| WO | WO2024100453 A1 | 5/2024 |
| WO | WO2024100455 A1 | 5/2024 |
| WO | WO2024105445 A2 | 5/2024 |
| WO | WO2024147074 A1 | 7/2024 |
| WO | WO2024150073 A1 | 7/2024 |
| WO | 2024189430 A1 | 9/2024 |
| WO | 2025017368 A1 | 1/2025 |

OTHER PUBLICATIONS

"Auxiliary Request 1—Annotated Version" for European Patent No. 3087095 (Application No. 14827372.5), dated Oct. 28, 2020, 5 pages.

"Auxiliary Request 1—Clean Version" for European Patent No. 3087095 (Application No. 14827372.5), dated Oct. 28, 2020, 5 pages.

"Auxiliary Request 2—Annotated Version" for European Patent No. 3087095 (Application No. 14827372.5), dated Oct. 28, 2020, 5 pages.

"Auxiliary Request 2—Clean Version" for European Patent No. 3087095 (Application No. 14827372.5), dated Oct. 28, 2020, 4 pages.

"Cover Letter to the European Patent Office" for European Patent No. 3087095 (Application No. 14827372.5), dated Oct. 28, 2020, 1 page.

"Declaration of Pieter Spuijbroek" submitted with Reply to Notice of Opposition for European Patent No. 3087095 (Application No. 14827372.5), dated Oct. 28, 2020, 5 pages.

"Main Request—Annotated Version" for European Patent No. 3087095 (Application No. 14827372.5), dated Oct. 28, 2020, 5 pages.

"Main Request—Clean Version" for European Patent No. 3087095 (Application No. 14827372.5), dated Oct. 28, 2020, 5 pages.

"Online Filing Acknowledgement for Reply to Notice of Opposition" for European Patent No. 3087095 (Application No. 14827372.5), dated Oct. 28, 2020, 2 pages.

"Proof of Employment for Inventor/Applicant Sally Ward" submitted with Reply to Notice of Opposition for European Patent No. 3087095 (Application No. 14827372.5), dated Oct. 28, 2020, 1 page.

"Reply to Notice of Opposition" for European Patent No. 3087095 (Application No. 14827372.5), dated Oct. 28, 2020, 35 pages.

(56) References Cited

OTHER PUBLICATIONS

"Rule 90101 of the Rules and Regulations of the Board of Regents of the University of Texas System governing intellectual property" dated Feb. 27, 2012, submitted with Reply to Notice of Opposition for European Patent No. 3087095 (Application No. 14827372.5), on Oct. 28, 2020, 21 pages.

"UniProtKB—P01857 (IGHG1_Human)" submitted with Reply to Notice of Opposition for European Patent No. 3087095 (Application No. 14827372.5), dated Oct. 28, 2020, 6 pages.

Abdiche et al. (2015) "The neonatal Fc receptor (FcRn) binds independently to both sites of the IgG homodimer with identical affinity," mAbs, 7(2):331-343.

Akilesh et al. (2004) "The MHC class I-like Fc receptor promotes humorally mediated autoimmune disease," J. Clin. Invest. 113(9):1328-1333.

Alegre et al. (1994) "A Non-Activating "Humanized" Anti-CD3 Monoclonal Antibody Retains Immunosuppressive Properties In Vivo," Transplantation, 57(11):1537-1543.

Alipour-Faz et al. (2017) "A comparison between IVIG and plasma exchange as preparations before thymectomy in myasthenia gravis patients," Acta Neurol Belg, 117:245-249.

Andersen et al. (2012) "Structure-based mutagenesis reveals the albumin-binding site of the neonatal Fc receptor," Nat. Commun. 3:610. pp. 1-9.

Anonymous (2016) "argenx announces initial results from Phase 1 multiple ascending dose (MAD) study of ARGX-113 in healthy volunteers—Argenx," 1 pg.

ArGEN-X "ARGX-113," http://www.argen-x.com. Accessible on the Internet at URL: http://www.argen-x.com/en-GB/content/argx-113/22. [Last Accessed Jul. 5, 2017].

ArGEN-X (Oct. 2013) "An Emerging Antibody Force: Company Presentation," Presentation Slides.

ArGEN-X (Oct. 2013) "ARGX-113: Development Opportunity in Autoimmunity," Presentation Slides.

ArGEN-X N.V. (Apr. 24, 2014) "arGEN-X advances ARGX-113 into preclinical development for autoimmune disorders," Press Release. arGEN-X. Accessible on the Internet at URL: http://www.argen-x.com/en-GB/news-internal/argen-x-advances-argx-113-into-preclinical-devlopment-for-autoimmune-disorders/60. [Last Accessed Aug. 1, 2016].

ArGEN-X N.V. (Aug. 19, 2014) "arGEN-X announces positive preclinical results for ARGX-113," Press Release. Euronext. Accessible on the Internet at URL: https://www.euronext.com/nl/node/506652. [Last Accessed Aug. 1, 2016].

ArGEN-X N.V. (Jun. 20, 2014) Prospectus for Public Offering of arGEN-X N.V.

Armour et al. (1999) "Recombinant human IgG molecules lacking Fcgamma receptor I binding and monocyte triggering activities," Eur. J. Immunol. 29:2613-2624.

Balighi et al., "Comparing early and late treatments with rituximab in pemphigus vulgaris: which one is better?", Archives of Dermatological Research, Dec. 1, 2018, 311(1): 63-69.

Ballow (1991) "Mechanism of action of IVIG therapy and potential uses in autoimmune connective tissue diseases," Cancer 68:1430-1436.

Barth et al. (2011) "Comparison of IVIg and PLEX in patients with myasthenia gravis," Neurology. 76(23):2017-2023.

Blanchette et al. (1984) "Intensive plasma exchange therapy in ten patients with idiopathic thrombocytopenia purpura," Transfusion. 24(5):388-394.

Burns (2012) "Of Mice and Children: Lessons From a Kawasaki Mouse Model," Circulation. 125:1480-1481.

Burns et al. (2010) "History of outcome measures for myasthenia gravis," Muscle Nerve. 42(1):5-13.

Bussel et al., "Long-term use of the thrombopoietin-mimetic romiplostim in children with severe chronic immune thrombocytopenia (ITP): Romiplostim in Pediatric ITP" Pediatric Blood and Cancer, Feb. 1, 2015, vol. 62, No. 2, pp. 208-213.

Bussel et al., "A Randomized, Double-Blind Study of Romiplostim to Determine its Safety and Efficacy in Children with Immune Thrombocytopenia", Blood, vol. 118, No. 1, Jul. 7, 2011, pp. 28-36.

Challa (2013) "Autoantibody depletion ameliorates disease in murine experimental autoimmune encephalomyelitis," mAbs, 5(5):655-659.

Chaudhury et al. (2003) "The major histocompatibility complex-related Fc receptor for IgG (FcRn) binds albumin and prolongs its lifespan," J. Exp. Med. 197(3):315-322.

Cipriani et al. (2009) "MET as a target for treatment of chest tumor," Lung Cancer. 63(2):169-179.

Clarkson et al. (1986) "Treatment of Refractory Immune Thrombocytopeni Purpura with an Anti-Fcgamma-Receptor Antibody," New England Journal of Medicine. 314(9):1236-1239.

ClinicalTrials.gov, "A Study to Evaluate the Safety, Efficacy, and Pharmacokinetics of ARGX-113 in Patients with ITP", ClinicalTrials.gov Identifier NCT03102593, Apr. 6, 2017, 7 pages.

ClinicalTrials.gov, "A Study to Evaluate the Safety, PD, PK and Efficacy of ARGX-113 in Patients with Pemphigus", ClinicalTrials.gov Identifier NCT03334058, Nov. 7, 2017, 8 pages.

ClinicalTrials.gov, "A Study to Evaluate the Safety, PD, PK and Efficacy of ARGX-113 in Patients with Pemphigus", ClinicalTrials.gov Identifier NCT04598477, Oct. 22, 2020, 10 pages.

Coetzee et al. (2000) "The Effect of Monoclonal Anti-human-platelet Antibodies on Platelet Kinetics in a Baboon Model: IgG Subclass Dependency," Thromb. Haemost. 83:148-156.

Combined Search and Examination Report for Great Britain Application No. GB1617270.2, mailed Aug. 3, 2017, 6 pages.

Crow et al. (2008) "The Mechanisms of Action of Intravenous Immunoglobulin and Polyclonal Anti-D Immunoglobulin in the Amelioration of Immune Thrombocytopeni Purpura: What Do We Really Know?" Transfusion Medicine Reviews. 22:103-116.

Crow et al. (2011) "The neonatal Fc receptor (FcRn) is not required for IVIg or anti-CD44 monoclonal antibody-mediated amelioration of murine immune thrombocytopenia," Blood. 118:6403-6406.

Darabi et al. (2006) "Current usage of intravenous immune globulin and the rationale behind it: the Massachusetts General Hospital data and a review of the literature," Transfusion. 46(5):741-753.

Daugherty et al., "Formulation and delivery issues for monoclonal antibody therapeutics", Adv Drug Deliv Rev., Aug. 7, 2006, 58(5-6): 686-706.

De Haard et al., "Advancing ARGX-113 and ARGX-110 to Clinical Proof of Concept", Dec. 4, 2016, pp. 1-575.

Debre et al. (1993) "Infusion of Fc gamma fragments for treatment of children with acute immune thrombocytopenia purpura," Lancet. 342(8877):945-949.

Deng et al. (2007) "Pharmacokinetic/pharmacodynamic modeling of IVIG effects in a murine model of immune thrombocytopenia," J. Pharm. Sci. 96(6):1625-1637.

Dick Jr. et al., "C-Terminal Lysine Variants in Fully Human Monoclonal Antibodies: Investigation of Test Methods and Possible Causes", Biotechnology and Bioengineering, 2008, vol. 100, No. 6, pp. 1132-1143.

Duncan et al. (1988) "Localization of the binding site for the human high-affinity Fc receptor on IgG," Nature, 332:563-564.

Eddleston et al., "Blockade of the Neonatal Fc Receptor (FcRn) Represents an Effective Mechanism for the Removal of Pathogenic Autoantibodies in Primary Immune Thrombocytopenia", Database Biosis [Online] Biosciences Information Service, Philadelphia, PA, Dec. 7, 2017, XP002794883, Database accession No. PREV201900186122 abstract & Blood, vol. 130, No. Suppl. 1, p. 230.

Edelman et al. (1969) "The covalent structure of an entire gammaG immunoglobulin molecule," The Journal of Immunology, 63:5335-5342.

El-Salem et al. (2014) "Treatment of MuSK-Associated Myasthenia Gravis," Curr. Treat. Options Neurol., 16:283, 17 pages.

Eymard et al. (2009) "[Antibodies in myasthenia gravis]," Rev. Neurol. (Paris). 165(2):137-143.

Federico et al. (2000) "Multifocal motor neuropathy improved by IVIg: randomized, double-blind, placebo-controlled study," Neurology. 55:1256-1262.

(56) References Cited

OTHER PUBLICATIONS

Flaherty et al. (Oct. 24, 2011) "Nonclinical evaluation of GMA161—an antihuman CD16 (Form) monoclonal antibody for treatment of autoimmune disorders in CD16 transgenic mice," Toxicological Sciences. 125(1):299-309.
Frusho et al. (1984) "High-dose intravenous gammaglobulin for Kawasaki disease," Lancet. 2:1055-1058.
Gan et al. (2009) "Analyses of the recycling receptor, FcRn, in live cells reveal novel pathways for lysosomal delivery," Traffic. 10:600-614.
Garcia et al. (2001) "Kinetics and thermodynamics of T cell receptor-autoantigen interactions in murine experimental autoimmune encephalomyelitis," Proc. Natl. Acad. Sci. USA. 98:6818-6823.
Genbank Database [online] (Jul. 2, 2016) "*Homo sapiens* Fc fragment of IgG receptor IIIa (FCGR3A), transcript variant 1, mRNA," Accession No. NM_000569. Accessible on the Internet at URL: http://www.ncbi.nlm.nih.gov/nuccore/NM_000569. [Last Accessed Aug. 19, 2016].
Ghetie et al. (1996) "Abnormally short serum half lives of IgGs in beta2-microglobulin deficient mice," Eur. J. Immunol. 26:690-696.
Ghetie et al. (1997) "Increasing the serum persistence of an IgG fragment by random mutagenesis," Nature Biotech. 15:637-640.
Ghetie et al. (2002) "Transcytosis and catabolismof antibody," Immunol. Res. 25(2):97-113.
Gilhus et al. (2011) "Myasthenia Gravis: A Review of Available Treatment Approaches," Autoimmune Diseases, Article ID 847393, 6 pages.
Grau (Sep. 21, 2011) "IgG core a-fucosylation and its impact on FcγRIIIa binding," Roche Glycart AG. In; MipTec 2011, Basel, Switzerland.
Grevys et al. (Apr. 22, 2015) "Fc Engineering of Human IgG1 for Altered Binding to the Neonatal Fc Receptor Affects Fc Effector Functions," J Immunol. 194(11):5497-5508.
Guptill et al. (Aug. 11, 2016) "Effect of therapeutic plasma exchange on immunoglobulins in myasthenia gravis," Autoimmunity. 49(7):472-479.
Hansen et al. (2002) "Intravenous Immunoglobulin Mediates an Increase in Anti-Platelet Antibody Clearance via the FcRn Receptor," Thromb. Haemost. 88:898-899.
Hanson (2014) "The role of the immunoglobulin G1 Fc N-glycan in FcγRIIIa affinity," Thesis for partial fulfillment of the degree of Master of Science. Iowa State University. Paper 14135.
Howard et al. (Apr. 30, 2013) "A randomized, double-blind, placebo-controlled phase II study of eculizumab in patients with refractory generalized myasthenia gravis," Muscle Nerve. 48(1):76-84.
Howard et al., "Randomized phase 2 study of FcRn antagonist efgartigimod in generalized myasthenia gravis", Neurology, 2019, vol. 92, No. 23, pp. 1-8.
Huang et al. (2005) "The central residues of a T cell receptor sequence motif are key determinants of autoantigen recognition in murine experimental autoimmune encephalomyelitis," Eur. J. Immunol. 35:299-304.
Hutchins et al. (1995) "Improved biodistribution, tumor targeting, and reduced immunogenicity in mice with a gamma4 variant of Campath-1H," Proc. Natl. Acad. Sci., USA, 92:11980-11984.
Idusogie et al. (2000) "Mapping of the C1q Binding Site on Rituxan, a Chimeric Antibody with a Human IgG1 Fc," J. Immunol., 164:4178-4184.
Idusogie et al. (2001) "Engineered Antibodies with Increased Activity to Recruit Complement," J. Immunol., 166:2571-2575.
Imbach et al. (1981) "High-dose intravenous gammaglobulin for idiopathic thrombocytopenia purpura in childhood," The Lancet, 1228-1231.
Imbach et al. (1985) "Intravenous immunoglobulin versus oral corticosteroids in acute immune thrombocytopeniarpura in childhood," The Lancet, 464-468.
Imbach et al. (2009) "Intravenous immunoglobulins induce potentially synergistic immunomodulations in autoimmune disorders," Vox Sanguinis, 10 pages.
Imbach, Paul (2012) "Treatment of immune thrombocytopenia with intravenous immunoglobulin and insights for other diseases," Swiss Medical Weekly, 10 pages.
International Preliminary Report on Patentability for PCT International Patent Application No. PCT/EP2013/068399, issued Mar. 10, 2015.
International Preliminary Report on Patentability for PCT International Patent Application No. PCT/US2014/072087, issued Jun. 28, 2016.
International Preliminary Report on Patentability for PCT International Patent Application No. PCT/IB2019/054786, mailed Dec. 8, 2020.
International Preliminary Report on Patentability for PCT International Patent Application No. PCT/IB2016/000398, mailed Sep. 12, 2017.
International Search Report and Written Opinion for PCT International Patent Application PCT/EP2017/077966, mailed Jan. 29, 2018.
International Search Report and Written Opinion for PCT International Application No. PCT/IB2019/054786, mailed Dec. 18, 2109 (27 pages).
International Search Report and Written Opinion for PCT International Patent Application No. PCT/EP2013/068399, mailed Apr. 9, 2014.
International Search Report with Written Opinion for PCT International Patent Application No. PCT/US2014/072087, mailed May 12, 2015.
International Search Report with Written Opinion for PCT International Patent Application No. PCT/EP2018/084034, mailed Feb. 18, 2019.
International Search Report with Written Opinion for PCT International Patent Application No. PCT/IB2016/000398, mailed Aug. 22, 2016.
International Search Report with Written Opinion for PCT International Patent Application No. PCT/EP2020/065716, mailed Sep. 14, 2020.
International Search Report with Written Opinion for PCT International Patent Application No. PCT/EP2021/050275, mailed Apr. 8, 2021.
Jacob et al. (2012) "Presence and Pathogenic Relevance of Antibodies to Clustered Acetylcholine Receptor in Ocular and Generalized Myasthenia Gravis," Arch Neurol., 69(8):994-1001.
Jain et al. (Aug. 20, 2012) "Fully recombinant IgG2a Fc multimers (stradomers) effectively treat collagen-induced arthritis and prevent idiopathic thrombocytopeni purpura in mice," Arthritis Research & Therapy 14:R192. pp. 1-12.
Jefferis et al. (1995) "Recognition sites on human IgG for Fcgamma receptors: the role of glycosylation," Immunology Letters, 44:111-117.
Jefferis et al. (1996) "Modulation of Fc(gamma)R and human complement activation by IgG3-core oligosaccharide interactions," Immunol. Lett. 54:101-104.
Jefferis et al. (2002) "Interaction sites on human IgG-Fc for FcgammaR: current models," Immunology Letters, 82:57-65.
Junghans (1997) "Finally! The Brambell receptor (FcRB). Mediator of transmission of immunity and protection from catabolismfor IgG," Immunologic Research. 16(1):29-57.
Junghans et al. (1996) "The protection receptor for IgG catabolismis the beta2-microglobulin-containing neonatal intestinal transport receptor," Proc. Natl. Acad. Sci. USA. 93:5512-5516.
Kabat et al., "Unusual Distributions of amino Acids in Complementarity-determining (Hypervariable) Segments of Heavy and Light Chains of Immunoglobulins and Their Possible Roles in Specificity of Antibody-combining Sites", The Journal of Biological Chemistry, Oct. 1, 1977, 252(19): 6609-6616.
Kanda et al. (2006) "Comparison of biological activity among nonfucosylated therapeutic IgG1 antibodies with three different N-linked Fc oligosaccharides: the high-mannose, hybrid, and complex types," Glycobiol. 17(1):104-118.
Kang et al., "Rapid Formulation Development for Monoclonal Antibodies", BioProcess International, Apr. 12, 2016, retrieved from url: https://bioprocessintl.com/manufacturing/formulation/rapid-formulation-development-for-monoclonal-antibodies/.

(56) References Cited

OTHER PUBLICATIONS

Kim et al. (1999) "Mapping of the site on human IgG1 for binding of the MHC class I related receptor, FcRn," Eur. J. Immunol. 29:2819-2825.
Law et al. (1997) "High-dose intravenous immune globulin and the response to splenectomy in patients with idiopathic thrombocytopenia purpura," N. Engl. J. Med. 336:1494-1498.
Li et al. (2005) "Complete FcRn dependence for intravenous Ig therapy in autoimmune skin blistering diseases," J. Clin. Invest. 115(12):3440-3450.
Liu et al. (2007) "Amelioration of experimental autoimmune myasthenia gravis in rats by neonatal FcR blockade," J. Immunol. 178(8):5390-5398.
Liu et al. (2009) "Comparing the Autoantibody Levels and Clinical Efficacy of Double Filtration Plasmapheresis, Immunoadsorption, and Intravenous Immunoglobulin for the Treatment of Late-Onset Myasthenia Gravis," Therapeutic Apheresis and Dialysis, 14(2):153-160.
Low et al. (2009) "Inhibitors of the FcRn:IgG Protein-Protein Interaction," AAPS Journal. 11(3):432-434.
Lund et al. (1991) "Human Fc gamma RI and Fc gamma RII interact with distinct but overlapping sites on human IgG," J. Immunol. 147:2657-2662.
Lund et al. (1992) "Multiple binding sites on the CH2 Domain of IgG for Mouse FcgammaRII," Molecular Immunology, 29(1):53-59.
Lund et al. (1995) "Oligosaccharide-protein interactions in IgG can modulate recognition by Fcgamma receptors," The FASEB Journal 9:115-119.
Lund et al. (1996) "Multiple interactions of IgG with its core oligosaccharide can modulate recognition by complement and human Fc gamma receptor I and influence the synthesis of its oligosaccharide chains," J. Immunol. 157:4963-4969.
Lutterbach et al. (2007) "Lung cancer cell lines harboring MET gene amplification are dependent on Met for growth and survival," Cancer Research. 67(5):2081-2088.
MacCallum et al. (1996) "Antibody-antigen Interactions: Contact Analysis and Binding Site Topography," J. Mol. Biol., 262:732-745.
Martin et al. (2001) "Crystal Structure at 2.8 A of an FcRn/Heterodimeric Fc Complex Mechanism of pH-Dependent Binding," Molecular Cell, 7:867-877.
Massachusetts General Hospital (Dec. 10, 2012) "Suppremol's Sm101 shows a sustained clinical activity and a favorable safety profile in primary immune thrombocytopenia (ITP) patients," Press Release. Evaluate Ltd.
Medesan et al. (1997) "Delineation of the amino acid residues involved in transcytosis and catabolism of mouse IgG," J. Immunol. 158:2211-2217.
Mendell et al. (2001) "Randomized controlled trial of IVIg in untreated chronic inflammatory demyelinating polyradiculoneuropathy," Neurology. 56:445-449.
Meriggioli et al. (2009) "Autoimmune myasthenia gravis: emerging clinical and biological heterogeneity," Lancet Neurol. 8:475-490.
Mezo et al. (2008) "Reduction of IgG in nonhuman primates by a peptide antagonist of the neonatal Fc receptor FcRn," Proc. Natl. Acad. Sci. USA. 105(7):2337-2342.
Mi et al. (2008) "Targeting the neonatal Fc receptor for antigen delivery using engineered Fc fragments," J. Immunol. 181:7550-7561.
Mohamed et al. (Jan. 7, 2013) "Massive intravascular haemolysis after high dose intravenous immunoglobulin therapy," British Journal of Haematology. 160:570.
Montoyo et al. (2009) "Conditional deletion of the MHC class I-related receptor FcRn reveals the sites of IgG homeostasis in mice," Proc. Natl. Acad. Sci. USA. 106:2788-2793.
Morea et al. (2000) "Antibody Modeling: Implications for Engineering and Design," Methods, 20:267-279.
Newburger et al. (2004) "Diagnosis, Treatment, and Long-Term Management of Kawasaki Disease: A Statement for Health Professionals From the Committee on Rheumatic Fever, Endocarditis, and Kawasaki Disease, Council on Cardiovascular Disease in the Young, American Heart Association," Pediatrics. 114:1708-1733.
Newland et al. (1983) "High-dose intravenous IgG in adults with autoimmune thrombocytopenia," The Lancet, 84-87.
Nieswandt et al. (1999) "Acute systemic reaction and lung alterations induced by an antiplatelet integrin gpIIb/IIIa antibody in mice," Blood. 94:684-693.
Niknami et al. (Jun. 2013) "Beneficial effect of a multimerized immunoglobulin Fc in an animal model of inflammatory neuropathy (experimental autoimmune neuritis)," J. Peripher. Nerv. Syst. 18(2):141-52.
Ober et al. (2004) "Exocytosis of IgG as mediated by the receptor, FcRn: an analysis at the single-molecule level," Proc. Natl. Acad. Sci. USA. 101:11076-11081.
Ober et al. (2004) "Visualizing the site and dynamics of IgG salvage by the MHC Class I-related receptor, FcRn," J. Immunol. 172:2021-2029.
Oshima et al. (1998) "Characterization of murine CD70 by molecular cloning and mAb," Int. Immunol. 10(4):517-526.
Patel et al. (2011) "Neonatal Fc receptor blockade by Fc engineering ameliorates arthritis in a murine model," J. Immunol. 187(2):1015-1022.
Pevzner et al. (2011) "Anti-LRP4 autoantibodies in AChR-and MuSK-antibody-negative myasthenia gravis," J. Neurol., 9 pages.
Prabhat et al. (2007) "Elucidation of intracellular recycling pathways leading to exocytosis of the Fc receptor, FcRn, by using multifocal plane microscopy," Proc. Natl. Acad. Sci. USA. 104:5889-5894.
Presta et al. (2002) "Engineering therapeutic antibodies for improved function," Biochemical Society Transactions, 30(4):487-490.
Reddy et al. (2000) "Elimination of Fc Receptor-Dependent Effector Functions of a Modified IgG4 Monoclonal Antibody to Human CD4," J. Immunol., 164:1925-1933.
Robak et al., "Phase II, Multiple-Dose Study of Anti-FcRn Antibody, Rozanolixizumab (UCB7665), in Patients with Primary Immune Thrombocytopenia: Interim Analysis", Blood, Dec. 7, 2017, 130(Suppl. 1): 15, 59$^{th}$ Annual Meeting of the American-Society-of-Hematology, Dec. 9-12, 2017.
Roopenian et al. (2003) "The MHC class I-like IgG receptor controls perinatal IgG transport, IgG homeostasis, and fate of IgG-Fc-coupled drugs," J. Immunology. 170:3528-3533.
Roopenian et al. (2007) "FcRn: the neonatal Fc receptor comes of age," Nat. Rev. Immunol. 7(9):715-725.
Roux et al. (1998) "Comparisons of the Ability of Human IIgG3 Hinge Mutants, IgM, IgE, and IgA2, to Form Small Immune Complexes: A Role for Flexibility and Geometry," The Journal of Immunology, 4083-4090.
Schwab et al. (Mar. 2013) "Intravenous immunoglobulin therapy: how does IgG modulate the immune system?" Nat. Rev. Immunol. 176(13).
Seidling et al. (2013) "Analysis of high-dose intravenous immunoglobulin therapy in 16 patients with refractory autoimmune blistering skin disease: high efficacy and no serious adverse events," Acta Derm Venereol. 93:346-349.
Semple (2010) "Animal models of immune thrombocytopenia (ITP)," Annals of Hematology. 89:37-44.
Sesarman et al. (2010) "The neonatal Fc receptor as therapeutic target in IgG-mediated autoimmune diseases," Cell. Mol. Life Sci. 67(15):2533-2550.
Sewell: Ed. (Jan. 22, 2010) First National Immunoglobulin Database Report. Department of Health.
Shang et al., "Modular protein expression by RNA trans-splicing enables flexible expression of antibody formats in mammalian cells from a dual-host phage display vector", Protein Engineering, Design & Selection, 2015, vol. 28, No. 10, pp. 437-444.
Shelton (1999) "Acquired myasthenia gravis: what we have learned from experimental and spontaneous animal models," Veterinary Immunology and Immunopathology. 69:239-249.
Shields et al. (2001) "High Resolution Mapping of the Binding Site on Human IgG1 for FcgammaRI, FcgammaRII, FcgammaRIII, and FcRn and Design of IgG1 Variants with Improved Binding to the FcgammaR," The Journal of Biological Chemistry, 276(9):6591-6604.

(56) References Cited

OTHER PUBLICATIONS

Sockolosky et al. (2015) "The neonatal Fc receptor, FcRn, as a target for drug delivery and therapy," Advanced Drug Delivery Reviews, 91:109-124.
Soliven (2012) "Autoimmune neuropathies: insights from animal models," Journal of the Peripheral Nervous System. 17:28-33.
Sorde et al. (2017) "Massive immune response against IVIg interferes with response against other antigens in mice: A new mode of action?," PLoS One, 12(10):e0186046, 15 pages.
Stamos et al. (2004) "Crystal structure of the HGF beta-chain in complex with the Sema domain of the Met receptor," EMBO J. 23(12):2325-2335.
Swiercz et al. (May 27, 2014) "Use of Fc-engineered antibodies as clearing agents to increase contrast during PET," J. Nucl. Med. 55:1204-1207.
Swiss Webster Mice, by Taconic, Aug. 23, 2018, pp. 1-7.
Task Force of the Medical Scientific Advisory Board of the Myasthenia Gravis Foundation of America, et al. (2000) "Myasthenia gravis," Neurology, 55:16-23.
Tramontano et al. (1990) "Framework Residue 71 is a Major Determinant of the Position and Conformation of the Second Hypervariable Region in the VH Domains of Immunoglobulins," J. Mol. Biol., 215:175-182.
Ulrichts et al. (2018) "Neonatal Fc receptor antagonist efgartigimod safely and sustainably reduces IgGs in humans," J. Clin. Invest., 16 pages.
Ulrichts et al. (May 2017) "ARGX-113: Towards a Safe and Selective Elimination of Pathogenic Autoantibodies," 13th International Conference on Myasthenia Gravis and Related Disorders, May 15-17, 2017. New York, New York. Poster Presentation.
Ulrichts et al., "ARGX -113, a Novel Fc-Based Approach for Antibody-Induced Pathologies Such as Primary Immune Thrombocytopenia", Blood, vol. 128, No. 22, Dec. 2016, p. 4919, 58th annual Meeting and Exposition of the American-Society-of-Hematology; San Diego, CA, Dec. 3-6, 2016.
Vaccaro et al. (2005) "Engineering the Fc region of immunoglobulin G to modulate in vivo antibody levels," Nat. Biotechnol. 23(10):1283-1288.
Vaccaro et al. (2006) "Divergent activities of an engineered antibody in murine and human systems have implications for therapeutic antibodies" Proc. Natl. Acad. Sci. USA. 103(49):18709-18714.
Van Der Meche et al. (1992) "A randomized trial comparing intravenous immune globulin and plasma exchange in Guillain-Barre syndrome. Dutch Guillain-Barre Study Group," N. Engl. J. Med. 326:1123-1129.
Wang et al., "Protein aggregation and its inhibition on biopharmaceutics", International Journal of Pharmaceutics, Jan. 31, 2005, 289(1-2): 1-30.
Wani et al. (2006) "Familial hypercatabolic hypoproteinemia caused by deficiency of the neonatal Fc receptor, FcRn, due to a mutant beta2-microglobulin gene," Proc. Natl. Acad. Sci. USA. 103(13):5084-5989.
Woods et al. (1984) "Autoantibodies against platelet glycoprotein Ib in patients with chronic immune thrombocytopenia purpura," Blood. 64:156-160.
Xu et al. (2000) "In Vitro Characterization of Five Humanized OKT3 Effector Function Variant Antibodies," Cellular Immunology, 200:16-26.
Yang et al., (2011) "Non-radioactive serological diagnosis of myasthenia gravis and clinical features of patients from Tianjin, China," Journal of Neurological Sciences, 301:71-76, 2011.
Ying et al. (2012) "Soluble Monomeric IgG1 Fc," The Journal of Biological Chemistry, 287(23):19399-19408.
Ying et al. (2013) "Engineered Soluble Monomeric IgG1 CH3 Domain," The Journal of Biological Chemistry, 288 (35):25154-25164.
Zhang et al. (2012) "Autoantibodies to Lipoprotein-Related Protein in Patients With Double-Seronegative Myasthenia Gravis," Arch Neurol, 69(4):445-451.
Zhou et al. (2003) "Generation of mutated variants of the human form of the MHC class I-related receptor, FcRn, with increased affinity for mouse immunoglobulin G," J. Mol. Biol. 332:901-913.
Zhou et al. (2005) "Conferring the binding properties of the mouse MHC Class I related receptor, FcRn, onto the human ortholog by sequential rounds of site-directed mutagenesis," J. Mol. Biol. 345:1071-1081.
Zinman et al. (2007) "IV immunoglobulin in patients with myasthenia gravis: a randomized controlled trial," Neurology 68:837-841.
Bussel et al., "Eltrombopag for the Treatment of Chronic Idiopathic Thrombocytopenia Purpura", NEJM, 2007, 357(22): 2237-2247.
International Preliminary Report on Patentability for PCT International Patent Application No. PCT/EP2020/065716, mailed Dec. 7, 2021.
Janeway et al., (2005) Immunobiology, Part II. The Recognition of Antigen, Chapter 5.
Khan et al., "Clinical Practice Updates in the Management of Immune Thrombocytopenia", P&T, Dec. 2017, 42(12): 756-763.
Newland et al., "Phase 2 study of efgartigimod, a novel FcRn antagonisr, in adult patients with primary immune thrombocytopenia", Am Journ Hematol., 2020, 95: 178-187.
Robak et al., "Single-Agent Ibrutinib Vs Chemoimmunotherapy Regimens for Treatment-Naïve Patients with Chronic Lymphocytic Leukemia (CLL): A Cross-Trial Comparison", Blood, 2017, 130 (Suppl. 1): 1750.
Robak et al., "Efficacy and Safety of a new intravenous immunoglobulin 10% formulation (octagam® 10%) in patients with immune throbmbocytopenia", Hematology, 2010, 15(5): 351-359.
"Anthony et al., Apr. 18, 2008, Science, 320(5874): 373-376", Document D14 submitted with Notice of Opposition for European Patent No. 3087095 (Application No. 14827372.5), dated May 7, 2020.
"ArGEN-X advances ARGX-113 into preclinical development for autoimmune disorders, Apr. 24, 2014", Document D38 submitted with Notice of Opposition for European Patent No. 3087095 (Application No. 14827372.5), dated May 7, 2020.
"ArGEN-X Announces Positive Preclinical Results for ARGX-113, Aug. 19, 2014", Document D39 submitted with Notice of Opposition for European Patent No. 3087095 (Application No. 14827372.5), dated May 7, 2020.
"Assignment submission for U.S. Appl. No. 61/920,547 confirming change of legal form of arGEN-X B.V. to arGEN-X N.V. on May 28, 2014", Document D30 submitted with Notice of Opposition for European Patent No. 3087095 (Application No. 14827372.5), dated May 7, 2020.
"Blumberg & Lencer, Oct. 2005, Nat Biotechnol., 23(10): 1232-1234", Document D03 submitted with Notice of Opposition for European Patent No. 3087095 (Application No. 14827372.5), dated May 7, 2020.
"Bruhns et al., Apr. 2003, Immunity, 18(4): 573-571", Document D16 submitted with Notice of Opposition for European Patent No. 3087095 (Application No. 14827372.5), dated May 7, 2020.
"Brych et al., Feb. 2010, J Pharm Sci., 99(2): 764-781", Document D37 submitted with Notice of Opposition for European Patent No. 3087095 (Application No. 14827372.5), dated May 7, 2020.
"Carter, May 2006, Nat Rev immunol., 6(5): 343-357", Document D22 submitted with Notice of Opposition for European Patent No. 3087095 (Application No. 14827372.5), dated May 7, 2020.
"Challa et al., Sep.-Oct. 2013, MAbs, 5(5): 655-659", Document D10 submitted with Notice of Opposition for European Patent No. 3087095 (Application No. 14827372.5), dated May 7, 2020.
"Corrected Filing Receipt for U.S. Appl. No. 61/920,547 dated Apr. 16, 2015", Document D27 submitted with Notice of Opposition for European Patent No. 3087095 (Application No. 14827372.5), dated May 7, 2020.
"Dall'Acqua et al., Nov. 1, 2002, J Immunol., 169(9): 5171-5180", Document D21 submitted with Notice of Opposition for European Patent No. 3087095 (Application No. 14827372.5), dated May 7, 2020.
"Debre et al., Oct. 16, 1993, Lancet, 342: 945-949", Document D12 submitted with Notice of Opposition for European Patent No. 3087095 (Application No. 14827372.5), dated May 7, 2020.

(56) References Cited

OTHER PUBLICATIONS

"Dimitrov, Jan.-Feb. 2009, MAbs, 1(1): 26-28", Document D20 submitted with Notice of Opposition for European Patent No. 3087095 (Application No. 14827372.5), dated May 7, 2020.
"EP 1896503 Amended Claims and Response submitted Feb. 23, 2014 during prosecution of the application which led to grant of D1", Document D02a submitted with Notice of Opposition for European Patent No. 3087095 (Application No. 14827372.5), dated May 7, 2020.
"EP 1896503 B1 dated Oct. 29, 2014", Document D01 submitted with Reply to Notice of Opposition for European Patent No. 3087095 (Application No. 14827372.5), dated May 7, 2020.
"EP 3087095 B1 dated Aug. 7, 2019" submitted with Notice of Opposition for European Patent No. 3087095 (Application No. 14827372.5), dated May 7, 2020.
"Filing Receipt for U.S. Appl. No. 61/920,547 dated Jan. 21, 2014", Document D25 submitted with Notice of Opposition for European Patent No. 3087095 (Application No. 14827372.5), dated May 7, 2020.
"Gan et al., May 2009, Traffic, 10(5): 600-614", Document D08 submitted with Notice of Opposition for European Patent No. 3087095 (Application No. 14827372.5), dated May 7, 2020.
"Goh and Ng, Sep. 2018, Crit Rev Biotechnol., 38(6): 851-867", Document D19 submitted with Notice of Opposition for European Patent No. 3087095 (Application No. 14827372.5), dated May 7, 2020.
"Gómez-Guerrero et al., Feb. 15, 2000, J Immunol., 164(4): 2092-2101", Document D15 submitted with Notice of Opposition for European Patent No. 3087095 (Application No. 14827372.5), dated May 7, 2020.
"Inventor Assignment of U.S. Appl. No. 61/920,547 to arGEN-X B.V. executed Oct. 31, 2014 and Nov. 4, 2014", Document D29 submitted with Notice of Opposition for European Patent No. 3087095 (Application No. 14827372.5), dated May 7, 2020.
"Inventor Assignment of U.S. Appl. No. 61/920,547 to The Board of Regents of the University of Texas System executed Dec. 23, 2014", Document D28 submitted with Notice of Opposition for European Patent No. 3087095 (Application No. 14827372.5), dated May 7, 2020.
"Jefferis and Lefranc, Jul.-Aug. 2009, MAbs, 1(4): 332-338", Document D35 submitted with Notice of Opposition for European Patent No. 3087095 (Application No. 14827372.5), dated May 7, 2020.
"Kaneko et al., Aug. 4, 2006, Science, 313(5787): 670-673", Document D17 submitted with Notice of Opposition for European Patent No. 3087095 (Application No. 14827372.5), dated May 7, 2020.
"Notice of Opposition" to European Patent No. 3087095 (Application No. 14827372.5), dated May 7, 2020, 47 pages.
"Online Filing Acknowledgement for Notice of Opposition" for European Patent No. 3087095 (Application No. 14827372.5), dated May 7, 2020, 3 pages.
"Patel et al., Jul. 15, 2011, J Immunol., 187(2): 1015-1022", Document D09 submitted with Notice of Opposition for European Patent No. 3087095 (Application No. 14827372.5), dated May 7, 2020.
"PCT Request for as filed for PCT/US2014/072087 on Dec. 23, 2014", Document D34 submitted with Notice of Opposition for European Patent No. 3087095 (Application No. 14827372.5), dated May 7, 2020.
"Putnam and Miyake, Apr. 1958, J Biol Chem, 231(2):671-684", Document D33 submitted with Notice of Opposition for European Patent No. 3087095 (Application No. 14827372.5), dated May 7, 2020.
"Pyzik et al., Jul. 10, 2019, Front Immunol., 10: 1540", Document D31 submitted with Notice of Opposition for European Patent No. 3087095 (Application No. 14827372.5), dated May 7, 2020.
"Samuelsson et al., Jan. 19, 2001, Science, 291(5503): 484-486", Document D13 submitted with Notice of Opposition for European Patent No. 3087095 (Application No. 14827372.5), dated May 7, 2020.
"Schwab and Nimmerjahn, Mar. 2013, Nat Rev Immunol., 13(3): 176-189", Document D11 submitted with Notice of Opposition for European Patent No. 3087095 (Application No. 14827372.5), dated May 7, 2020.
"Sequence alignment of Seq ID No. 22 from D6 and Seq ID Nos. 1, 2, and 3 from the Patent", Document D32 submitted with Notice of Opposition for European Patent No. 3087095 (Application No. 14827372.5), dated May 7, 2020.
"Sequence Alignment of Seq ID Nos. 1-3 from Patent and corresponding portion of Uniprot ID: P01857", Document D24 submitted with Notice of Opposition for European Patent No. 3087095 (Application No. 14827372.5), dated May 7, 2020.
"Shields et al., Mar. 2, 2001, J Biol Chem., 276(9): 6591-6604", Document D23 submitted with Notice of Opposition for European Patent No. 3087095 (Application No. 14827372.5), dated May 7, 2020.
"Ulrichts et al., Oct. 1, 2018, J Clin Invest., 128(10): 4372-4386", Document D18 submitted with Notice of Opposition for European Patent No. 3087095 (Application No. 14827372.5), dated May 7, 2020.
"Vacarro et al., Dec. 2006, Proc Natl Acad Sci USA, 103(49): 18709-18714", Document D07 submitted with Notice of Opposition for European Patent No. 3087095 (Application No. 14827372.5), dated May 7, 2020.
"Vaccarro et al., Oct. 2005, Nat Biotechnol., 23(10): 1283-1288", Document D04 submitted with Notice of Opposition for European Patent No. 3087095 (Application No. 14827372.5), dated May 7, 2020.
"Ward & Ober, 2009, Chapter 4, Adv. Immunol., 103: 77-115", Document D05 submitted with Notice of Opposition for European Patent No. 3087095 (Application No. 14827372.5), dated May 7, 2020.
"Weiner and Carter, May 2005, 23(5): 556-557", Document D36 submitted with Notice of Opposition for European Patent No. 3087095 (Application No. 14827372.5), dated May 7, 2020.
"WO 2006/130834 A2 dated Dec. 7, 2006", Document D02 submitted with Notice of Opposition for European Patent No. 3087095 (Application No. 14827372.5), dated May 7, 2020.
"WO 2013/074598 A1 dated May 23, 2013", Document D06 submitted with Notice of Opposition for European Patent No. 3087095 (Application No. 14827372.5), dated May 7, 2020.
"WO 2015/100299 A1 dated Jul. 2, 2015" submitted with Notice of Opposition for European Patent No. 3087095 (Application No. 14827372.5), dated May 7, 2020.
Evoli et al., "Diagnosis and therapy of myasthenia gravis with antibodies to muscle-specific kinase", Autoimmunity Reviews, 2013, 12(9): 931-935.
Jaretzkl et al., "Myasthenia gravis: recommendations for clinical research standards. Task Force of the Medical Scientific Advisory Board of the Myasthenia Gravis Foundation of America", Ann Thorac Surg., Jul. 2000, 70(1): 327-334.
Joshi et al., "An Update on Disease Modifying Antirheumatic Drugs", Inflammation and Allergy—Drug Targets, 2014, 13: 249-261.
Li et al., "Myasthenia gravis: newer therapies offer sustained improvement", Cleveland Clinic Journal of Medicine, 2013, 80(11): 711-721.
Rosenwasser et al., "Anti-CD23", Clinical Reviews in Allergy and Immunology, Aug. 2005, 29(1): 61-72.
Silvestri et al., "Treatment-Refractory Myasthenia Gravis", Journal of Clinical Neuromuscular Disease, Jun. 2014, 15(4): 167-178.
Kasperkiewicz et al., "Pemphigus." Nat Rev Dis Primers. 2017;3:17026.
Van Faassen, et al., "Serum albumin-binding VH Hs with variable pH sensitivities enable tailored half-life extension of biologics," FASEB J. 2020 34(6): 8155-8171 doi: 10.1096/fj.201903231R. Epub Apr. 28, 2020.
Partial International Search Report issued for International Application No. PCT/EP2023/066180, mailed Sep. 27, 2023.

(56) References Cited

OTHER PUBLICATIONS

International Search Report and Written Opinion issued for PCT/EP2023/066163, mailed Sep. 27, 2023.
Bas Van Der Woning, "R&D Day: Fifth Efgartigimod Indication: Myositis," ArGENX, Jul. 20, 2021, pp. 23-37.
Basta and Dalakas, "High-dose intravenous immunoglobulin exerts its beneficial effect in patients with dermatomyositis by blocking endomysial deposition of activated complement fragments," J Clin Invest. 1994;94(5):1729-35.
Brinkhaus Maximilian et al., "The Fab region of IgG impairs the internalization pathway of FcRn upon Fc management," Nature Communications 13(1): 6073.
Challa et al., "Neonatal Fc receptor expression in macrophages is indispensable for IgG homeostatis MABS," 11(5):848-860.
Dalakas, "Update on Intravenous Immunoglobulin in Neurology: Modulating Neuro-autoimmunity, Evolving Factors on Efficacy and Dosing and Challenges on Stopping Chronic IVIg Therapy," Neurotherapeutics. 2021; 18(4):2397-2418.
Dalakas, "A controlled trial of high-dose intravenous immune globulin infusions as treatment for dermatomyositis," N J England J Med. 1993 329(27): 1993-2000.
Heo, "Efgartigimod: First Approval," Drugs. 2022;82(3):341-348.
International Search Report and Written Opinion for PCT/EP2023/054065 mailed May 3, 2023.
International Search Report and Written for PCT/EP2023/066162 mailed Aug. 16, 2023.
Julien et al., "Abstract No. L10 Efgartigimod Prevents Necrosis and Allows for Muscle Fiber Regeneration in a Humanized Mouse Model of Immune-mediated Necrotizing Myopathy (IMNM)," ACR Meeting Abstracts, ACR Conference 2022, Oct. 18, 2022, pp. 1-4.
Wang et al., "Antibody structure, instability, and formulation," J Pharm Sci. 2007;96(1):1-26.
Allen et al., "Efgartigimod in Chronic Inflammatory Demyelinating Polyneuropathy: Adhere Phase 2 Trial Design", Muscle and Nerve, Oct. 1, 2020, 62(Suppl. 1):abstract, 1 page.
Anonymous, "A Randomized, Double-Blinded, Placebo-Controlled Trial of Efgartigimod PH20 SC in Adult Patients With Pemphigus (Vulgaris or Foliaceus)", Jul. 16, 2021, Retrieved from: https://rctportal.niph.go.jp/en/detail?trial_id=jRCT2061210025, 4 pages.
Antohe et al., "Expression of Functionally active FcRn and the Differentiated Bidirectional Transport of IgG in Human Placental Endothelial Cells", Human Immunol., 2001, 62(2):93-105.
Arduin et al., "Highly reduced binding to high and low affinity mouse Fc gamma receptors by L234A/L235A and N297A Fc mutations engineered into mouse IgG2a", Molecular Immunology, 2015, 63(2):456-463.
Azevedo, "argenx Doses First Subject in Study Evaluating Subcutaneous ARGX-113 for Autoimmune Diseases", Myasthenia Gravis News, Oct. 31, 2017, 2 pages.
Bitonti et al., "Pulmonary delivery of an erythropoietin Fc fusion protein in non-human primates through an immunoglobulin transport pathway", PNAS, Jun. 29, 2004, 101(26):9763-9768.
Blumberg et al., "Blocking FcRn in humans reduces circulating IgG levels and inhibits IgG immune complex-mediated immune responses", Sci. Adv., Dec. 18, 2019, 5(12):eaax9586, 12 pages.
Broome et al., "Abstract PB0830: Efficacy and Safety of Efgartigimod PH20 Subcutaneous in Adult Patients with Primary Immune Thrombocytopenia: Advance SC, a Global Phase 3 Clinical Trial in Progress", Res Pract Thromb Haemost., 2021, 5(Suppl. 2), 2 pages.
Broome et al., "Efficacy and safety of the neonatal Fc receptor inhibitor efgartigimod in adults with primary immune thrombocytopenia (Advance IV): a multicentre, randomised, placebo-controlled, phase 3 trial", Lancet, Sep. 28, 2023, 402(10413):1648-1659.
Burmeister et al., "Crystal structure at 2.2 Å resolution of the MHC-related neonatal Fc receptor", Nature, Nov. 24, 1994, 372(6504):336-343.
Bystryn et al., "IVIg selectively and rapidly decreases circulating pathogenic autoantibodies in pemphigus vulgaris", Autoimmunity, Nov. 2006, 39(7):601-607.

ClinicalTrials.gov, "A Study of Nipocalimab in Adults With Primary Sjogren's Syndrome (pSS)", ClinicalTrials.gov Identifier: NCT04968912, Jul. 20, 2021, 9 pages.
ClinicalTrials.gov, "A Study to Assess Effectiveness and Safety of Efgartigimod in Chinese Patients With Lupus Nephritis (ZL-1103-013)", ClinicalTrials.gov Identifier: NCT05810948, Oct. 2, 2023, 17 pages.
ClinicalTrials.gov, "A Study to Assess the Long-term Safety and Efficacy of a Subcutaneous Formulation of Efgartigimod PH20 Sc in Adults With Pemphigus (Vulgaris or Foliaceus) (Address+)", ClinicalTrials.gov Identifier: NCT04598477, Oct. 22, 2020, 10 pages.
ClinicalTrials.gov, "Efficacy and Safety Study of Efgartigimod in Adults With Post-COVID-19 Pots (Pots)", ClinicalTrials.gov Identifier: NCT05633407, Nov. 29, 2022, 13 pages.
ClinicalTrials.gov, "Evaluating the Long-Term Safety and Tolerability of Efgartigimod PH20 SC Administered Subcutaneously in Patients With Generalized Myasthenia Gravis (Adaptsc+)", ClinicalTrials.gov Identifier: NCT04818671, Mar. 26, 2021, 7 pages.
ClinicalTrials.gov, "History of Changes for Study: NCT05267600—A Phase 2/3 Study of Efgartigimod PH20 SC in Adult Participants With Bullous Pemphigoid (Ballad)", Apr. 14, 2022, 7 pages.
ClinicalTrials.gov, "History of Changes for Study: NCT05810961—A Study to Assess Effectiveness and Safety of Efgartigimod in Chinese Patients With Primary Membranous Nephropathy (ZL-1103-014)", Oct. 2, 2023, 11 pages.
Dalakas et al., "High-dose intravenous immune globulin for stiff-person syndrome", The New England Journal of Medicine, Dec. 27, 2001, 345(26):1870-1876.
Dall'Acqua et al., "Properties of Human IgG1s Engineered for Enhanced Binding to the Neonatal Fc receptor (FcRn)", Journal of Biological Chemistry, Aug. 18, 2006, 281(33):23514-23524.
Deisenhofer, "Crystallographic Refinement and Atomic Models of a Human Fc Fragment and Its Complex with Fragment B of Protein A from *Staphylococcus aureus* at 2.9- and 2.8-Å Resolution", Biochemistry, Apr. 28, 1981, 20(9):2361-2370.
Dickinson et al., "Bidirectional FcRn-dependent IgG transport in a polarized human intestinal epithelial cell line", The Journal of Clinical Investigation, Oct. 1999, 104(7):903-911.
Dylewski et al., "Exploiting the neonatal crystallizable fragment receptor to treat kidney disease", Kidney International, 2024, 105(1):54-64.
Firan et al., "The MHC class I-related receptor, FcRn, plays an essential role in the maternofetal transfer of gamma-globulin in humans", International Immunology, 2001, 13(8):993-1002.
Ghanima et al., "Pharmacokinetic / Pharmacodynamic (PK/PD) Simulations Guide Selection of the Dose for Administration of Efgartigimod Subcutaneously in a Phase 3 Clinical Trial in Patients with Primary Immune Thrombocytopenia", Blood, Nov. 5, 2021, 138(Supplement 1):3165-3167.
Ghetie et al., "FcRn: the MHC class I-related receptor that is more than an IgG transporter", Immunology Today, 1997, 18(12):592-598.
Ghetie et al., "Multiple Roles for the Major Histocompatibility Complex class I-Related Receptor FcRn", Annu. Rev. Immunol., 2000, 18(1):739-766.
Goebeler et al., "Treatment of pemphigus vulgaris and foliaceus with efgartigimod, a neonatal Fc receptor inhibitor: a phase II multicentre, open-label feasibility trial", British Journal of Dermatology, 2022, 186(3):429-439.
"Guidance for Industry Estimating the maximum safe starting dose in initial clinical trials for therapeutics in adult healthy volunteers", FDA, Jul. 2005, 30 pages.
Guptill et al., "Effect of FcRn antagonism on protective antibodies and to vaccines in IgG-mediated autoimmune diseases pemphigus and generalised myasthenia gravis", Autoimmunity, 2022, 55(8):620-631.
Ha et al., "Immunoglobulin Fc Heterodimer Platform Technology: From Design to Applications in Therapeutic Antibodies and Proteins", Frontiers in Immunology, Oct. 6, 2016, 7(394), pp. 1-16.

(56) References Cited

OTHER PUBLICATIONS

Haller, "Converting Intravenous Dosing to Subcutaneous Dosing with Recombinant human Hyaluronidase", Pharmaceutical Technology, Advanstar Communications Inc., Oct. 2, 2007, 31(10), pp. 1-5.

Hettmann et al., "Development of the clinical candidate PBD-C06, a humanized pGlu3-ABeta-specific antibody against Alzheimer's disease with reduced complement activation", Scientific Reports, 2020, 10(3294), pp. 1-13.

Hinton et al., "Engineered human IgG Antibodies with Longer Serum Half-Lives in Primates", The Journal of Biological Chemistry, Feb. 20, 2004, 279(8):6213-6216.

Hoffman, "Subcutaneous Efgartigimod Shows Noninferiority to IV Formulation in Generalized Myasthenia Gravis", NeurologyLive, Retrieved from: https://web.archive.org/web/20220326043901/https://www.neurologylive.com/view/subcutaneous-efgartigimod-noninferior-iv-formulation-vygart-generalized-myasthenia-gravis, Mar. 23, 2022, 3 pages.

Howard et al., "A double-blind placebo-controlled study to evaluate safety and efficacy of FcRn antagonist ARGX-113 (efgartigimod) in generalized myasthenia gravis", 70th Annual Meeting of the American Academy of Neurology, AAN, 2018, 1 page.

Howard Jr. et al., "Poster 133: Response to Coronavirus 2019 Vaccination in Patients Receiving Efgartigimod", AANEM, Sep. 21-24, 2022, 1 page.

Howard Jr. et al., "Safety, efficacy, and tolerability of efgartigimod in patients with generalised myasthenia gravis (ADAPT): a multicentre, randomised, placebo-controlled, phase 3 trial", Lancet Neurology, Jul. 2021, 20(7):526-536.

Hubbard et al., "Poster-97: Design of a Phase 2, Multicenter, Randomized, Placebo-Controlled, Double-blind Study to Assess the Efficacy and Safety of Nipocalimab, an FcRn Antagonist, in Adults with Primary Sjogrens Syndrome", Clinical and Experimental Rheumatology, 2022, 40:2477-2579.

Ishii-Watabe et al., "Molecular Design of Therapeutics Monoclonal Antibodies", Journal of Pharmaceutical Science and Technology, Japan, 2014, 74(1):4-11 (English Abstract Submitted).

Israel et al., "Increased clearance of IgG in mice that lack Beta 2-microglobulin: possible protective role of FcRn", Immunology, 1996, 89(4):573-578.

Kabat et al., "Sequences of Proteins of Immunological Interest", 5th Edition, U.S. Department of Health and Human Services, 1991, (Title Page and Table of Contents), 11 pages.

Kasprick et al., "Treatment with anti-neonatal Fc receptor (FcRn) antibody ameliorates experimental epidermolysis bullosa acquisita in mice", Br J Pharmacol., 2020, 177(10):2381-2392.

Kiessling et al., "The FcRn inhibitor rozanolixizumab reduces human serum IgG concentration: A randomized phase 1 study", Sci. Transl. Med., Nov. 1, 2017, 9(414), pp. 1-12.

Kiessling et al., "Safety, Pharmacokinetics and Pharmacodynamics of the FcRn Inhibitor UCB7665: A Phase I Study", Journal of the Peripheral Nervous System, 2017, 22(3):226-414, 1 page.

Kim et al., "Localization of the site of the murine IgG1 molecule that is involved in binding to the murine intestinal Fc receptor", Eur. J. Immunol., 1994, 24(10):2429-2434.

Knoebl et al., "Pb2305-Efgartigimod: Clinical Development of a Novel FcRn Antagonist in the Treatment of Autoimmune Diseases", Hemasphere, 2022, 6:2175-2176.

Kobayashi et al., "FcRn-mediated transcytosis of immunoglobulin G in human renal proximal tubular epithelial cells", Am J Physiol Renal Physiol., 2002, 282:F358-F365.

Lobner et al., "Engineered IgG1-Fc—one fragment to bind them all", Immunological Reviews, 2016, 270(1):113-131.

Maho-Vaillant et al., "FcRn Antagonism Leads to a Decrease of Desmoglein-Specific B Cells: Secondary Analysis of a Phase 2 Study of Efgartigimod in Pemphigus Vulgaris and Pemphigus Foliaceus", Frontiers in Immunology, May 2022, 13(Article 863095), pp. 1-14.

McCarthy et al., "Bidirectional transcytosis of IgG by the rat neonatal Fc receptor expressed in a rat kidney cell line: a system to study protein transport across epithelia", Journal of Cell Science, 2000, 113(Pt 7):1277-1285.

Medesan et al., "Comparative studies of rat IgG to further delineate the Fc:FcRn interaction site", European Journal of Immunology, 1998, 28(7):2092-2100.

Miyagawa, "Idiopathic Thrombocytopenia Purpura", Mebio., 2017, 34(6):102-107.

Olaru et al., "Neonatal Fc Receptor Promotes Immune Complex-Mediated Glomerular Disease", J Am Soc Nephrol, 2014, 25(5):918-925.

Patel et al., "FcRn blockade by Fc engineering ameliorates arthritis in a murine model", J Immunol., Jul. 15, 2011, 187(2):1015-1022.

Patel et al., "Neonatal Fc receptor in human immunity: Function and role in therapeutic intervention", J Allergy Clin Immunol., Sep. 2020, 146(3):467-478.

Peene et al., "AB0520: Treatment of Primary Sjogren's Syndrome by Inhibiting FcRn: A Phase 2 Randomized, Placebo Controlled, Double-Blind, Proof of Concept Study with Efgartigimod", Scientific Abstracts, May 30, 2023, 1455-1456.

Peter et al., "Targeting FcRn for immunomodulation: Benefits, risks, and practical considerations", J. Allergy Clin. Immunol., Sep. 2020, 146(3):479-491.

Polanco et al., "Spontaneous Remission of Nephrotic Syndrome in Idiopathic Membranous Nephropathy", J Am Soc Nephrol., 2010, 21(4):697-704.

Popov et al., "The Stoichiometry and Affinity of the Interaction of Murine Fc Fragments with the MHC Class I-Related receptor, FcRn", Molecular Immunology, 1996, 33(6):521-530.

Press Release "argenx Announces Approval of Vyvgart (efgartigimod alfa) in Japan for Adults with Primary Immune Thrombocytopenia", Mar. 26, 2024, 4 pages.

Press Release "argenx Reports Topline Results from Address Study of Efgartigimod SC in Pemphigus", Dec. 20, 2023, 5 pages.

Press Release "argenx Reports Topline Results from Advance-SC Study of Vyvgart Hytrulo in Primary Immune Thrombocytopenia", Nov. 28, 2023, 4 pages.

Press Release, "argenx Advances Clinical Development of Efgartigimod in Primary Sjogren's Disease", Mar. 27, 2024, 3 pages.

Raghavan et al., "Analysis of the pH Dependence of the Neonatal Fc Receptor/Immunoglobulin G Interaction Using Antibody and Receptor Variants", Biochemistry, 1995, 34(45):14649-14657.

Rojas-Rivera et al., "Recent Clinical Trials Insights into the Treatment of Primary Membranous Nephropathy", Drugs, 2022, 82(2):109-132.

Rudikoff et al., "Single amino acid substitution altering antigen-binding specificity", Proc. Natl. Acad. Sci., Mar. 1982, 79(6):1979-1983.

Spiekermann et al., "Receptor-mediated Immunoglobulin G Transport Across Mucosal Barriers in Adult Life: Functional Expression of FcRn in the Mammalian Lung", J. Exp. Med., Aug. 5, 2002, 196(3):303-310.

Ulrichts et al., "Supplementary Data Neonatal Fc receptor antagonist efgartigimod safely and sustainably reduces IgGs in humans", J. Clin. Invest., Supplementary Data, 2018, 128(10):4372-4386, pp. 1-15.

Verschuuren et al., "A double-blind placebocontrolled study to evaluate safety and efficacy of fcrn antagonist ARGX-113 in generalized MG", Journal of Neuromuscular Diseases, 2018, 5(Supplement 1):S327-S328.

Vitetta et al., "Considering Therapeutic Antibodies", Science, Jul. 21, 2006, 313(2):308-309.

Warne, "Development of high concentration protein biopharmaceuticals: The use of platform approaches in formulation development", European Journal of Pharmaceutics and Biopharmaceutics, 2011, 78(2):208-212.

Wittlin et al., "Pharmacokinetic/Pharmacodynamic Simulations Guide Selection of the Dose for Administration of Efgartigimod Subcutaneously in a Phase 3 Clinical Trial in Patients with Primary Immune Thrombocytopenia", British Journal of Haematology, Abstract of the 62nd Annual Scientific Meeting of The British Society for Haematology, Apr. 1, 2022, 197(Suppl. 1):44.

(56) References Cited

OTHER PUBLICATIONS

Yoshida et al., "Human Neonatal Fc Receptor Mediates Transport of IgG into Luminal Secretions for Delivery of Antigens to Mucosal Dendritic Cells", Immunity, Jun. 2004, 20(6):769-783.
"Corrected Filing Receipt for U.S. Appl. No. 61/920,547 dated Apr. 18, 2014", Document D26 submitted with to Notice of Opposition for European Patent No. 3087095 (Application No. 14827372.5), dated May 7, 2020, 3 pages.
International Preliminary Report on Patentability received for PCT Patent Application No. PCT/EP2018/084034, mailed on Jun. 18, 2020, 11 pages.
International Preliminary Report on Patentability received for PCT Patent Application No. PCT/US2006/021456, mailed on Dec. 6, 2007, 8 pages.
International Search Report and Written Opinion received for PCT Patent Application No. PCT/EP2023/050980, mailed on Apr. 12, 2023, 13 pages.
International Search Report and Written Opinion received for PCT Patent Application No. PCT/EP2023/061012, mailed on Aug. 3, 2023, 15 pages.
International Search Report and Written Opinion received for PCT Patent Application No. PCT/EP2023/066180, mailed on Nov. 17, 2023, 19 pages.
International Search Report and Written Opinion received for PCT Patent Application No. PCT/IB2022/000443, mailed on Mar. 6, 2023, 29 pages.
International Search Report and Written Opinion received for PCT Patent Application No. PCT/IB2023/000679, mailed on Apr. 3, 2024, 17 pages.
International Search Report and Written Opinion received for PCT Patent Application No. PCT/IB2023/000688, mailed on Apr. 29, 2024, 16 pages.
International Search Report and Written Opinion received for PCT Patent Application No. PCT/IB2023/000696, mailed on Jun. 4, 2024, 21 pages.
International Search Report and Written Opinion received for PCT Patent Application No. PCT/IB2024/000018, mailed on May 24, 2024, 16 pages.
International Search Report and Written Opinion received for PCT Patent Application No. PCT/IB2024/000041, mailed on Jun. 3, 2024, 14 pages.
International Search Report and Written Opinion received for PCT Patent Application No. PCT/IB2024/000120, dated Jul. 15, 2024, 14 pages.
International Search Report and Written Opinion received for PCT Patent Application No. PCT/US2006/021456, mailed on Nov. 17, 2006, 8 pages.
Invitation to Pay Additional Fees received for PCT Patent Application No. PCT/IB2023/000696, mailed on Apr. 12, 2024, 15 pages.
Press Release, "argenx and Zai Lab Announce Approval of Efgartigimod Alfa Injection (Subcutaneous Injection) for Generalized Myasthenia Gravis in China", Jul. 16, 2024, 4 pages.
Press Release, "argenx Announces FDA Approval of Vyvgart Hytrulo for Chronic Inflammatory Demyelinating Polyneuropathy", Jun. 21, 2024, 5 pages.
Press Release, "argenx Announces Publication in The Lancet Neurology of Pivotal Adhere Study Data in Chronic Inflammatory Demyelinating Polyneuropathy", Sep. 19, 2024, 5 pages.
Press Release, "argenx Data Highlight Evidence that Vyvgart and Vyvgart Hytrulo Drive Transformative Outcomes for Patients with Debilitating Autoimmune Disease", Apr. 16, 2024, 6 pages.
Press Release, "argenx Highlights Breadth of Autoimmune Pipeline with New Multifocal Motor Neuropathy Data at 2024 Peripheral Nerve Society Annual Meeting", Jun. 25, 2024, 5 pages.
Press Release, "argenx Highlights Data Showing Patient Impact Across Multiple Immunology Programs at 2024 American Association of Neuromuscular & Electrodiagnostic Medicine Annual Meeting and Myasthenia Gravis Foundation of America Scientific Sessions", Oct. 15, 2024, 9 pages.
Press Release, "argenx Reports First Quarter 2024 Financial Results and Provides Business Update", May 9, 2024, 7 pages.
Press Release, "argenx Reports Half Year 2024 Financial Results and Provides Second Quarter Business Update", Jul. 25, 2024, 7 pages.
Press Release, "argenx to unveil its 'Vision 2030: Taking Breakthrough Science to 50,000 Patients' during its Upcoming R&D Day on Jul. 16, 2024", Jun. 17, 2024, 4 pages.
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, Sep. 5, 2004, 87(5):614-622.
"Appeal from the United States District Court for the District of Delaware", *Amgen Inc.* v. *Sanofi*, 2017-1480, Oct. 5, 2017, 24 pages.
"VYVGART™ (efgartigimod alfa-fcab) injection, for intravenous Use", Initial U.S. Approval, Dec. 2021, 14 pages.
Alexion Pharmaceuticals Inc., "A Phase 1b/2, Multicenter, Open-Label, Safety, and Dose-Finding Study of SYNT001 in Subjects with Pemphigus (Vulgaris or Foliaceus)", Retrieved from: https://cdn.clinicaltrials.gov/large-docs/04/NCT03075904/SAP_000.pdf, Protocol ID: SYNT001-103, NCT No. NCT03075904, Mar. 25, 2019, 32 pages.
Briani et al., "Therapeutic Monoclonal Antibody Therapies in Chronic Autoimmune Demyelinating Neuropathies", Neurotherapeutics, 2022, 19(3):874-884.
Brinkhaus et al., "Glycine 236 in the Lower Hinge Region of Human IgG1 Differentiates FcgammaR from Complement Effector Function", The Journal of Immunology, Dec. 15, 2020, 205(12):3456-3467.
Miyamoto et al., "Pemphigus "Is Rituximab effective?"", MB Derma, 2012, 190:91-93 (English Translation and Official Copy).
Monnet et al., "Combined glyco- and protein-Fc engineering simultaneously enhance cytotoxicity and half-life of a therapeutic antibody", mAbs, Mar./Apr. 2014, 6(2):422-436.
Nelke et al., "Neonatal Fc Receptor-Targeted Therapies in Neurology", Neurotherapeutics, 2022, 19(3):729-740.
Press Release, "argenx Advances Clinical Development of Efgartigimod SC in Idiopathic Inflammatory Myopathies", Nov. 20, 2024, 3 pages.
Press Release, "argenx and Zai Lab Announce Approval of VYVGART Hytrulo for Chronic Inflammatory Demyelinating Polyneuropathy in China", Nov. 11, 2024, 4 pages.
Press Release, "argenx Announces Approval of VYVDURA (efgartigimod alfa and hyaluronidase-qvfc) in Japan for Adults with Chronic Inflammatory Demyelinating Polyneuropathy", Dec. 27, 2024, 4 pages.
Press Release, "argenx Highlights 2025 Strategic Priorities", Jan. 13, 2025, 7 pages.
Press Release, "argenx Reports Third Quarter 2024 Financial Results and Provides Business Update", Oct. 31, 2024, 8 pages.
Sanchez-Tejerina et al., "New Targeted Agents in Myasthenia Gravis and Future Therapeutic Strategies", Journal of Clinical Medicine, 2022, 11(21):6394, pp. 1-20.
Simpson et al., "The Validated Investigator Global Assessment for Atopic Dermatitis (vIGA-AD): The development and reliability testing of a novel clinical outcome measurement instrument for the severity of atopic dermatitis", Journal of the American Academy of Dermatology, Sep. 2020, 83(3):839-846.
Smith et al., "Mouse model recapitulating human FcGamma receptor structural and functional diversity", PNAS, Apr. 17, 2012, 109(16):6181-6186.
Svačina et al., "Chronic Inflammatory Demyelinating Polyneuropathy (CIDP): Current Therapies and Future Approaches", Current Pharmaceutical Design, 2022, 28(11):854-862.
Syntimmune, Inc., "Syntimmune Announces Positive Preliminary Results from Clinical Proof-of-Concept Trial of SYNT001 in Pemphigus Vulgaris and Foliaceus", Retrieved from: https://www.businesswire.com/news/home/20180517006057/en/Syntimmune-Announces-Positive-Preliminary-Results-Clinical-Proofof-Concept, May 17, 2018, 2 pages.

(56) References Cited

OTHER PUBLICATIONS

International Search Report and Written Opinion received for PCT Application No. PCT/IB2024/000374, mailed on Nov. 12, 2024, 16 pages.
International Search Report and Written Opinion received for PCT Application No. PCT/IB2024/000716, mailed on Mar. 21, 2025, 16 pages.

* cited by examiner ively in ASCII format and is hereby incorporated by reference in its entirety. Said ASCII copy, created on Jan. 8, 2021, is named 712704_AGX5-052_ST25.txt and is 18,091 bytes in size.

METHODS FOR TREATING PEMPHIGUS DISORDERS

RELATED APPLICATIONS

This application claims priority to U.S. Provisional Patent Application No. 62/958,543, filed Jan. 8, 2020, and U.S. Provisional Patent Application No. 62/960,647, filed Jan. 13, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 8, 2021, is named 712704_AGX5-052_ST25.txt and is 18,091 bytes in size.

FIELD

The present disclosure relates to methods of treating pemphigus disorders, including but not limited to pemphigus vulgaris and pemphigus foliaceus. The methods involve use of an antagonist of human neonatal Fc receptor (FcRn), which in certain embodiments is efgartigimod.

BACKGROUND

Pemphigus is a group of chronic blistering epithelial diseases in which the production of IgG autoantibodies against extracellular domains of certain cell membrane proteins of keratinocytes results in acantholysis (loss of cell-cell adhesion between keratinocytes). Major forms of pemphigus include pemphigus vulgaris (PV) and pemphigus foliaceus (PF). Current treatment strategies in pemphigus vary in their capacity to induce disease control (DC) and durable clinical remission (CR). Corticosteroids rapidly affect PV symptoms but must be administered at high daily doses (e.g. oral prednisone at 1 to 1.5 mg/kg/day) to attain effectiveness. If DC is not achieved after 3 to 4 weeks, prednisone dose must be increased and in patients with very active disease, an intravenous (IV) bolus of corticosteroids (e.g., methylprednisolone) may be preferred, especially at treatment initiation. In the Ritux 3 study, the rituximab therapy in combination with low-dose corticosteroids allowed 89% of patients to achieve complete remission off therapy (CRoff) at 24 months, while systemic corticosteroids alone allowed only 34% of patients to achieve CRoff. Joly P. et al., *Lancet* 2017; 389:2031-2040. While treatment with rituximab offers pemphigus patients an improved therapeutic option, rituximab has a relatively slow onset of action requiring concomitant use of corticosteroids in moderate to high doses between 0.5 to 1.5 mg/kg/day, depending on disease severity, to induce DC. Moreover, patients receiving rituximab relapse in 25-60% of cases, requiring additional cycles of rituximab, and rituximab therapy poses an increased risk of infections as a consequence of systemic B-cell depletion. All these factors, along with the tremendous physical burden of pemphigus disease, necessitate the need for a fast-acting treatment that allows for a quick resolution of blisters, associated pain and physical discomfort, and permit quick steroid tapering to avoid steroid-associated side effects and toxicities. Therefore, there remains a need in pemphigus patients for a safer drug with a rapid onset of action that would achieve early disease control and maintain clinical remission, with or without a minimal dose of corticosteroids (e.g. prednisone 20 mg per day or 10 mg per day, or less).

SUMMARY OF THE INVENTION

The instant disclosure is based on the discovery that human neonatal Fc receptor (FcRn) antagonists are highly effective in treating pemphigus and pemphigus-related disorders. Accordingly, the instant disclosure is broadly directed, at least in part, to methods for treating pemphigus and pemphigus-related disorders with FcRn antagonists.

In one aspect, the disclosure is directed to a method of treating pemphigus, comprising administering to a subject in need thereof an effective amount of a human neonatal Fc receptor (FcRn) antagonist, wherein the subject has (a) newly diagnosed pemphigus, (b) relapsing pemphigus, or (c) refractory pemphigus, thereby treating pemphigus in the subject.

In another aspect, the disclosure is directed to a method of treating pemphigus, comprising (i) selecting a subject that has (a) newly diagnosed pemphigus, (b) relapsing pemphigus, or (c) refractory pemphigus; and (ii) administering to the subject an effective amount of a human neonatal Fc receptor (FcRn) antagonist.

In certain aspects, the disclosure is also based on the surprising discovery that FcRn antagonists can achieve rapid disease control (e.g., inhibition of new lesion formation and beginning of healing of established lesions) of pemphigus. In certain embodiments, disease control can be obtained within about 1 month of administration of the initial dose of FcRn antagonist. In certain embodiments, disease control can be obtained within about 3 weeks, within about 2 weeks, or within about 1 week of administration of the initial dose of FcRn antagonist. In exemplary embodiments, disease control can be obtained within about 14-16 days of administration of the initial dose of FcRn antagonist. In certain embodiments, disease control can be obtained after 1-4 doses (e.g., infusions or subcutaneous administrations) of FcRn antagonist. In certain exemplary embodiments, the methods of the invention achieve disease control after 1 or 2 doses (e.g., infusions or subcutaneous administrations) of FcRn antagonist.

In yet other aspects, the disclosure is also based on the surprising discovery that FcRn antagonists, optionally when co-administered with a corticosteroid, can achieve disease control (e.g., rapid disease control) of pemphigus at much lower doses of corticosteroids than conventional therapies. Thus, in certain aspects the disclosure is based on the surprising discovery that the methods of the invention provide unprecedented levels of "corticosteroid-sparing."

For example, conventional therapies require very high weight-based dosing of corticosteroids (e.g., 1 or 2 mg/kg/day). By contrast, in certain embodiments, the methods of the invention can achieve disease control (e.g., rapid disease control) at corticosteroid doses of 0.5 mg/kg/day or less. In exemplary embodiments, the methods of the invention can achieve disease control (e.g., rapid disease control) at corticosteroid doses of less than about 0.4 mg/kg/day. In other exemplary embodiments, the methods of the invention can achieve disease control (e.g., rapid disease control) at corticosteroid doses of less than about 0.3 mg/kg/day. In other exemplary embodiments, the methods of the invention can achieve disease control (e.g., rapid disease control) at corticosteroid doses of less than about 0.25 mg/kg/day. In other exemplary embodiments, the methods of the invention can achieve disease control (e.g., rapid disease control) at corticosteroid doses of less than about 0.2 mg/kg/day. In other exemplary embodiments, the methods of the invention can achieve disease control (e.g., rapid disease control) at corticosteroid doses of less than about 0.1 mg/kg/day. In other exemplary embodiments, the methods of the invention can achieve disease control (e.g., rapid disease control) at corticosteroid doses of less than about 0.05 mg/kg/day.

In other embodiments, the methods of the invention can achieve disease control (e.g., rapid disease control) at much lower fixed doses of corticosteroids than conventional therapies. For example, while convention therapies require high fixed doses of corticosteroid (e.g., 100-150 mg/day), in certain embodiments, the methods of invention can achieve disease control (e.g., rapid disease control) at corticosteroid doses of 20 mg/day or less. In exemplary embodiments, the methods of the invention can achieve disease control (e.g., rapid disease control) at corticosteroid doses of less than about 17.5 mg/day. In other exemplary embodiments, the methods of the invention can achieve disease control (e.g., rapid disease control) at corticosteroid doses of less than about 15 mg/day. In other exemplary embodiments, the methods of the invention can achieve disease control (e.g., rapid disease control) at corticosteroid doses of less than about 12.5 mg/day. In other exemplary embodiments, the methods of the invention can achieve disease control (e.g., rapid disease control) at corticosteroid doses of less than about 10 mg/day. In other exemplary embodiments, the methods of the invention can achieve disease control (e.g., rapid disease control) at corticosteroid doses of less than about 9 mg/day. In other exemplary embodiments, the methods of the invention can achieve disease control (e.g., rapid disease control) at corticosteroid doses of less than about 8 mg/day. In other exemplary embodiments, the methods of the invention can achieve disease control (e.g., rapid disease control) at corticosteroid doses of less than about 7 mg/day. In other exemplary embodiments, the methods of the invention can achieve disease control (e.g., rapid disease control) at corticosteroid doses of less than about 6 mg/day. In other exemplary embodiments, the methods of the invention can achieve disease control (e.g., rapid disease control) at corticosteroid doses of less than about 5 mg/day. In other exemplary embodiments, the methods of the invention can achieve disease control (e.g., rapid disease control) at corticosteroid doses of less than about 4 mg/day. In other exemplary embodiments, the methods of the invention can achieve disease control (e.g., rapid disease control) at corticosteroid doses of less than about 3 mg/day. In other exemplary embodiments, the methods of the invention can achieve disease control (e.g., rapid disease control) at corticosteroid doses of less than about 2 mg/day. In still other exemplary embodiments, the methods of the invention can achieve disease control (e.g., rapid disease control) at corticosteroid doses of less than about 1 mg/day.

In yet other exemplary embodiments, the methods of the invention can achieve disease control in the absence of corticosteroids. Thus, in certain aspects, the disclosure is directed to FcRn antagonist monotherapy for treatment of pemphigus disorders.

In certain embodiments, disease control is obtained within about 24 weeks, about 23 weeks, about 22 weeks, about 21 weeks, about 20 weeks, about 15 weeks, about 13 weeks, about 12 weeks, about 10 weeks, about 9 weeks, about 8 weeks, about 7 weeks, about 6 weeks, about 5 weeks, about 4 weeks, about 3 weeks, about 2 weeks, or about 1 week of administration of the initial dose of FcRn antagonist. In certain embodiments, disease control is obtained in 1 to 24 weeks, in 1 to 20 weeks, in 1 to 15 weeks, in 1 to 13 weeks, in 1 to 12 weeks, 1 to 10 weeks, in 1 to 6 weeks, in 1 to 4 weeks, in 1 week to 16 days, or in 1 to 2 weeks of administration of the initial dose of FcRn antagonist. In a specific embodiment, disease control is obtained in 1 to 13 weeks of administration of the initial dose of FcRn antagonist.

In other aspects, the disclosure is based on the surprising discovery that the methods of the invention achieve complete remission (e.g., no new lesions, and all established lesions completely healed) within about 4 months of administration of the initial dose of FcRn antagonist. In certain embodiments, complete remission is obtained within about 41 weeks, about 24 weeks, about 23 weeks, about 22 weeks, about 21 weeks, about 20 weeks, about 15 weeks, about 13 weeks, about 12 weeks, about 10 weeks, about 9 weeks, about 8 weeks, about 7 weeks, about 6 weeks, about 5 weeks, about 4 weeks, about 3 weeks, or about 2 weeks of administration of the initial dose of FcRn antagonist. In certain embodiments, complete remission is obtained in 2 to 41 weeks, in 2 to 24 weeks, in 2 to 20 weeks, in 2 to 15 weeks, in 2 to 13 weeks, in 2 to 12 weeks, in 2 to 10 weeks, or in 2 to 6 weeks of administration of the initial dose of FcRn antagonist. In a specific embodiment, complete remission is obtained in 2 to 41 weeks of administration of the initial dose of FcRn antagonist. In exemplary embodiments, complete remission is obtained following biweekly administration of the FcRn antagonist and about 2 mg/kg/day of corticosteroid or less (e.g., about 1 mg/kg/day, about 0.75 mg/kg/day, about 0.5 mg/kg/day, about 0.4 mg/kg/day, about 0.35 mg/kg/day, about 0.3 mg/kg/day, about 0.29 mg/kg/day, about 0.28 mg/kg/day, about 0.27 mg/kg/day, about 0.26 mg/kg/day, about 0.25 mg/kg/day, about 0.24 mg/kg/day, about 0.23 mg/kg/day, about 0.22 mg/kg/day, about 0.21 mg/kg/day or about 0.2 mg/kg/day). In exemplary embodiments, complete remission is obtained following weekly administration of the FcRn antagonist and about 2 mg/kg/day of corticosteroid or less (e.g., about 1 mg/kg/day, about 0.75 mg/kg/day, about 0.5 mg/kg/day, about 0.4 mg/kg/day, about 0.35 mg/kg/day, about 0.3 mg/kg/day, about 0.29 mg/kg/day, about 0.28 mg/kg/day, about 0.27 mg/kg/day, about 0.26 mg/kg/day, about 0.25 mg/kg/day, about 0.24 mg/kg/day, about 0.23 mg/kg/day, about 0.22 mg/kg/day, about 0.21 mg/kg/day or about 0.2 mg/kg/day). In exemplary embodiments, complete remission is obtained following biweekly administration of the FcRn antagonist and about 20 mg/day of corticosteroid or less (e.g., about 20 mg/day, about 17.5 mg/day about 15 mg/day, about 10 mg/day, about 5 mg/day, about 4 mg/day, about 3 mg/day, about 2 mg/day or about 1 mg/day). In exemplary embodiments, complete clinical remission is obtained following weekly administration of the FcRn antagonist and about 20 mg/day of corticosteroid or less (e.g., about 20 mg/day, about 17.5 mg/day about 15 mg/day, about 10 mg/day, about 5 mg/day, about 4 mg/day, about 3 mg/day, about 2 mg/day or about 1 mg/day). In certain exemplary embodiments, the methods of the invention can achieve complete clinical remission in the absence of corticosteroids.

In certain embodiments, the methods of the invention obtain Pemphigus Disease Area Index (PDAI) activity score improvement of at least about 50%, at least about 60%, at least about 70%, at least about 80%, or at least about 90%. In other embodiment, the methods of the invention result in an absolute PDAI activity score of 6 or less (e.g., an absolute PDAI activity score of 6, an absolute PDAI activity score of 5, an absolute PDAI activity score of 4, an absolute PDAI activity score of 3, an absolute PDAI activity score of 2, an absolute PDAI activity score of 1, or an absolute PDAI activity score of 0).

In other aspects, the disclosure is based on the surprising discovery that the methods of the invention achieve synergistic effects when FcRn antagonists are combined with low doses of corticosteroids. Without being bound to any particular theory, it is thought that the combination of FcRn antagonists and corticosteroids is capable of stimulating new basement membrane (e.g., via desmoglein 1 (i.e., DSG1 or Dsg-1) and/or desmoglein 3 (i.e., DSG3 or Dsg-3) synthesis) while also clearing pathogenic autoantibodies (e.g., anti-DSG1 or anti-DSG3 autoantibodies). Therefore, in certain exemplary embodiments, the FcRn antagonist is administered in combination with low doses of corticosteroid (e.g., about 0.2 or about 0.25 or about 0.5 mg/kg/day of oral prednisone or equivalents thereof). In preferred embodiments, the corticosteroid is administered orally in low doses. In certain embodiments, the corticosteroid is administered topically to the skin. In certain embodiments, the corticosteroid is administered systemically by intravenous injection or infusion.

In still other aspects, the invention is based on the discovery that newly diagnosed pemphigus patients and pemphigus patients previously treated with corticosteroids may be treated with an FcRn antagonist and subsequently tapered off treatment with corticosteroids much earlier and/or at higher initial levels of corticosteroids than conventional therapies. For example, conventional therapies typically require sustained treatment of pemphigus with corticosteroids and gradual and minimal tapering of the corticosteroids once disease control is observed. By contrast, the methods of the invention can begin tapering of corticosteroids much earlier and with larger dose reductions than conventional therapies. Accordingly, an aspect of the disclosure is a method of treating pemphigus, comprising administering to a subject in need thereof an effective amount of a human neonatal Fc receptor (FcRn) antagonist and an initial tapering dose of corticosteroid beginning at ≤2 mg prednisone/kg/day or equivalent. In some embodiments, the initial tapering dose is less than or equal to about 1.5, about 1.0, about 0.75, about 0.5, or about 0.2 mg prednisone/kg/day or equivalent. In certain exemplary embodiments, the initial tapering dose of corticosteroid is ≤ 0.5 mg prednisone/kg/day or equivalent.

In certain embodiments, corticosteroid tapering can begin once disease control has been achieved. As noted above, a surprising finding is that pemphigus patients treated with an FcRn antagonist may begin corticosteroid tapering much earlier than with conventional therapies. In certain embodiments, corticosteroid tapering can begin within about 10 weeks, about 9 weeks, about 8 weeks, about 7 weeks, about 6 weeks, about 5 weeks, about 4 weeks, about 3 weeks and about 2 weeks of administration of the initial dose of FcRn antagonist. In other embodiments, corticosteroid tapering can begin following disease control or following complete clinical remission. In certain embodiments, the tapering of corticosteroids can begin within about 1 month, within about 3 weeks, within about 2 weeks or within about 1 week of administration of the initial dose of FcRn antagonist.

In still other embodiments, the methods of invention allow for more rapid tapering of corticosteroids than conventional therapies. For example, whereas conventional therapies only allow for corticosteroid tapering as frequently as once a month, the FcRn antagonists of the invention may be tapered more frequently, provided that disease control is maintained. In certain exemplary embodiments, a reduction of the initial or subsequent tapering dose can occur every 3 weeks. In other exemplary embodiments, a reduction of the initial or subsequent tapering dose can occur every 2 weeks. In other exemplary embodiments, a reduction of the initial or subsequent tapering dose can occur every week. In certain embodiments, the tapering of corticosteroids can comprise a reduction of about 0.5 mg prednisone/kg/day or equivalent about every week, about every two weeks or about every month. In certain embodiments, the tapering of corticosteroids can comprise a reduction of about 0.25 mg prednisone/kg/day or equivalent about every week, about every two weeks or about every month. In certain embodiments, the tapering of corticosteroids can comprise a reduction of about 0.1 mg prednisone/kg/day or equivalent about every week, about every two weeks or about every month.

In accordance with each of the foregoing aspects:

In exemplary embodiments, the FcRn antagonist is capable of binding to FcRn and preventing IgG recycling and/or causing a decrease in IgG level. In certain embodiments, the FcRn antagonist consists of a variant Fc region or domain and lacks an antigen binding site. In certain other embodiments, the FcRn antagonist is an antibody or antigen-binding fragment thereof that binds specifically to FcRn and inhibits binding of immunoglobulin to FcRn.

In certain embodiments, the FcRn antagonist is a human IgG1 antibody Fc fragment that has been engineered for increased affinity to FcRn. In certain exemplary embodiments, the FcRn antagonist consists of a variant Fc region. In certain exemplary embodiments, the variant Fc region consists of two Fc domains which form a homodimer, wherein the amino acid sequence of each of the Fc domains is selected from the group consisting of SEQ ID NO: 1, SEQ ID NO: 2, and SEQ ID NO: 3. In some embodiments, the amino acid sequence of each of the Fc domains is SEQ ID NO: 1. In some embodiments, the amino acid sequence of each of the Fc domains is SEQ ID NO: 2. In some embodiments, the amino acid sequence of each of the Fc domains is SEQ ID NO: 3.

In certain exemplary embodiments, the FcRn antagonist is efgartigimod.

In certain embodiments, the FcRn antagonist is an antibody or antigen-binding fragment thereof that binds specifically to FcRn and inhibits binding of immunoglobulin to FcRn. In certain embodiments, the FcRn antibody or antigen-binding fragment thereof is a humanized IgG4 antibody (e.g., rozanolixizumab or orilanolimab). In other embodiments, the FcRn antibody or antigen-binding fragment thereof is a humanized IgG1 antibody (e.g., nipocalimab or batoclimab).

In some embodiments, the pemphigus comprises pemphigus vulgaris (PV), pemphigus foliaceus (PF), or both PV and PF. In some embodiments, the pemphigus comprises pemphigus vulgaris (PV). In some embodiments, the pemphigus comprises pemphigus foliaceus (PF). In some embodiments, the pemphigus comprises both pemphigus vulgaris (PV) and pemphigus foliaceus (PF). In some embodiments, the pemphigus consists of pemphigus vulgaris (PV). In some embodiments, the pemphigus consists of pemphigus foliaceus (PF). In some embodiments, the pemphigus consists of both pemphigus vulgaris (PV) and pemphigus foliaceus (PF).

In certain embodiments, the pemphigus vulgaris (PV) is of the mucosal-dominant subtype. In certain embodiments, the pemphigus vulgaris (PV) is of the mucocutaneous subtype. In certain embodiments, the pemphigus vulgaris (PV) is of the cutaneous subtype.

In some embodiments, the subject has mild, moderate, or severe pemphigus as classified by Pemphigus Disease Area Index (PDAI).

In some embodiments, the subject has mild pemphigus as classified by PDAI. In exemplary embodiments, the pemphigus or pemphigus-related disorder is characterized by a PDAI score of less than 15.

In some embodiments, the subject has moderate pemphigus as classified by PDAI. In certain embodiments, the pemphigus-related disorder is moderate to severe pemphigus as classified by PDAI. In some embodiments, the subject suffering from pemphigus has a PDAI score≥15 and <45.

In some embodiments, the subject has severe pemphigus. In exemplary embodiments, the subject suffering from severe pemphigus has a PDAI score≥45.

In some embodiments, the subject has refractory pemphigus.

In certain embodiments, the pemphigus is newly diagnosed. In other embodiments, the pemphigus is relapsing pemphigus.

In certain embodiments, the FcRn antagonist is administered to the subject intravenously.

In certain embodiments, the FcRn antagonist is administered to the subject subcutaneously. In certain embodiments, the FcRn antagonist is co-formulated with hyaluronidase and administered subcutaneously.

In some embodiments, the FcRn antagonist is administered once weekly or more frequently (e.g., every 1, 2, 3, 4, 5, 6, or 7 days) until disease control.

In some embodiments, the FcRn antagonist is administered less frequently than once weekly (e.g., every 8, 9, 10, 11, 12, 13, or 14 days; or every 2, 3, 4, 5, 6 weeks) until disease control.

In some embodiments, the FcRn antagonist is administered once weekly or biweekly at a dose of about 10 mg/kg or about 25 mg/kg until disease control.

In some embodiments, the FcRn antagonist is co-administered with a corticosteroid dose of 10 mg/day or less.

In some embodiments, the method further comprises administering a tapering dose of corticosteroid beginning at ≤2 mg prednisone/kg/day or equivalent, more preferably beginning at ≤1.5 mg prednisone/kg/day or equivalent, even more preferably beginning at ≤ 1 mg prednisone/kg/day or equivalent or at ≤0.5 mg prednisone/kg/day or equivalent. In certain embodiments, the tapering dose of corticosteroid is administered after disease control has been achieved.

In some embodiments, the corticosteroid is administered systemically.

In some embodiments, disease control is obtained without co-administering corticosteroids. In some embodiments, disease control is obtained without co-administering prednisone.

In some embodiments, the FcRn antagonist is administered once weekly or more frequently (e.g., every 1, 2, 3, 4, 5, 6, or 7 days) until complete remission (e.g., a PDAI score of 0).

In some embodiments, the FcRn antagonist is administered once weekly or biweekly at a dose of about 10 mg/kg or about 25 mg/kg until complete remission (e.g., a PDAI score of 0).

In some embodiments, the FcRn antagonist is administered less frequently than once weekly (e.g., every 8, 9, 10, 11, 12, 13, or 14 days; or every 2, 3, 4, 5, or 6 weeks) until complete remission (e.g., a PDAI score of 0).

In some embodiments, complete remission is obtained with a corticosteroid dose of 20 mg/day or less.

In some embodiments, complete remission is obtained with a corticosteroid dose of 10 mg/day or less.

In some embodiments, complete remission is obtained without co-administering corticosteroids.

In some embodiments, a tapering dose of corticosteroid is administered after disease control or complete remission has been achieved.

In some embodiments, the FcRn antagonist is administered intravenously.

In some embodiments, the FcRn antagonist is administered intravenously once weekly.

In some embodiments, the FcRn antagonist is administered intravenously every two weeks.

In some embodiments, the FcRn antagonist is administered intravenously at a dose of 10 mg/kg to 30 mg/kg.

In some embodiments, the FcRn antagonist is administered intravenously at a dose of 10 mg/kg.

In some embodiments, the FcRn antagonist is administered intravenously at a dose of 25 mg/kg.

In some embodiments, the FcRn antagonist is administered subcutaneously.

In some embodiments, the FcRn antagonist is administered subcutaneously once weekly.

In some embodiments, the FcRn antagonist is administered subcutaneously every two weeks.

In some embodiments, the FcRn antagonist is co-formulated with hyaluronidase and administered subcutaneously.

In some embodiments, the FcRn antagonist is administered subcutaneously at a fixed dose of about 750 mg to about 3000 mg. In some embodiments, the FcRn antagonist is administered subcutaneously at a fixed dose of about 1000 mg or about 2000 mg. In some embodiments, the FcRn antagonist is administered subcutaneously at a fixed dose of about 1000 mg twice on the same day.

In some embodiments, the FcRn antagonist is administered subcutaneously once weekly or more frequently (e.g., every 1, 2, 3, 4, 5, 6, or 7 days) at a fixed dose of about 750 mg to about 1750 mg. In some embodiments, the FcRn antagonist is administered subcutaneously once weekly or more frequently (e.g., every 1, 2, 3, 4, 5, 6, or 7 days) at a fixed dose of about 1000 mg. In some embodiments, the FcRn antagonist is administered subcutaneously once weekly or more frequently (e.g., every 1, 2, 3, 4, 5, 6, or 7 days) at a dose of about 10 mg/kg to about 25 mg/kg. In some embodiments, the FcRn antagonist is administered subcutaneously once weekly or more frequently (e.g., every 1, 2, 3, 4, 5, 6, or 7 days) at a dose of about 10 mg/kg. In some embodiments, the FcRn antagonist is administered subcutaneously once weekly or more frequently (e.g., every 1, 2, 3, 4, 5, 6, or 7 days) at a dose of about 25 mg/kg.

In some embodiments, the FcRn antagonist is first administered subcutaneously at a fixed dose of about 1000 mg twice on the same day.

In some embodiments, the FcRn antagonist is administered in an induction phase and a consolidation phase.

In some embodiments, the FcRn antagonist is administered in an induction phase and a consolidation phase, wherein
  (i) during the induction phase the FcRn antagonist is administered once weekly or biweekly and corticosteroid 0.5 mg prednisone/kg/day or equivalent is administered until disease control, and
  (ii) during the consolidation phase the FcRn antagonist dose is reduced or the FcRn antagonist dosing interval is lengthened, and/or the corticosteroid dose is decreased or the corticosteroid dosing interval is lengthened, to an end-of-consolidation dose or dosing interval effective to prevent new lesions from appearing.

In some embodiments, during the induction phase, the FcRn antagonist dosing interval is once weekly or more frequently (e.g., a dosing interval of every 1, 2, 3, 4, 5, 6 or 7 days). In some embodiments, during the induction phase, the FcRn antagonist is administered subcutaneously at a fixed dose of about 750 mg to about 1750 mg. In some embodiments, during the induction phase, the FcRn antagonist is administered subcutaneously at a fixed dose of about 1000 mg. In some embodiments, during the induction phase, the FcRn antagonist is administered subcutaneously at a dose of about 10 mg/kg to about 25 mg/kg. In some embodiments, during the induction phase, the FcRn antagonist is administered subcutaneously at a dose of about 10 mg/kg. In some embodiments, during the induction phase, the FcRn antagonist is administered subcutaneously at a dose of about 25 mg/kg.

In some embodiments, during the induction phase, the FcRn antagonist is first administered subcutaneously at a fixed dose of about 1000 mg twice on the same day.

In some embodiments, during the consolidation phase, the FcRn antagonist dosing interval is once weekly or more frequently (e.g., a dosing interval of every 1, 2, 3, 4, 5, 6, or 7 days). In some embodiments, during the consolidation phase, the FcRn antagonist is administered less frequently than once weekly (e.g., a dosing interval of every 8, 9, 10, 11, 12, 13, or 14 days; or a dosing interval of every 2, 3, or 4 weeks) until disease control. In some embodiments, during the consolidation phase, the FcRn antagonist dosing interval is once weekly or every 2 weeks.

In some embodiments, the method comprises an induction phase and a consolidation phase, wherein (i) during the induction phase the FcRn antagonist is administered once weekly and with a corticosteroid dose of 2 mg/kg/day or less (e.g., 0.5 mg prednisone/kg/day or equivalent) until disease control, and (ii) during the consolidation phase the FcRn antagonist dose is decreased or the FcRn antagonist dosing interval is lengthened, and/or the corticosteroid dose is decreased or the corticosteroid dosing interval is lengthened, to an end-of-consolidation dose or dosing interval effective to prevent new lesions from appearing.

In some embodiments, the method further comprises a maintenance phase, wherein (iii) during the maintenance phase the end-of-consolidation dose or dosing interval for the FcRn antagonist and/or the prednisone is continued until complete clearance of lesions. In some embodiments, during the maintenance phase the FcRn antagonist dosing interval is once weekly or more frequently (e.g., a dosing interval of every 1, 2, 3, 4, 5, 6, or 7 days). In some embodiments, during the maintenance phase the FcRn antagonist dosing interval is once weekly. In some embodiments, during the maintenance phase the FcRn antagonist dosing interval is less frequent than once weekly (e.g., a dosing interval of every 8, 9, 10, 11, 12, 13, or 14 days; or a dosing interval of every 2, 3, 4, 5, or 6 weeks). In some embodiments, during the maintenance phase the FcRn antagonist dosing interval is biweekly.

In some embodiments, during the induction phase the FcRn antagonist is administered intravenously at a dose of 10 mg/kg to 30 mg/kg. In some embodiments, during the induction phase the FcRn antagonist is administered intravenously at a dose of 10 mg/kg. In some embodiments, during the induction phase the FcRn antagonist is administered intravenously at a dose of 25 mg/kg.

In some embodiments, during the induction phase the FcRn antagonist is administered subcutaneously at a fixed dose of 750 mg to 3000 mg. In some embodiments, during the induction phase the FcRn antagonist is administered subcutaneously at a fixed dose of 1000 mg or 2000 mg. In some embodiments, during the induction phase the FcRn antagonist is first administered subcutaneously at a fixed dose of about 1000 mg twice on the same day.

In some embodiments, during the consolidation phase the FcRn antagonist dosing interval is once weekly, every 2 weeks or less frequently.

In some embodiments, during the maintenance phase the FcRn antagonist dosing interval is once weekly, every 2 weeks, every 4 weeks, or less frequently.

In some embodiments, the pemphigus goes into complete remission following treatment with FcRn antagonist. In some embodiments, the complete remission is achieved with a corticosteroid dose of 2 mg prednisone/kg/day (or equivalent) or less. In some embodiments, the complete remission is achieved with a corticosteroid dose of 1 mg prednisone/kg/day (or equivalent) or less. In some embodiments, the complete remission is achieved with a corticosteroid dose of ≤about 0.5 mg prednisone/kg/day or equivalent. In some embodiments, the complete remission is achieved at a corticosteroid dose of ≤about 0.3 mg prednisone/kg/day or equivalent. In some embodiments, the complete remission is achieved at a corticosteroid dose of ≤about 0.2 mg prednisone/kg/day or equivalent. In some embodiments, the complete remission is achieved at a corticosteroid dose of ≤about 0.1 mg prednisone/kg/day or equivalent. In some embodiments, the complete remission is achieved at a corticosteroid dose of ≤about 0.2 mg prednisone/kg/day or equivalent to about 0.50 mg prednisone/kg/day or equivalent.

In some embodiments, the complete remission is achieved with a corticosteroid dose of about 20 mg prednisone/day (or equivalent) or less. In some embodiments, the complete remission is achieved with a corticosteroid dose of about 15 mg prednisone/day (or equivalent) or less. In some embodiments, the complete remission is achieved with a corticosteroid dose of about 10 mg prednisone/day (or equivalent) or less (e.g., about 10, about 9, about 8, about 7, or about 6 prednisone/day (or equivalent)). In some embodiments, the complete remission is achieved with a corticosteroid dose of about 5 mg prednisone/day (or equivalent) or less (e.g., about 5, about 4, about 3, about 2, about 1, or about 0.5 mg prednisone/day (or equivalent)).

In some embodiments, the complete remission is achieved without corticosteroid.

In some embodiments, the complete remission is maintained with a corticosteroid dose of ≤about 0.5 mg prednisone/kg/day or equivalent. In some embodiments, the complete remission is maintained with a corticosteroid dose of ≤about 0.4 mg prednisone/kg/day or equivalent. In some embodiments, the complete remission is maintained with a corticosteroid dose of ≤about 0.3 mg prednisone/kg/day or equivalent. In some embodiments, the complete remission is maintained with a corticosteroid dose of ≤about 0.2 mg prednisone/kg/day or equivalent. In some embodiments, the complete remission is maintained with a corticosteroid dose of ≤about 0.1 mg prednisone/kg/day or equivalent.

In some embodiments, the complete remission is maintained with a corticosteroid dose of ≤about 10 mg prednisone/day or equivalent (e.g., about 10 mg, about 9 mg, about 8 mg, about 7 mg, or about 6 mg prednisone/day (or equivalent)). In some embodiments, the complete remission is maintained with a corticosteroid dose of ≤about 5 mg prednisone/day or equivalent (e.g., about 5 mg, about 4 mg, about 3 mg, or about 2 mg prednisone/day (or equivalent)). In some embodiments, the complete remission is maintained with a corticosteroid dose of ≤about 2 mg prednisone/day or equivalent. In some embodiments, the complete remission is maintained without corticosteroid.

In some embodiments, the subject has refractory pemphigus.

In some embodiments, the subject is rituximab-refractory.

In some embodiments, the subject is corticosteroid-intolerant.

In some embodiments, the method further comprises administering a B-cell depleting agent (e.g., rituximab) to the subject.

BRIEF DESCRIPTION OF THE DRAWINGS

FIG. 4A, cohort 1; FIG. 4B, cohort 2; FIG. 4C, cohort 3; and FIG. 4D, cohort 4.

Most patients demonstrated strong PDAI score improvements: In cohort 1 there was a correlation in IgG reduction with anti-Dsg reduction with PDAI score improvement, early DC (mono/combo) and suboptimal efgartigimod dosing in maintenance; in cohort 2 there was improved maintenance with efgartigimod dosing every other week. In cohort 3 all patients ultimately associated with prednisone, maintenance further improved symptoms, and EoC/CR (end of consolidation/complete remission) was noted when associated with oral prednisone. In cohort 4, strong PDAI score improvements were noted, there was a high rate of EoC, and CR when prednisone was not tapered before CR.

Figure 5A:
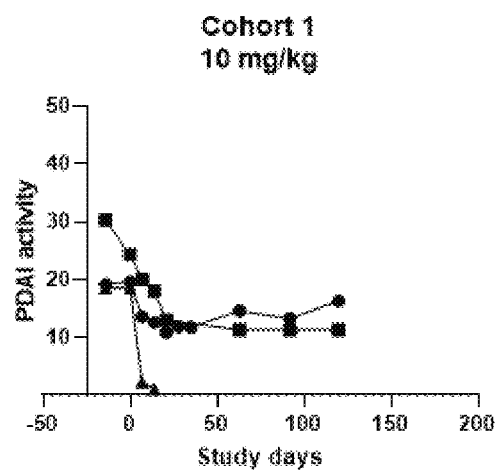
Figure 5B:
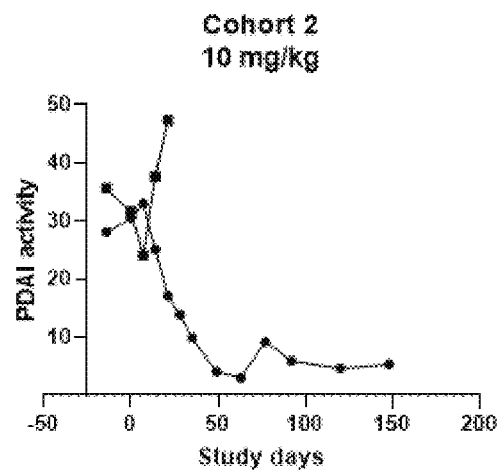
Figure 5C:
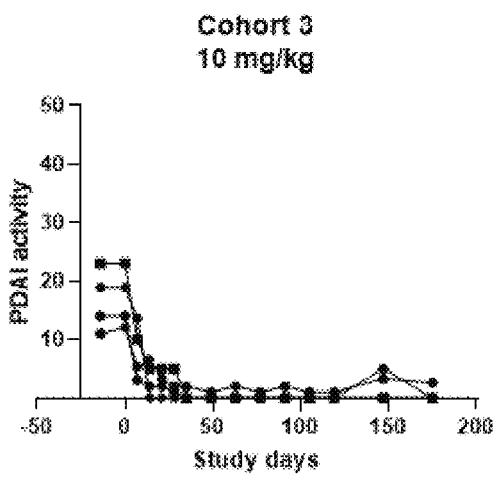
Figure 5D:
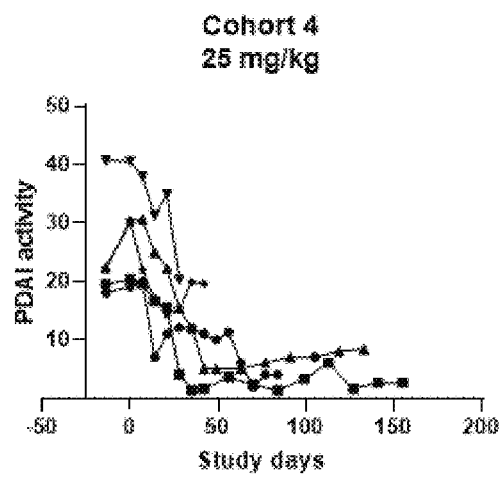
Figure 6A:
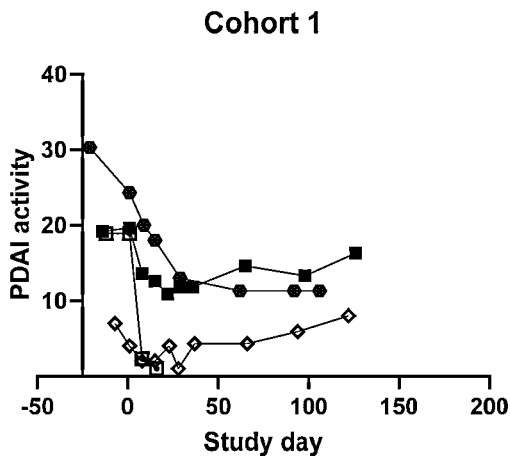
Figure 6B:
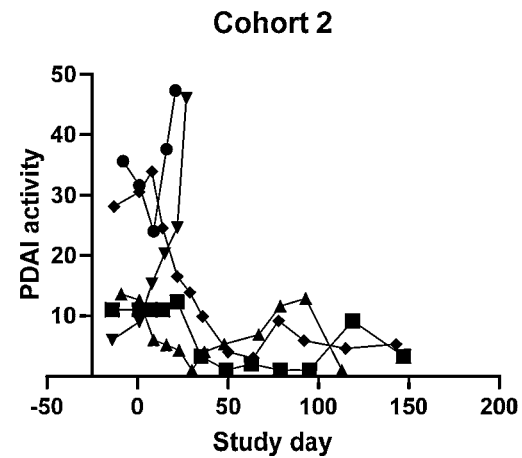
Figure 6C:
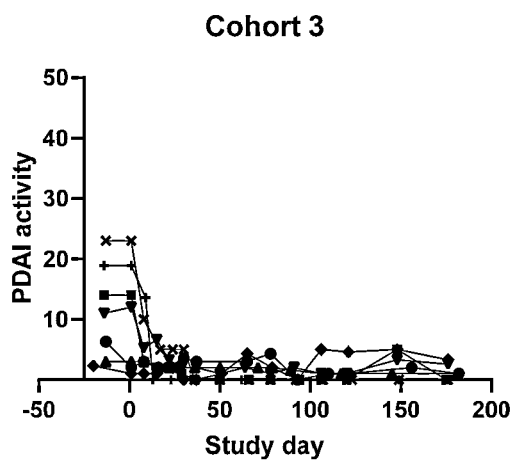
Figure 6D:
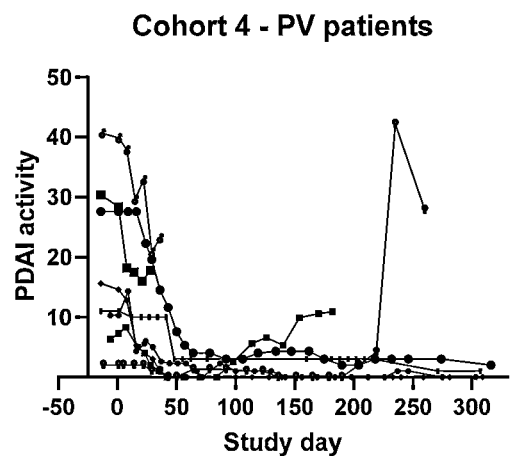
Figure 6E:
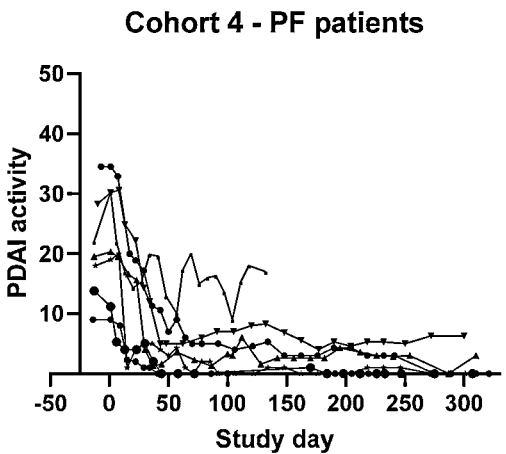

FIGS. 5A-5D depict clinical efficacy in moderate severity patients of the Phase 2 trial (PDAI 15-44 at baseline). FIG. 5A, cohort 1; FIG. 5B, cohort 2, FIG. 5C, cohort 3; FIG. 5D, cohort 4. Most patients demonstrated strong PDAI score improvements: cohort 1 comprised three moderate patients (3 PV, 0 pemphigus foliaceus (PF)); cohort 2 comprised two moderate patients (2 PV, 0 PF); cohort 3 comprised four moderate patients (4 PV, 0 PF); and cohort 4 comprised five moderate patients (1 PV, 4 PF). Data is from initial interim results in 1701 study of efgartigimod in pemphigus patients. Cut-off date on the data from the Phase 2 trial is: 7 Nov. 2019.

FIGS. 6A-6E are graphs depicting PDAI activity scores over time in A) cohort 1, B) cohort 2, C) cohort 3, D) cohort 4 pemphigus vulgaris patients, E) cohort 4 pemphigus foliaceus patients. Data is from final results in the Phase 2 trial (1701 study) of efgartigimod in pemphigus patients. Cut-off date on the data from the Phase 2 trial is: 28 Oct. 2020.

Figure 7A:
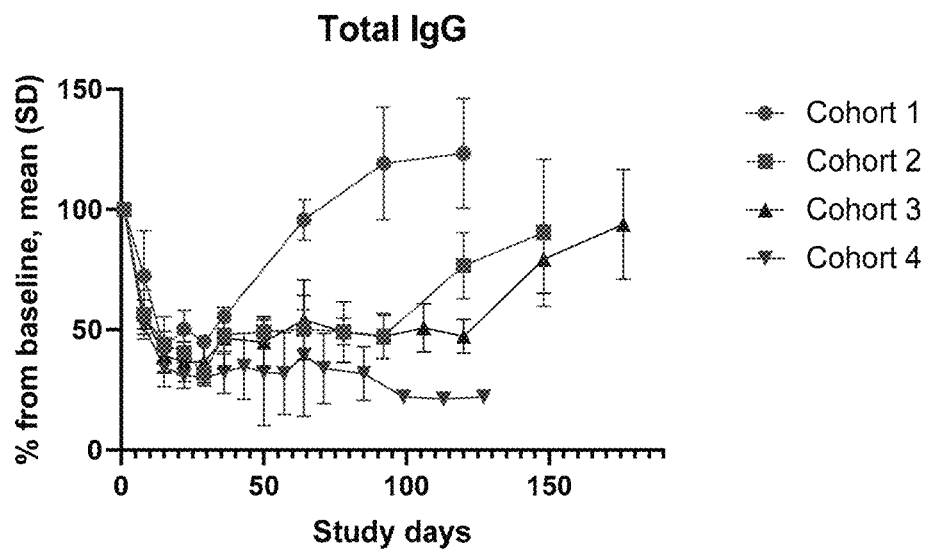
Figure 7B:
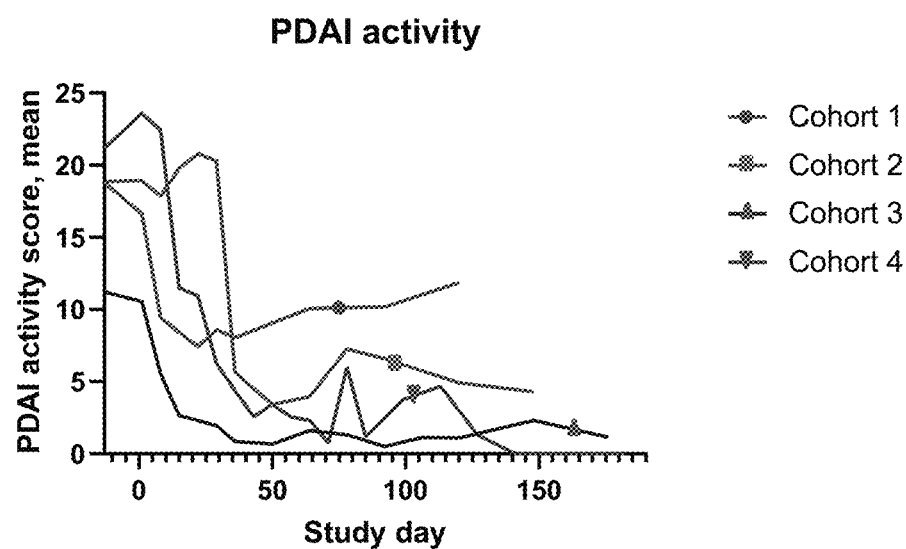

FIGS. 7A and 7B depict the clinical efficacy as assessed by the total IgG (FIG. 7A) and PDAI activity (FIG. 7B) per cohort. There is a correlation between IgG reduction, autoantibody reductions, and PDAI score improvements. Patients in cohorts 1 and 2 were treated with efgartigimod monotherapy or in combination with prednisone. All patients in cohort 3 were ultimately associated with prednisone. Patients in cohort 4 were being treated in combination with prednisone per protocol. Data is from initial interim results of the Phase 2 trial (1701 study) of efgartigimod in pemphigus patients. Cut-off date on the data from the Phase 2 trial is: 7 Nov. 2019. FU, follow-up.

Figure 8A:
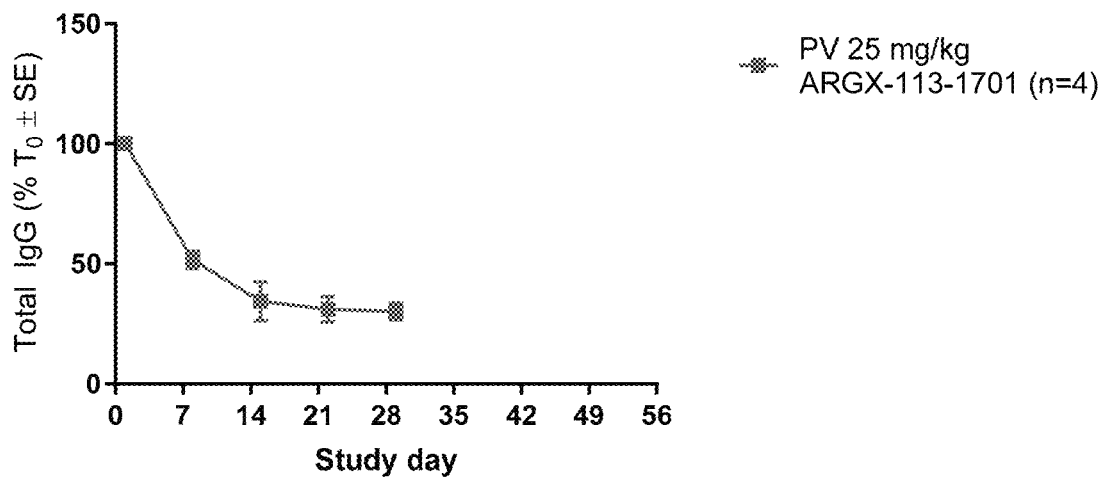
Figure 8B:
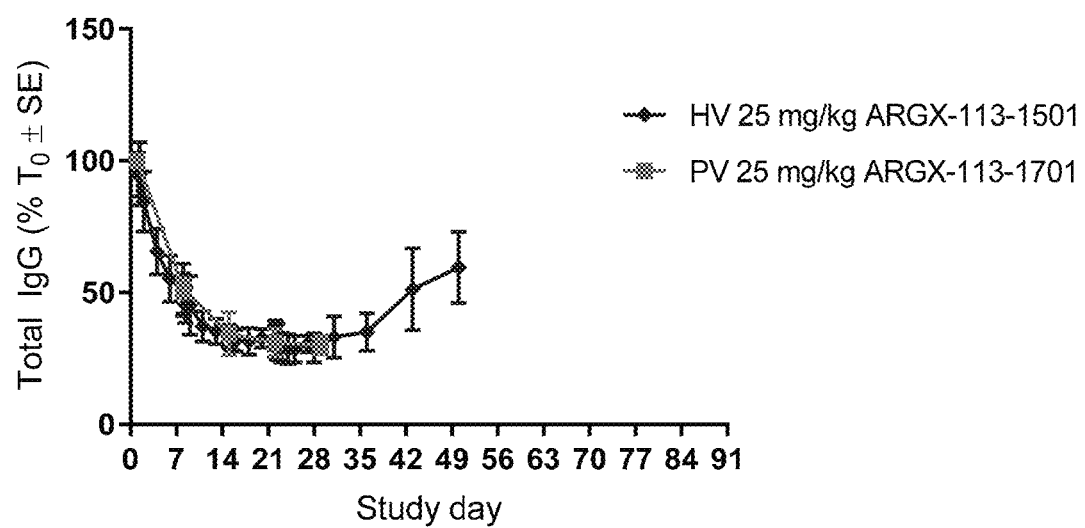

FIGS. 8A and 8B depict pharmacodynamic (PD) data for the reduction of total IgG in the Phase 2 trial (1701 study) of efgartigimod in pemphigus patients. PD profiles are shown for four weekly administrations of efgartigimod at 25 mg/kg. FIG. 8A, PD profile in PV. FIG. 8B, PD profiles in healthy volunteers (HV) and pemphigus vulgaris patients (PV). Similar P D profiles were observed between PV and HV, in line with expectations based on HV and modeling. Data is from initial interim results of the trial. Cut-off date on the data from the Phase 2 trial is: 7 Nov. 2019.

Figure 9A:
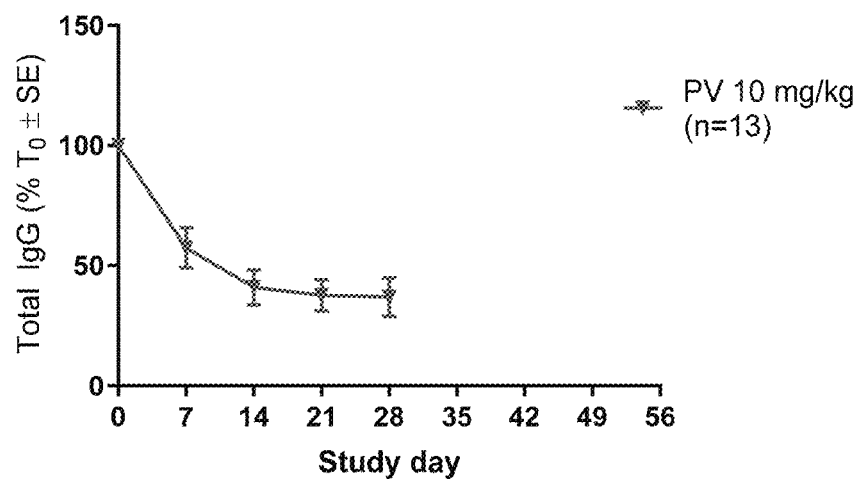
Figure 9B:
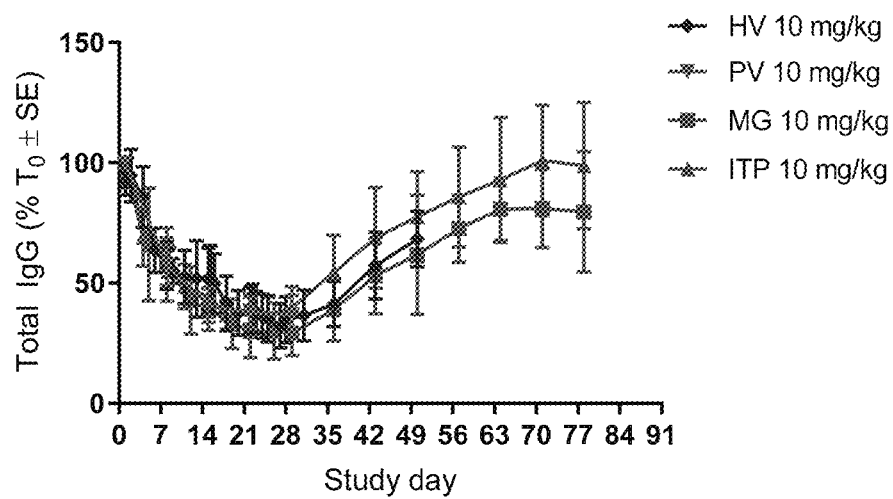

FIGS. 9A and 9B depict pharmacodynamic (PD) data for the reduction of total IgG in PV, healthy volunteers (HV), and other indications. PD profiles are shown for four weekly administrations of efgartigimod at 10 mg/kg. FIG. 9A, PD profile in PV. FIG. 9B, PD profiles in HV, PV, myasthenia gravis (MG) and immune thrombocytopenia (ITP). Data is from initial interim results of the Phase 2 trial (1701 study) of efgartigimod in pemphigus patients. Cut-off date on the data from the Phase 2 trial is: 7 Nov. 2019.

Figure 10A:
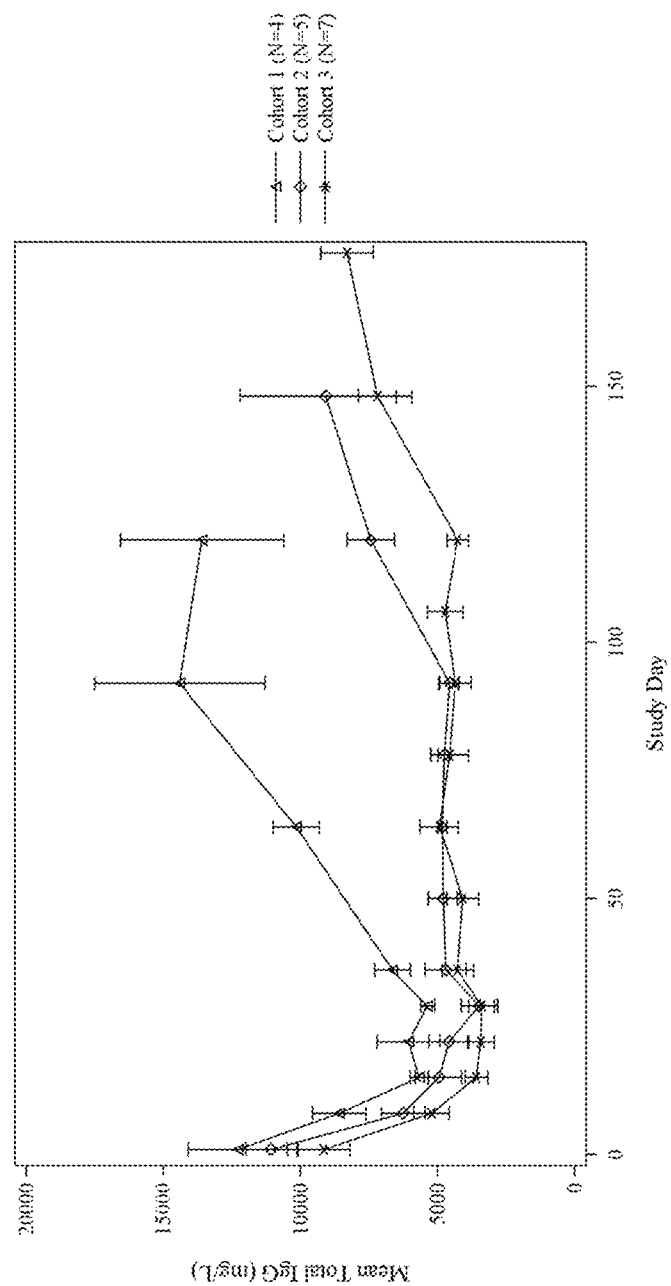
Figure 10B:
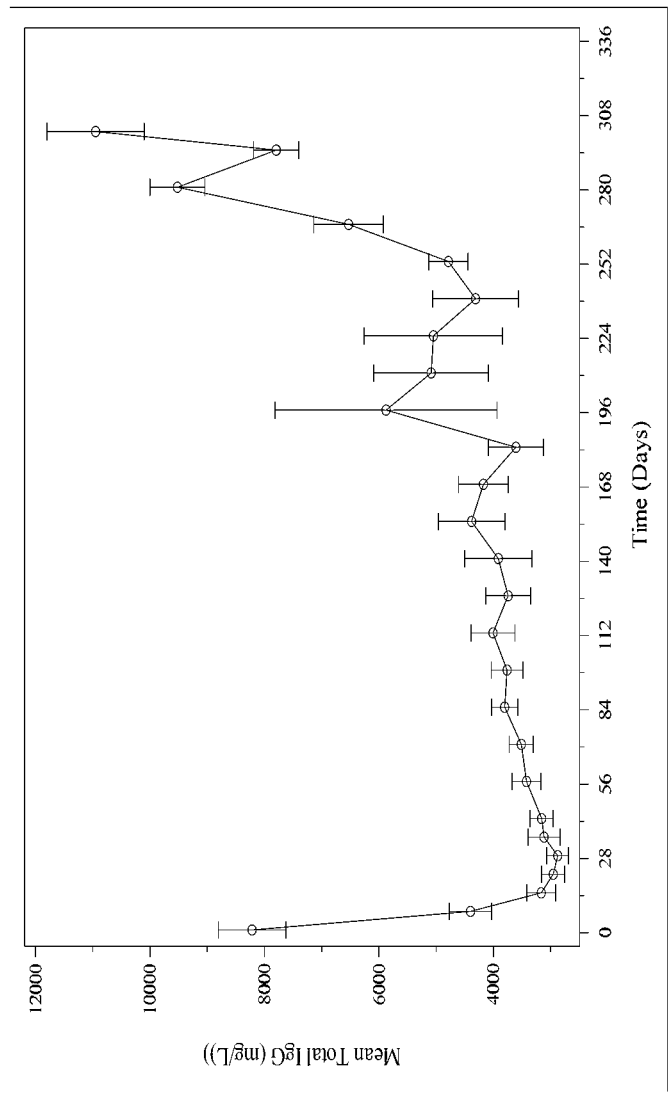
Figure 11A:
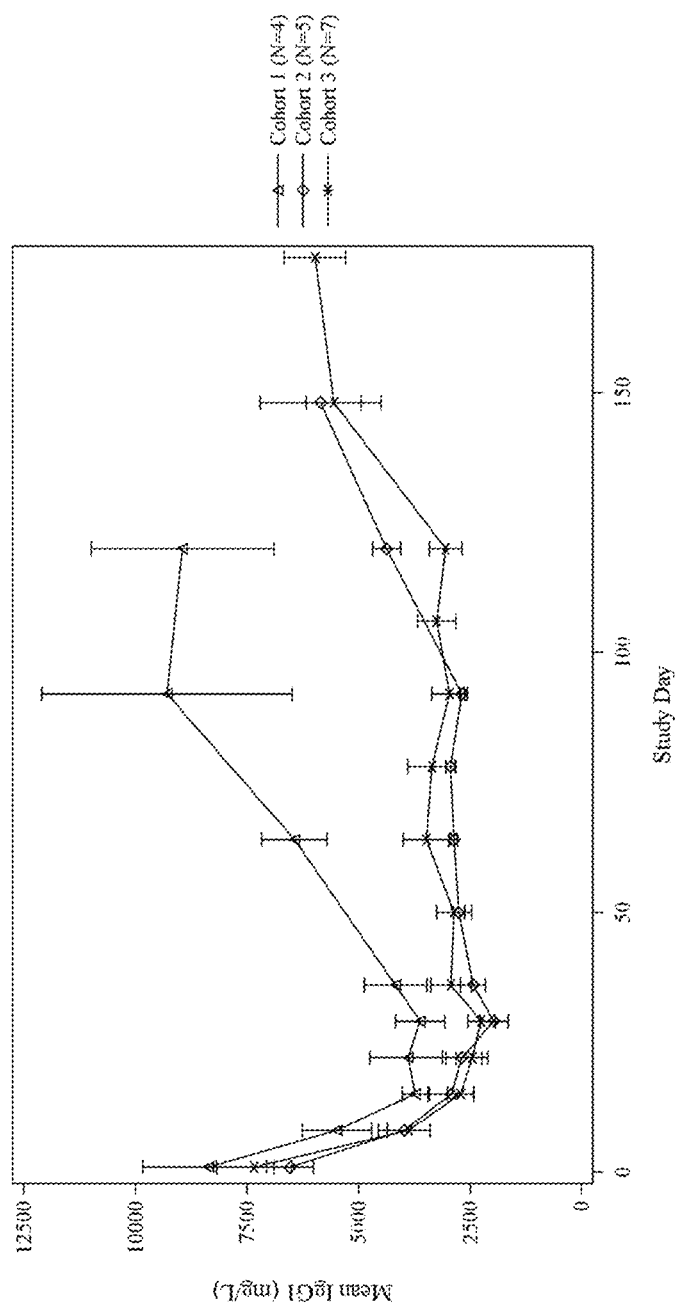
Figure 11B:
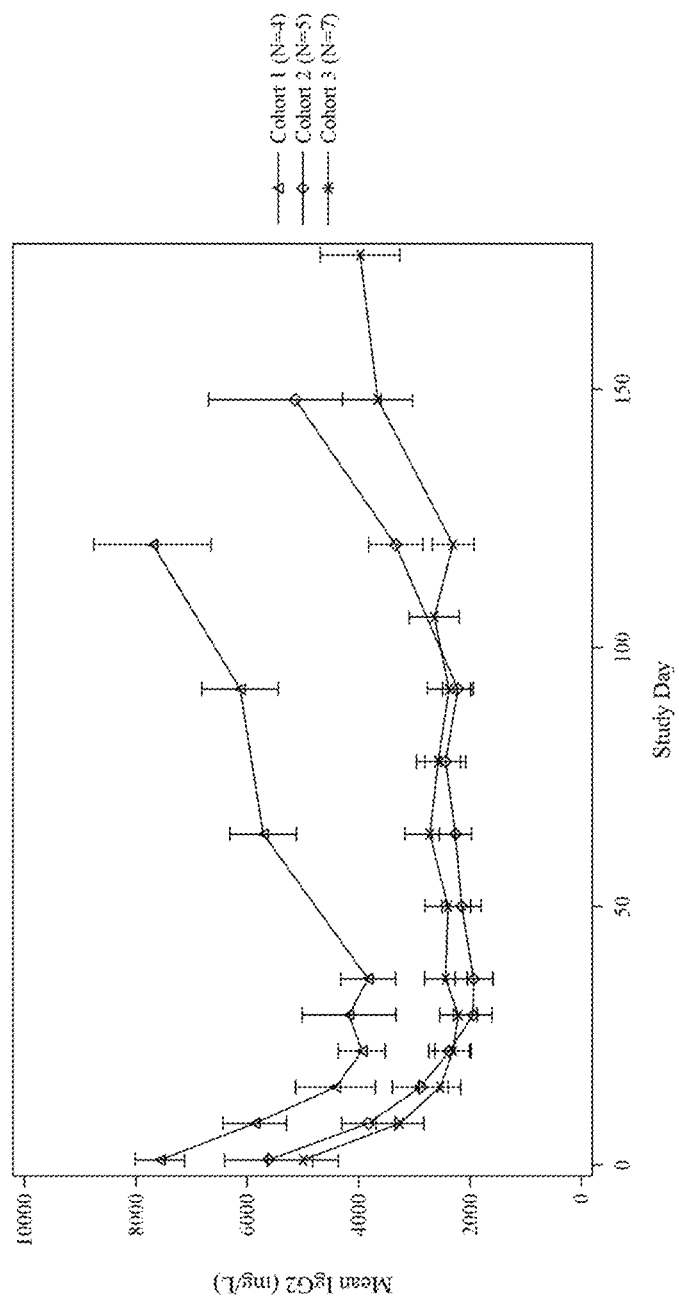
Figure 11C:
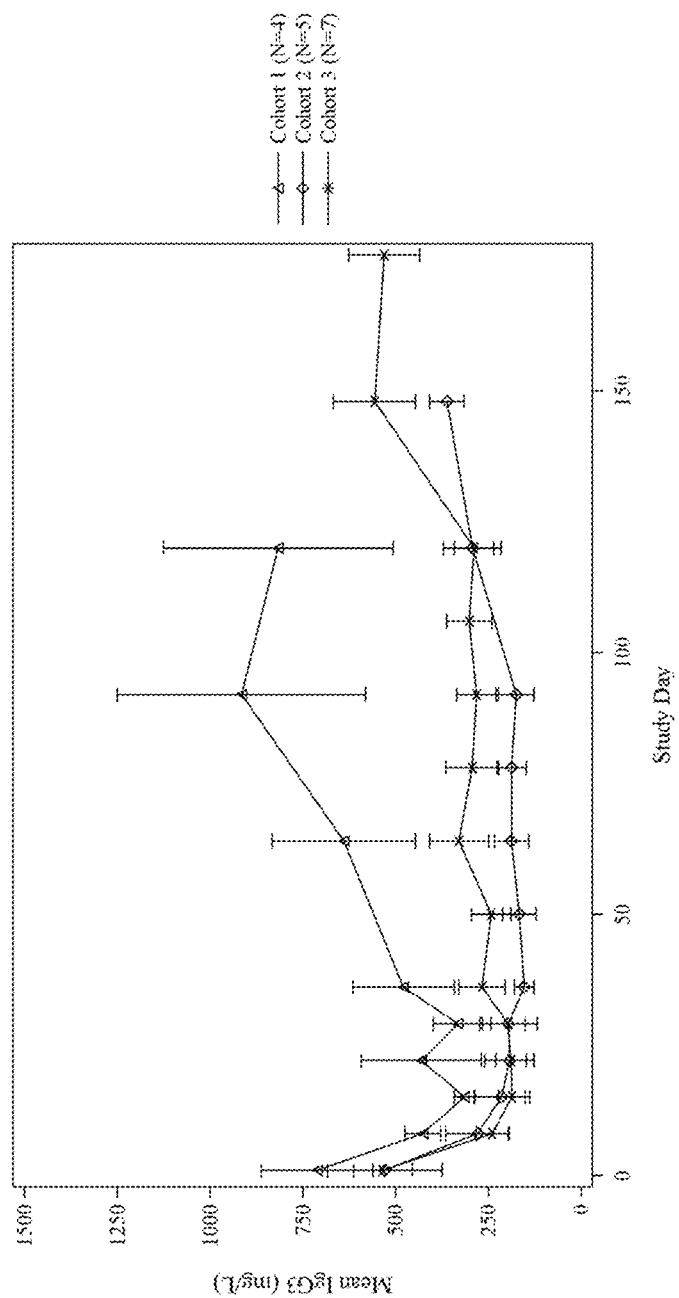
Figure 11D:
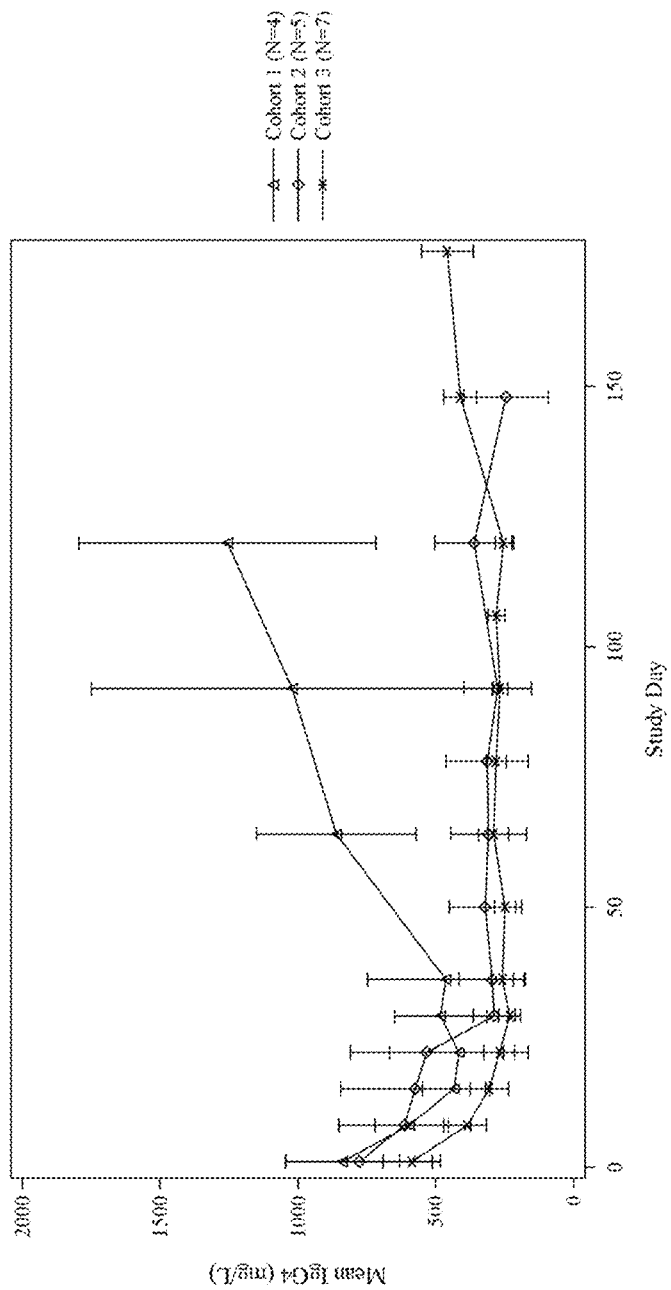
Figure 11E:
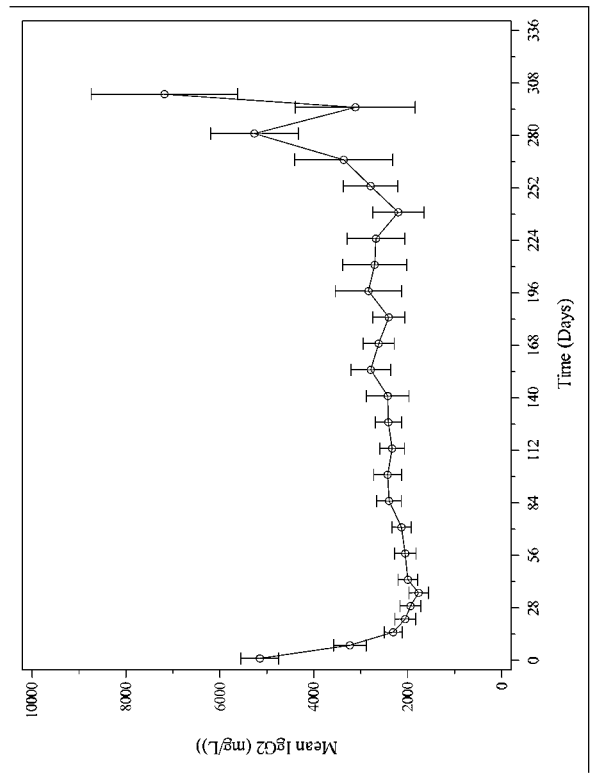
Figure 11F:
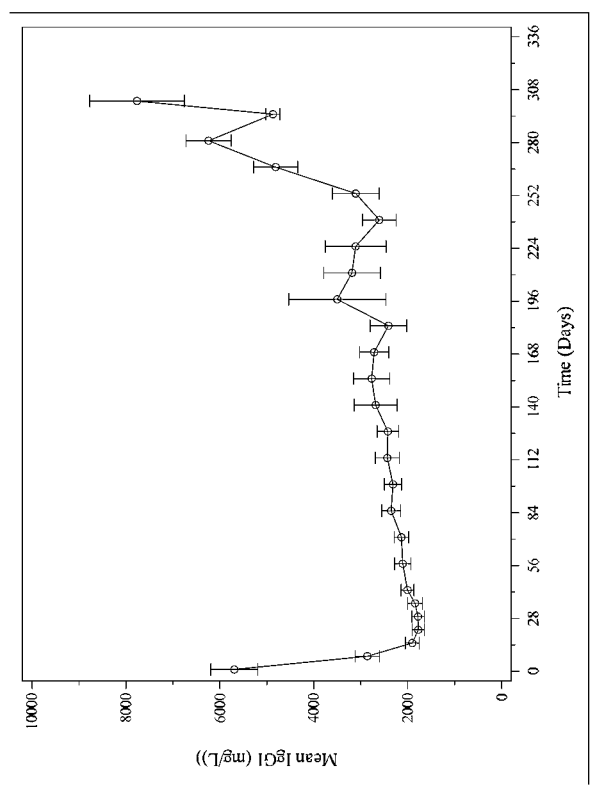
Figure 11G:
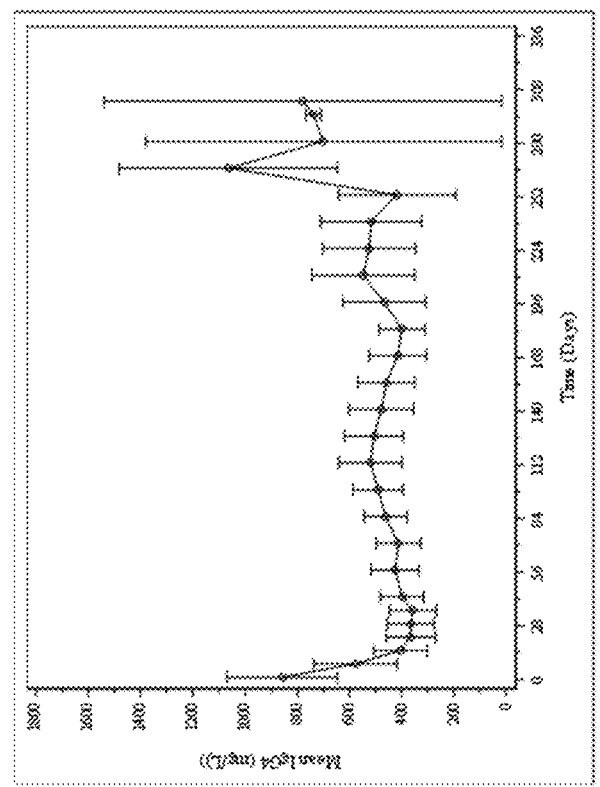
Figure 11H:
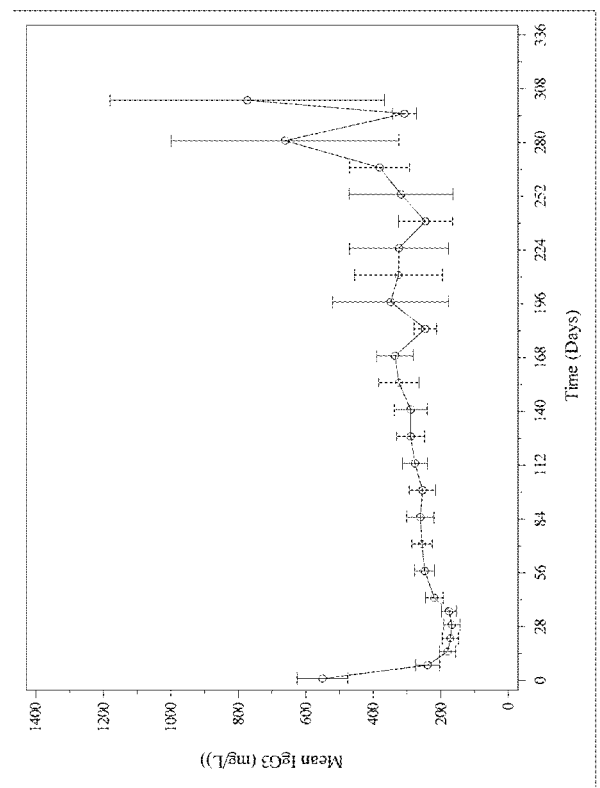
Figure 12A:
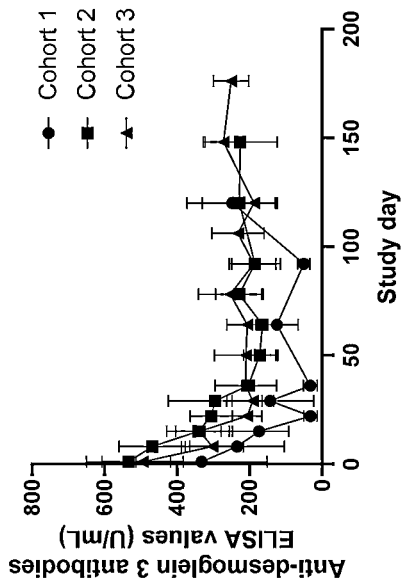
Figure 12B:
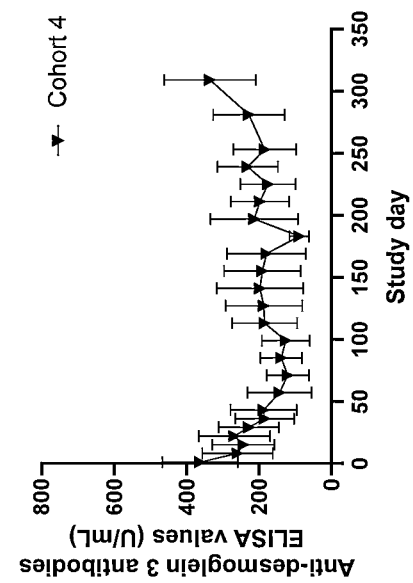
Figure 12C:
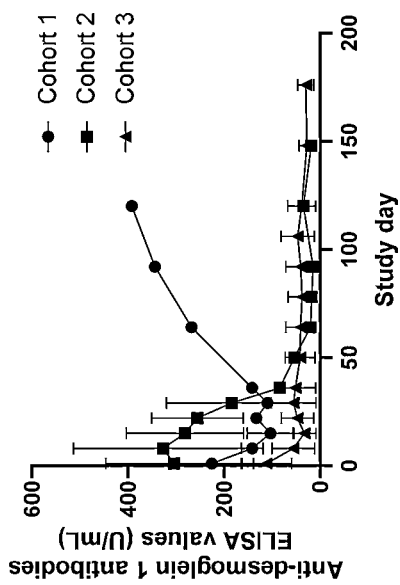
Figure 12D:
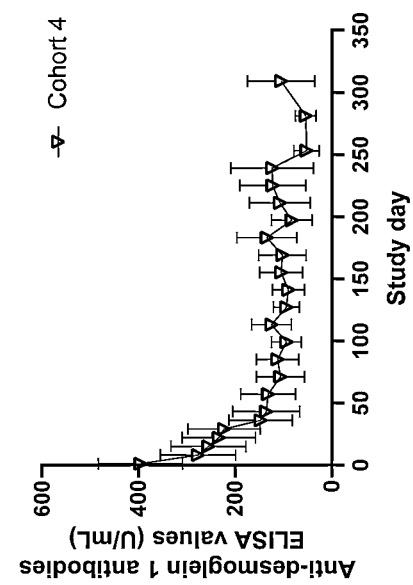

FIGS. 10A and 10B depict serum levels of total IgG in A) cohort 1-3, B) cohort 4. Data is from final results of the Phase 2 trial (1701 study) of efgartigimod in pemphigus patients. Cut-off date on the data from the Phase 2 trial is: 24 Jun. 2020.

FIGS. 11A-11H depict serum levels of IgG subclasses IgG1, IgG2, IgG3, and IgG4 in cohorts 1-3 (A-D) and in cohort 4 (E-H). Data is from final results of the Phase 2 trial (1701 study) of efgartigimod in pemphigus patients. Cut-off date on the data from the Phase 2 trial is: 24 Jun. 2020.

FIGS. 12A-12D depict serum levels of anti-desmoglein 1 autoantibodies in cohorts 1-3 (FIG. 12A) and cohort 4 (FIG. 12B) and anti-desmoglein 3 autoantibodies in cohorts 1-3

(FIG. 12C) and cohort 4 (FIG. 12D), over time. Data is from final results of Phase 2 trial (1701 study) of efgartigimod in pemphigus patients.

Figure 13:
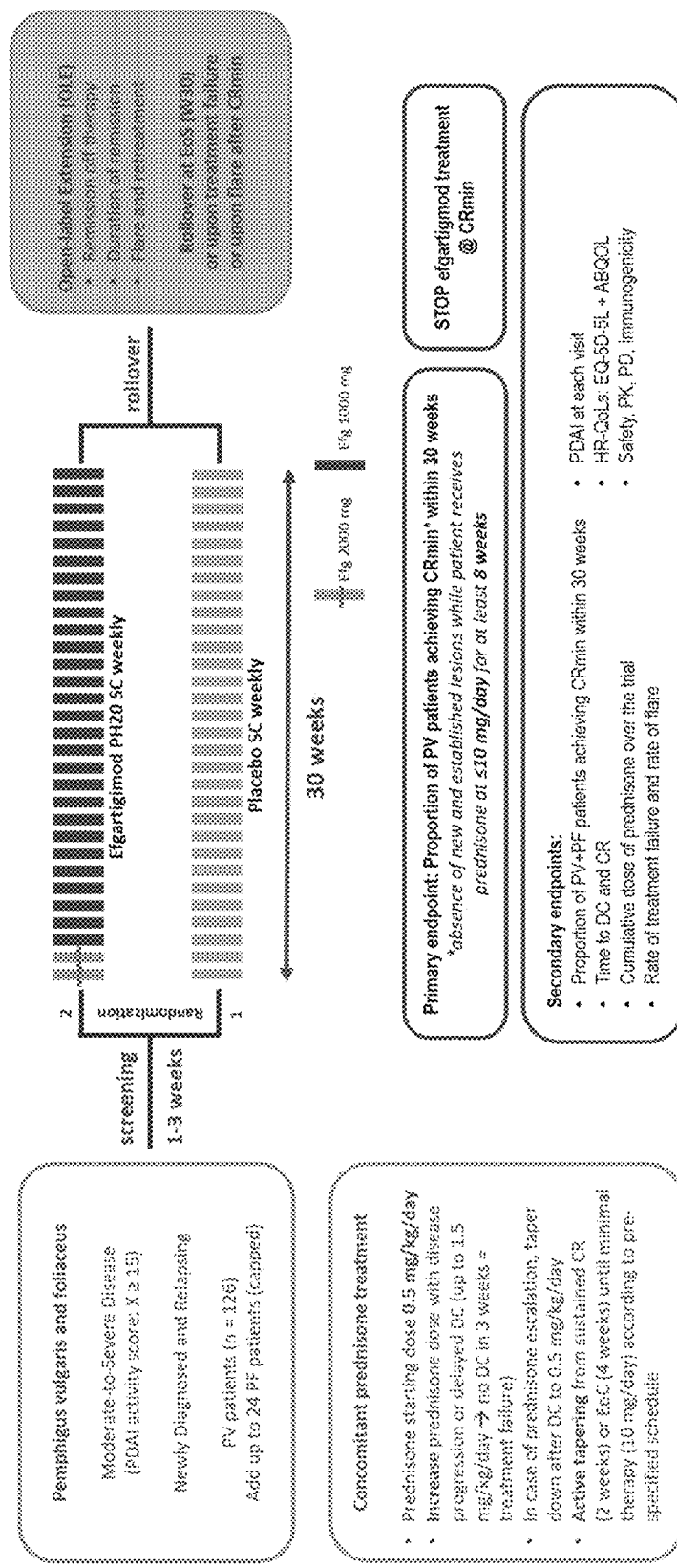

FIG. 13 is a diagram outlining the design of the Phase 3 clinical trial described in Example 13. ABQOL=Autoimmune Bullous Disease Quality of Life; CR=complete clinical remission; CRmin-complete remission on minimal therapy; DC-disease control; Efg-efgartigimod PH20 SC; EoC=end of consolidation; EoS=end of study; EQ-5D-5L=EuroQol 5-dimension 5-level; OLE=open-label extension; PD-pharmacodynamics; PDAI=Pemphigus Disease Area Index; PF-pemphigus foliaceus; PK-pharmacokinetics; PV=pemphigus vulgaris; SC=subcutaneous.

Figure 14:
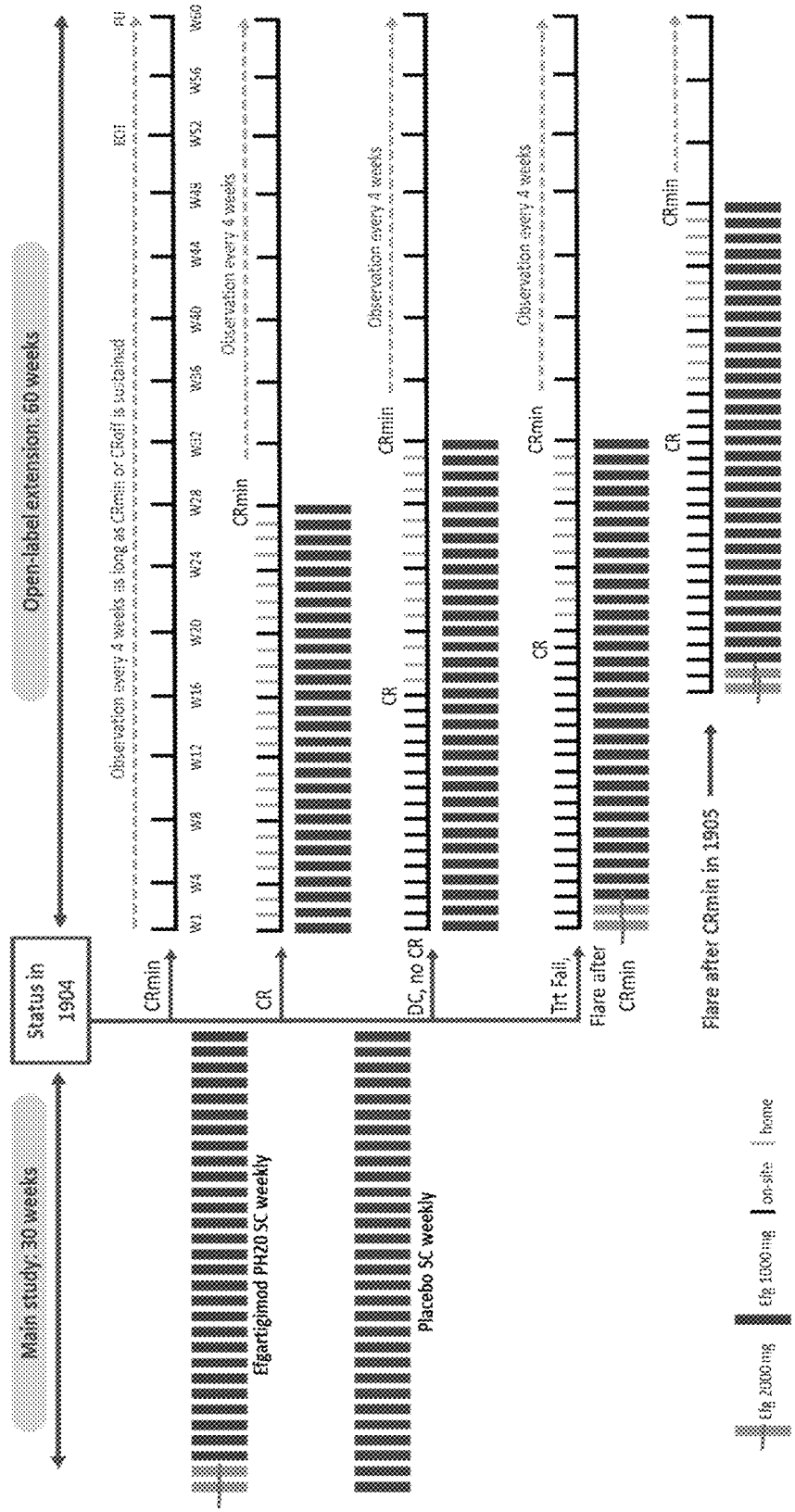

FIG. 14 is a diagram outlining the design of the Phase 3 clinical trial described in Example 14. CR-complete clinical remission; CRmin=complete remission on minimal therapy; CRoff-complete remission off therapy; DC-disease control; Efg-efgartigimod PH20 SC; EoT-end of treatment; FU-follow-up; SC-subcutaneous; Trt Fail=treatment failure; W=week.

DETAILED DESCRIPTION OF THE INVENTION

The present disclosure provides engineered FcRn antagonists and methods for their use in treating pemphigus, including pemphigus vulgaris and pemphigus foliaceus. Advantageously, the methods disclosed herein permit faster disease control than achieved with current therapies, as well as the potential to taper and even discontinue corticosteroids after achieving clinical remission.

Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art.

In order that the present invention may be more readily understood, certain terms are first defined.

As used herein, the term "FcRn" refers to a neonatal Fc receptor. Exemplary FcRn molecules include human FcRn encoded by the FCGRT gene as set forth in RefSeq NM 004107. The amino acid sequence of the corresponding protein is set forth in RefSeq NP_004098.

As used herein, the term "FcRn antagonist" refers to any agent that binds specifically to FcRn and inhibits the binding of immunoglobulin to FcRn (e.g., human FcRn).

As used herein, in certain embodiments the term "FcRn antagonist" refers to any agent comprising or consisting of an Fc region (e.g., a variant Fc region disclosed herein) that binds specifically to FcRn through the Fc region and inhibits the binding of immunoglobulin to FcRn. In certain embodiments, the FcRn antagonist is not a full-length IgG antibody. In certain embodiments, the FcRn antagonist comprises an antigen binding site that binds a target antigen and a variant Fc region disclosed herein. In other embodiments, the FcRn antagonist is an Fc fragment comprising or consisting of an Fc region and lacking an antigen binding site. In certain embodiments the term "FcRn antagonist" refers to an antibody or antigen-binding fragment thereof that binds specifically to FcRn via its antigen binding domain or via its Fc region, and inhibits the binding of the Fc region of immunoglobulin (e.g. IgG autoantibodies against desmosomal proteins) to FcRn.

As used herein, the term "Fc region" refers to the portion of a native immunoglobulin formed by the Fc domains of its two heavy chains. A native Fc region is homodimeric.

As used herein, the term "variant Fc region" refers to an Fc region with one or more alteration relative to a native Fc region. Alteration can include amino acid substitutions, additions and/or deletions, linkage of additional moieties, and/or alteration of the native glycans. The term encompasses heterodimeric Fc regions where each of the constituent Fc domains is different. Examples of such heterodimeric Fc regions include, without limitation, Fc regions made using the "knobs and holes" technology as described in, for example, U.S. Pat. No. 8,216,805, which is incorporated by reference herein in its entirety. The term also encompasses single chain Fc regions where the constituent Fc domains are linked together by a linker moiety, as described in, for example, US 2009/0252729A1 and US 2011/0081345A1, which are each incorporated by reference herein in their entirety.

As used herein, the term "Fc domain" refers to the portion of a single immunoglobulin heavy chain beginning in the hinge region just upstream of the papain cleavage site and ending at the C-terminus of the antibody. Accordingly, a complete Fc domain comprises at least a portion of a hinge (e.g., upper, middle, and/or lower hinge region) domain, a CH2 domain, and a CH3 domain.

As used herein the term "FcRn binding fragment" refers to a portion of an Fc region that is sufficient to confer FcRn binding.

As used herein, the term "EU position" refers to the amino acid position in the EU numbering convention for the Fc region described in Edelman, G. M. et al., *Proc. Natl. Acad. USA*, 63, 78-85 (1969) and Kabat et al, in "Sequences of Proteins of Immunological Interest", U.S. Dept. Health and Human Services, 5th edition, 1991.

As used herein, the term "CH1 domain" refers to the first (most amino terminal) constant region domain of an immunoglobulin heavy chain that extends from about EU positions 118-215. The CH1 domain is adjacent to the VH domain and amino terminal to the hinge region of an immunoglobulin heavy chain molecule, and does not form a part of the Fc region of an immunoglobulin heavy chain.

As used herein, the term "hinge region" refers to the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)). The FcRn antagonists of the instant disclosure can include all or a portion of a hinge region.

As used herein, the term "CH2 domain" refers to the portion of a heavy chain immunoglobulin molecule that extends from about EU positions 231-340.

As used herein, the term "CH3 domain" includes the portion of a heavy chain immunoglobulin molecule that extends approximately 110 residues from N-terminus of the CH2 domain, e.g., from about position 341-446 (EU numbering system).

As used herein, in certain embodiments the term "FcRn antagonist" refers to an antibody or antigen-binding fragment thereof that binds specifically to FcRn via its antigen binding domain and inhibits the binding of the Fc region of immunoglobulin to FcRn.

In an embodiment, an antibody that binds specifically to FcRn and inhibits the binding of the Fc region of immunoglobulin to FcRn is nipocalimab, also known as M281. Nipocalimab is a full-length (150 kDa) "Fc dead" (aglycoslated and effectorless) IgG1 monoclonal antibody. Nipocalimab has been administered as an intravenous infusion in Phase 2 clinical trials for the treatment of myasthenia gravis (MG), warm autoimmune hemolytic anemia (WAIHA), and hemolytic disease of fetus and newborn (HDFN).

Nipocalimab is described in WO2019/118791 and comprises the following light (SEQ ID NO: 4) and heavy (SEQ ID NO:5) chain sequences:

```
                                           (SEQ ID NO: 4)
QSALTQPASVSGSPGQSITISCTGTGSDVGSYNLVSWYQQHPGKAPKLM
IYGDSERPSGVSNRFSGSKSGNTASLTISGLQAEDEADYYCSSYAGSGI
YVFGTGTKVTVLGQPKAAPSVTLFPPSSEELQANKATLVCLISDFYPGA
VTVAWKADSSPVKAGVETTTPSKQSNNKYAASSYLSLTPEQWKSHKSYS
CQVTHEGSTVEKTVAPTECS (SEQ ID NO: 5)
EVQLLESGGGLVQPGGSLRLSCAASGFTESTYAMGWVRQAPGKGLEWVS
SIGASGSQTRYADSVKGRFTISRDNSKNTLYLQMNSLRAEDTAVYYCAR
LAIGDSYWGQGTMVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLS
LSPG
```

In an embodiment, an antibody that binds specifically to FcRn and inhibits the binding of the Fc region of immunoglobulin to FcRn is rozanolixizumab, also known as UCB 7665. Rozanolixizumab is a full-length (150 kDa) humanized IgG4 monoclonal antibody. Rozanolixizumab has been administered as a subcutaneous infusion in ongoing clinical trials for MG, immune thrombocytopenia (ITP), and chronic inflammatory demyelinating polyneuropathy (CIDP). Rozanolixizumab was first described in WO2014019727 and comprises the light chain of SEQ ID NO: 6 and the heavy chain of SEQ ID NO: 7.

```
                                           (SEQ ID NO: 6)
DIQMTQSPSSLSASVGDRVTITCKSSQSLVGASGKTYLYWLFQKPGKAP
KRLIYLVSTLDSGIPSRESGSGSGTEFTLTISSLQPEDFATYYCLQGTH
EPHTFGQGTKLEIKRTVAAPSVFIFPPSDEQLKSGTASVVCLLNNFYPR
EAKVQWKVDNALQSGNSQESVTEQDSKDSTYSLSSTLTLSKADYEKHKV
YACEVTHQGLSSPVTKSENRGEC (SEQ ID NO: 7)
EVPLVESGGGLVQPGGSLRLSCAVSGFTFSNYGMVWVRQAPGKGLEWVA
YIDSDGDNTYYRDSVKGRFTISRDNAKSSLYLQMNSLRAEDTAVYYCTT
GIVRPFLYWGQGTLVTVSSASTKGPSVFPLAPCSRSTSESTAALGCLVK
DYFPEPVTVSWNSGALTSGVHTFPAVLQSSGLYSLSSVVTVPSSSLGTK
TYTCNVDHKPSNTKVDKRVESKYGPPCPPCPAPEFLGGPSVELFPPKPK
DTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTP
PVLDSDGSFFLYSRLTVDKSRWQEGNVESCSVMHEALHNHYTQKSLSLS
LGK
```

In an embodiment, an antibody that binds specifically to FcRn and inhibits the binding of the Fc region of immunoglobulin to FcRn is orilanolimab, also known as SYNT001. Orilanolimab is another full-length (150 kDa) humanized IgG4 monoclonal antibody. Orilanolimab has been administered as an intravenous infusion in Phase 2 clinical trials for treatment of WAIHA.

In an embodiment, an antibody that binds specifically to FcRn and inhibits the binding of the Fc region of immunoglobulin to FcRn is batoclimab, also known as IMVT1401/RVT1401/HBM9161. Batoclimab is another full-length (150 kDa) "Fc dead" IgG1 monoclonal antibody. Batoclimab has been administered as a subcutaneous injection in ongoing Phase 2 clinical trials for treatment of MG and Graves' ophthalmopathy.

As used herein, the term "CD16" refers to FcγRIII Fc receptors that are required for Antibody-Dependent Cell-mediated Cytotoxicity (ADCC). Exemplary CD16 molecules include human CD16a as set forth in RefSeq NM_000569.

As used herein, the term "free cysteine" refers to native or engineered cysteine amino acid residue that exists in a substantially reduced form in a mature FcRn antagonist.

As used herein, the term "antibody" refers to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL). The VH and VL regions can be further subdivided into regions of hypervariability, termed complementarity determining regions (CDRs), interspersed with regions that are more conserved, termed framework regions (FR).

As used herein, an "antigen-binding fragment" of an antibody generally comprises at least one VH paired with one VL, which together are capable of specifically binding to a particular antigen or epitope. Antigen-binding fragments can include, without limitation, Fv, Fab, Fab', and F(ab')$_2$ fragments, as well as engineered single-chain FV (scFV) fragments, diabodies, and the like.

As used herein the term "N-linked glycan" refers to the N-linked glycan attached to the nitrogen (N) in the side chain of asparagine in the sequon (i.e., Asn-X-Ser or Asn-X-Thr sequence, where X is any amino acid except proline) present in the CH2 domain of an Fc region. Such N-Glycans are fully described in, for example, Drickamer K, Taylor M E (2006). Introduction to Glycobiology, 2nd ed., which is incorporated herein by reference in its entirety.

As used herein the term "afucosylated" refers to an N-linked glycan which lacks a core fucose molecule as described in U.S. Pat. No. 8,067,232, the contents of which is incorporated by reference herein in its entirety.

As used herein the term "bisecting GlcNAc" refers to an N-linked glycan having an N-acetylglucosamine (GlcNAc) molecule linked to a core mannose molecule, as described in U.S. Pat. No. 8,021,856, the contents of which is incorporated by reference herein in its entirety.

As used herein, the term "treat", "treating", and "treatment" refer to therapeutic or preventative measures described herein. In certain embodiments, the term "treat", "treating", and "treatment" refer to therapeutic measures described herein. The methods of "treatment" employ administration to a subject, an agent or combination of agents as described herein in order to prevent, cure, delay, reduce the severity of, or ameliorate one or more symptoms of a disease or disorder or recurring disease or disorder, or in order to prolong the survival of a subject beyond that expected in the absence of such treatment.

As used herein, the term "subject" includes any human or non-human mammal.

Pemphigus

Pemphigus is a group of chronic blistering epithelial diseases in which the production of IgG autoantibodies against extracellular domains of cell membrane proteins of keratinocytes results in acantholysis (loss of cell-cell adhesion between keratinocytes). Three major forms of pemphigus are: pemphigus vulgaris (PV), pemphigus foliaceus (PF), and paraneoplastic pemphigus (PP).

PV is caused by IgG autoantibodies against the desmosomal proteins, desmoglein-3 (Dsg-3) and/or desmoglein-1 (Dsg-1), on epidermal keratinocytes. Because the binding of the antibodies (IgG4 predominant, do not activate complement) to the extracellular domain of Dsg is sufficient to cause loss of keratinocyte adhesion and blister formation, they generate directly the clinical manifestations of PV. Dsg-3 is expressed almost exclusively in the basal and parabasal cell layers of the skin and throughout the squamous layer of mucus membranes, whereas Dsg-1 prevails in the superficial layer of the skin and is nearly absent in the mucosa. Accordingly, mucosal PV lesions are mostly induced by anti-Dsg 3 antibodies, whereas cutaneous PV lesions are triggered by both anti-Dsg 3 and anti-Dsg 1 antibodies. Interestingly, disease activity has been shown to be closely correlated with serum levels of antibodies against Dsg-1 and, to a lesser extent, Dsg-3. Belloni-Fortina A et al., *Clin Dev Immunol.* 2009; 187864. doi: 10.1155/2009/187864; Abasq C et al., *Arch Dermatol.* 2009; 145 (5): 529-35.

PF is caused by antibodies against Dsg-1, which is expressed in the superficial layer of the epidermis and, therefore, involves the skin only. Two forms have been described: the non-endemic form, and the endemic form (also called "folgo selvagem"). Folgo selvagem has been observed in the Amazonian region, where a non-infectious protein (LJM11) residing in the salivary glands of the sand fly (*Lutzomyia longipalpis*) was suggested to cause a cross-reaction with Dsg-1. Otherwise, endemic and non-endemic PF share the same clinical, histological and immunological findings. Like in PV, anti-Dsg 1 autoantibodies are directly pathogenic.

PV and PF are rare. Pemphigus vulgaris is the most common subtype of pemphigus in Europe, the United States and Japan; it preferentially affects women, and most of the patients are 50-60 years of age at disease onset (Kasperkiewicz, Nat. Re. Dis. Primers, 2017 May 11; 3:17026). Pemphigus foliaceus is the most common type observed in South America and North Africa owing to the endemic form, with sex predisposition differing among the regions and a preferential occurrence in young adults. PF is less common in North America and Europe (10-15% of pemphigus cases).

Both PV and PF are chronic and intractable, with a life-threatening potential. Clinically, PV presents as a mucosal-dominant, mucocutaneous or, less commonly, solely cutaneous type. Patients frequently shift from one type to another, typically from mucosal type at the beginning of the disease to become mucocutaneous later on. Mucocutaneous type tends to be a more severe disease, whereas diagnostic delay is common in the mucosal type. Although it may affect a wider range of age, its peak frequency ranges between 50 and 60 years of age. Women are slightly overrepresented in the PV population, in which the female-predominant thyroid diseases and rheumatoid arthritis are associated. Typically, lesions begin in the oral mucosa and may then extend to other mucosal areas and the skin. Mucosal involvement consists of flaccid blisters that rapidly rupture, leaving painful erosions. Mucosal lesions may also affect the pharynx, upper larynx, esophagus, nose and eyes, and genitals. They are usually associated with significant impairments, including difficulties of eating and swallowing, of having sexual intercourse, etc. They frequently lead to weight loss, malnutrition, and alteration of quality of life. Cutaneous lesions are characterized by flaccid blisters and erosions that easily ooze and become superinfected (crusty lesions). Although any skin area may be involved, lesions predominate in the head, upper trunk and groin. They are painful, especially in the folds. At examination, the epidermis can be detached when the finger rubs the skin at the periphery of the lesions (Nikolsky sign), which is highly indicative of PV diagnosis.

Diagnosis of PV follows an algorithm of different tools, which generally are performed in the presence of clinical manifestations suggestive of the disease. They include histology, direct immunofluorescence (DIF), and the detection of autoantibodies against Dsg-3 and/or Dsg-1 in serum either through indirect immunofluorescence (IIF) or enzyme-linked immunosorbent assay (ELISA) tests. Histopathology typically shows supra-basal acantholysis (keratinocytes floating in blister fluid). Acantholysis is highly suggestive of PV, as it is not seen in other autoimmune blistering diseases such as bullous pemphigoid (BP), but the diagnosis should be confirmed by the characteristic deposition of IgG and/or complement on the cell surface of keratinocytes by DIF. Today, while DIF is considered as the gold standard investigation for diagnosis, IIF and/or ELISA are necessary to confirm the diagnosis. Commercial ELISA assays are available for quantitative measurement of Dsg-1 and Dsg-3 autoantibodies in serum. They potentially offer advantages over IIF, such as increased sensitivity (>90%), but they are not helpful for excluding other self-antigens and autoimmune bullous dermatoses (AIBD). Therefore, IIF and ELISA may be considered complementary in the diagnostic investigation of PV. Taken together, current international guidelines recommend making a diagnosis of PV in patients with indicative clinical signs, confirmed by histopathology, positive DIF, and positive IIF and/or ELISA. Hertl M et al., *J Eur Acad Dermatol Venereol.* 2015; 29 (3): 405-14.

PV is a chronic disease, with no tendency of spontaneous improvement. On the contrary, the disease typically worsens progressively and has a mortality rate three times higher than in the general population when untreated. Under treatment, the disease usually evolves in periods of remission and relapse. Eventually, it takes many years for achieving a definite cure. As treatments are part of the co-morbidity factors that are related to their high rate of serious side effects, mortality is still high, and severe infections remain today the main cause of death. Ren Z et al., *J Eur Acad Dermatol Venereol.* 2018; 32 (10): 1768-1776.

Because Dsg-1 is expressed in the superficial portion of the epidermis, PF patients typically present with itchy, scaly and crusted erosions of the cutaneous tissue. Blisters are uncommonly seen, owing to their superficial nature and easy rupture. Another clinical variant may be the development of squamous and crusty lesions on the face, scalp, chest and inter-scapular areas ("seborrheic pemphigus"). In more severe forms, desquamative erythroderma may be observed involving almost all of the skin surface. PF diagnosis follows the investigational tools which are used in PV. At histology, a cleft in the subcorneal or the superficial granular layer can be seen. DIF shows the intercellular deposition of IgG within the epidermis, and IIF reveals the presence of serum autoantibodies against intercellular components of the skin. ELISA tests quantify the positive level of anti-Dsg-1 antibodies in serum, whereas the search for anti-Dsg-3 antibodies is negative.

Like PV, PF does not tend to resolve spontaneously. Treatment is always needed, with the aim of healing existing lesions and preventing the appearance of new lesions as soon as possible.

Additional forms of pemphigus include pemphigus vegitans, pemphigus erythematosus, herpetiform pemphigus, and drug-induced pemphigus. Pemphigus vegitans is a variant of PV characterized by fungoid vegetations and mediated by anti-Dsg 3 IgG autoantibodies. Pemphigus erythematosus is a variant of PF characterized by localized involvement, mainly on the face and upper part of the chest and back, and mediated by anti-Dsg 1 IgG autoantibodies. Herpetiform pemphigus is a subtype characterized by small vesicles and pustules, and mediated mainly by anti-Dsg 1 IgG autoantibodies.

Current Approaches to Treatment of Pemphigus

To help the practitioners in the therapeutic management of pemphigus patients, the following consensual definitions of the most important clinical endpoints among national and international experts, as well as regular guidelines for the diagnosis and treatment of these diseases are available (see Murrell et al., *J Am Acad Dermatol*. 2008; 58:1043; Murrell et al., *J Am Acad Dermatol*. 2018 Feb. 10; Harman et al., *Br J Dermatol*. 2017 November; 177 (5): 1170-1201; Joly et al., *Lancet*. 2017 May 20; 389 (10083): 2031-2040), Hébert et al., *J Invest Dermatol*. 2019 January; 139 (1): 31-37, which are incorporated herein by reference):

(a) "Disease Control" (DC)—no new pemphigus lesions and established lesions begin to heal;
(b) "End of Consolidation Phase" (EoC)—no new pemphigus lesions for at least 2 weeks and about 80% established lesions are healed.
(c) "Complete Remission" (CR)—absence of new or established lesions, also referred to as "Complete Clinical Remission".
(d) "Complete Remission Off Therapy" (CRoff)—absence of new or established lesions while the patient is off all systemic therapy for at least 2 months.
(e) "Complete Remission On Therapy" (CRmin)—absence of new or established lesions while the patient is receiving Minimal Therapy.
(f) "Minimal Therapy"-prednisone (or the equivalent) at a dose of 10 mg/day or less and/or minimal adjuvant therapy for at least 2 months (for practical reasons during clinical trials this is shortened to 8 weeks).
(g) "Off Therapy"-no systemic drug for at least 2 months.
(h) "Relapse" or "Flare" (R)-appearance of 3 or more lesions a month that do not heal within 1 week, or extension of established lesions.
(i) "Treatment Failure"-failure to reach disease control with full therapeutic doses of systemic treatments (e.g., prednisone 1.5 mg/kg/day for 3 weeks).

In addition, validated scales for monitoring disease activity and extension (have been established (See, e.g., Rosenbach M et al., *J Invest Dermatol*. 2009; 129 (10): 2404-10; Rahbar Z et al., *JAMA Dermatol*. 2014; 150 (3): 266-72). Exemplary validated scores include the Pemphigus Disease Area Index (PDAI) and the Autoimmune Bullous Skin disorder Intensity Score (ABSIS). The pemphigus Disease Area Index (PDAI) is a well-established and widely used diagnostic tool used to assess and classify the severity of pemphigus in afflicted human subjects. Using the PDAI, the severity of disease is scored on a scale from 0-263, where a score of 0 signifies no disease and a score of 263 signifies maximally severe disease.

Severity thresholds for mild, moderate, and severe pemphigus have been suggested in different papers with partially overlapping patient populations proposing PDAI 9 or 15 as cut-off values between mild and moderate/severe disease, and 25 or 45 as cut-off values between moderate and severe disease (Shimizu et al., *J Dermatol*. 2014; 41 (11): 969-973; Boulard et al., *Br J Dermatol*. 2016; 175 (1): 142-9). International guidelines concluded that it is currently premature to definitively state cut-off values to define mild, moderate, or severe disease (Murrell et al., *J Am Acad Dermatol*. 2020; 82 (3): 575-585).

In exemplary embodiments, "Mild Pemphigus" is characterized as a PDAI score of less than 15; "Moderate Pemphigus" is characterized by a PDAI score of 15 to less than 45 and "Severe Pemphigus" is characterized by a PDA Score of 45 or greater. The Autoimmune Bullous Disease Quality of Life (ABQOL) score was developed and validated for ascertaining the impact of the disease and its therapies on patients' daily lives. Sebaratnam D F et al., *JAMA Dermatol*. 2013; 149 (10): 1186-91.

According to the most recent international guideline (Ren Z et al., *J Eur Acad Dermatol Venereol*. 2018; 32 (10): 1768-1776), corticosteroids remain a first line therapy in pemphigus. They are the most rapidly acting form of treatment known today and provide disease control (no new lesions, established lesions starting to heal) in about 3 weeks when used at effective dose. Ratnam K V et al., *Int J Dermatol*. 1990; 29 (5): 363-7; Czernik A et al., *Arch Dermatol*. 2008; 144 (5): 658-61; Chaidemenos G et al., *J Eur Acad Dermatol Venereol*. 2011; 25 (2): 206-10. Oral prednisone is the most commonly used corticosteroid. The starting oral prednisone dose is high, ranging from 1-2 mg/kg daily, and may be reduced (0.5-1 mg/kg per day) if combined with rituximab or immunosuppressants. If disease control is not achieved after 3-4 weeks at the latest, the prednisone dose must be increased. In patients with very active disease, intravenous bolus of corticosteroids (e.g. methylprednisolone) may be preferred, especially at the treatment initiation.

As used herein, the term "prednisone equivalent dose" means a dose of prednisone or an equivalent dose of a systemic corticosteroid other than prednisone. Systemic corticosteroids are well-known and include compounds of various potencies and formulations. These are generally formulated as injectables or pills. Examples of commercially available systemic corticosteroids include, without limitation, betamethasone, cortisone, dexamethasone, hydrocortisone, methylprednisolone, prednisone, prednisolone, and triamcinolone.

In certain embodiments, a topical corticosteroid may also be administered. Topical corticosteroids are well-known and include compounds of various potencies and formulations. These are generally formulated as ointments, creams, oils, lotions, shampoos, foams, and/or gels. Examples of commercially available topical corticosteroids include alclometasone dipropionate, amcinonide, betamethasone dipropionate, betamethasone valerate, clobetasol propionate, clobetasone butyrate, desonide, desoximetasone, diflucortolone valerate, diflorasone diacetate, fluocinolone acetonide, fluocinonide, flurandrenolide, fluticasone propionate, halcinonide, halobetasol propionate, hydrocortisone, hydrocortisone 17-butyrate, hydrocortisone acetate, hydrocortisone valerate, methylprednisolone aceponate, mometasone furoate, prenicarbate, and triamcinolone acetonide. Topical corticosteroids conveniently can be applied locally to affected areas or lesions in need of treatment, thereby limiting undesirable systemic effects of corticosteroid treatment.

The therapeutic management of patients with pemphigus is very challenging. Its primary principles are, on the one hand, to promptly stop the occurrence of new blisters and then achieve clinical remission and, on the other hand, to minimize the side effects of systemic therapy, e.g., corticosteroids. Corticosteroids have a high cumulative toxicity in these chronic diseases that must be mitigated by reducing their amount and duration of exposure as much as possible. Secondarily, the objective of the treatments is to prevent the development of new lesions either on minimal corticosteroid therapy, or even without any treatment. For this purpose, patients must be managed by referral centers, where they can be monitored carefully by experienced dermatologists. In many patients, a multi-disciplinary approach is necessary, including specialists in oral medicine, ophthalmologists, and gynecologists when mucosal lesions are present.

After disease control, oral prednisone is maintained at a stable dose for consolidating disease control. End of consolidation is defined as the absence of new lesions for at least 2 weeks and about 80% of established lesions already healed. This time point is chosen by a majority of practitioners as the inflexion time at which prednisone starts to be tapered. The duration of the consolidation period varies greatly between patients, mucosal erosions and extensive cutaneous lesions tending to be late to heal.

Once disease control is consolidated, a tapering schedule is put in place, during which the prednisone dose is gradually reduced. The goal of this phase is to reach complete clinical remission (no new lesions, all established lesions completely healed) and, at the same time, reach a minimal effective dose of prednisone (10 mg per day or less for at least 2 months), or even stop prednisone (off-therapy), in order to prevent side effects. Unfortunately, this double objective is hard to achieve and a majority of patients relapse under tapered dose of prednisone. In a prospective trial, 64% of PV patients with prednisone achieved a first clinical remission on minimal dose after 12 months, but relapse occurred frequently, i.e. in 45% of the cases within 6 months. Beissert S et al., *J Invest Dermatol.* 2010; 130 (8): 2041-8. Finally, the common course of PV is one of episodes of relapse and transient remission, and it takes several years of prednisone treatment before achieving permanent remission. In one study, 36% of patients with PV were treated with prednisone or equivalent for at least 10 years. Mimouni D et al., *J Eur Acad Dermatol Venereol.* 2010; 24 (8): 947-52. Meanwhile, the risk of corticosteroid-related side effects (osteoporosis, diabetes, hypertension, Cushing syndrome, cataracts, glaucoma, infections, etc.) increases with treatment duration. Accordingly, most PV patients need adjuvant therapies (e.g., rituximab, immunosuppressants) in order to maintain them under remission and reduce the cumulative prednisone dose.

As used herein, the term "initial dose" means a starting corticosteroid dose or initial dose of corticosteroids as administered to a pemphigus patient (before tapering).

As used herein, the term "tapering dose" means a reduced corticosteroid dose as administered to a pemphigus patient. The term "initial tapering dose" means the first, reduced corticosteroid dose as administered to a pemphigus patient, e.g. a dose of 0.5 mg/kg/day prednisone or equivalent. Further reduced tapering doses may be administered. The reduction of the initial and/or subsequent tapering dose can occur on a periodic basis, e.g. every 2 weeks.

The recent approval of rituximab in PV adults has dramatically changed the mainstay of therapy of the disease, and is now proposed as a first-line therapy in association with prednisone for the more severe cases. Ren Z et al., *J Eur Acad Dermatol Venereol.* 2018; 32 (10): 1768-1776. Until recently, rituximab was primarily used in refractory PV patients, who do not respond well to other treatments. However, the lack of long-lasting remission and great number of serious adverse events associated with prednisone and immunosuppressants has led researchers to develop alternative first-line treatments. Rituximab as second-line and third-line treatment (1-2 g per cycle) was shown to induce long-term remission at a high rate, which could not be achieved by any other treatment (75% remission rate in PV after 1 year). Relapse rates after rituximab therapy ranged between 25% after 1 year up to 80% in long-term follow-up. Wang H H et al., *Acta Derm Venereol.* 2015; 95 (8): 928-32. Recent evidence has shown efficacy of a first cycle of rituximab (2 g) as first-line treatment followed by new cycles (0.5 g) after 12 months and 18 months, in combination with lower doses of prednisone (0.5-1 mg/kg per day according to disease severity). Joly et al., *Lancet.* 2017 May 20; 389 (10083): 2031-2040). Using this first-line regimen, a higher proportion of complete remission (in this context what is meant is Complete Remission Off Therapy) after 2 years, i.e. 89%, was demonstrated. Relapse cases were observed to be lower (24% after 2 years), a majority occurring within 6 to 12 months after the first cycle. A strong prednisone sparing effect, i.e. by about two thirds, was demonstrated.

Nevertheless, rituximab, either used as first-line or second-/third-line treatment, has a late onset of action and does not result in an early achievement of disease control (mean time from first infusion: 6-7 weeks) and clinical remission (mean of 6-7 months on minimal prednisone therapy, 9 months off-therapy). Hébert V et al., *J Invest Dermatol.* 2019; 139 (1): 31-37; Wang H H et al., *Acta Derm Venereol.* 2015; 95 (8): 928-32. Furthermore, rituximab therapy carries the risk of inducing serious adverse events (e.g. 33% of infections). Late-onset neutropenia and hypogammaglobulinemia and the risk for patients to develop potentially fatal infections (e.g. *Pneumocystis carinii*, multifocal leukoencephalopathy, septicemia) require a long-term monitoring of the clinical and immunological status of the patients under rituximab.

Patients with PF typically follow the same type of management and monitoring of clinical outcome measures as PV patients, although rituximab has not been approved for this condition.

FcRn Antagonists

The neonatal Fc receptor (FcRn) influences serum levels and tissue distribution of IgG during all stages of life. FcRn is an intracellular trafficking, integral membrane receptor for IgG. Consequently, FcRn is a multifunctional molecule primarily involved in IgG transport and homeostasis. Challa D K et al., *Curr Top Microbiol Immunol.* 2014; 382:249-72; Roopenian D C et al., *Nat Rev Immunol.* 2007; 7 (9): 715-25. Following IgG uptake by pinocytosis in FcRn-expressing cells, the Fc part of IgGs binds FcRn with high affinity in early, acidic endosomes (pH<6.5). This binding spares IgGs from lysosomal degradation and drives them to the cell surface for recycling. At the near-neutral pH (PH~7.4) of the extracellular space, IgGs are released from the complex with FcRn. This pH-dependent salvage pathway is accountable for the maintenance of high IgG concentrations in circulation and for the long half-life ($t_{1/2}$) of IgGs compared to other Igs, which are not recycled. Roopenian D C et al., *J Immunol.* 2003; 170 (7): 3528-33; Waldmann T A et al., *J Clin Invest.* 1990; 86 (6): 2093-2098; Wani M A et al., *Proc Natl Acad Sci USA.* 2006; 103 (13): 5084-5089.

In one aspect, the invention provides methods of treatment of pemphigus using FcRn antagonist compositions. In certain embodiments, these compositions comprise or consist of a variant Fc region, or FcRn-binding fragment thereof, that binds specifically to FcRn, particularly human FcRn, with increased affinity and reduced pH dependence relative to a native Fc region. In other embodiments, the FcRn antagonist composition is an antibody or antigen-binding fragment thereof that binds specifically to FcRn via its antigen binding domain and inhibits the binding of Fc region of immunoglobulin to FcRn. In general, these FcRn antagonists inhibit the binding of Fc-containing agents (e.g., antibodies and immunoadhesins) to FcRn in vivo, which results in an increased rate of degradation of the Fc-containing agents and, concomitantly, a reduced serum level of these agents.

An isolated variant Fc region (e.g., a variant Fc region comprising the amino acids Y, T, E, K, F, and Y at EU positions 252, 254, 256, 433, 434, and 436 respectively) is a more efficacious FcRn antagonist in vivo than a full-length antibody comprising the same variant Fc region. Accordingly, in certain embodiments, the FcRn antagonist compositions are not full-length antibodies. In certain embodiments, the FcRn antagonist compositions do not comprise an antibody variable domain. In certain embodiments, the FcRn antagonist compositions do not comprise an antibody variable domain or a CH1 domain. However, in certain embodiments, the FcRn antagonist compositions may comprise a variant Fc region linked to one or more additional binding domains or moieties, including antibody variable domains.

Any Fc region can be altered to produce a variant Fc region for use in the FcRn antagonist compositions disclosed herein. In general, an Fc region, or FcRn-binding fragment thereof, is from a human immunoglobulin. It is understood, however, that the Fc region may be derived from an immunoglobulin of any other mammalian species, including for example, a Camelid species, a rodent (e.g. a mouse, rat, rabbit, guinea pig) or non-human primate (e.g. chimpanzee, macaque) species. Moreover, the Fc region or portion thereof may be derived from any immunoglobulin class, including IgM, IgG, IgD, IgA and IgE, and any immunoglobulin isotype, including IgG1, IgG2, IgG3 and IgG4. In certain embodiments, the Fc region is an IgG Fc region (e.g., a human IgG region). In certain embodiments, the Fc region is an IgG1 Fc region (e.g., a human IgG1 region). In certain embodiments, the Fc region is a chimeric Fc region comprising portions of several different Fc regions. Suitable examples of chimeric Fc regions are set forth in US 2011/0243966A1, which is incorporated herein by reference in its entirety. A variety of Fc region gene sequences (e.g. human constant region gene sequences) are available in the form of publicly accessible deposits. It will be appreciated that the scope of this invention encompasses alleles, variants and mutations of Fc regions.

An Fc region can be further truncated or internally deleted to produce a minimal FcRn-binding fragment thereof. The ability of an Fc-region fragment to bind to FcRn can be determined using any art recognized binding assay e.g., ELISA.

To enhance the manufacturability of the FcRn antagonists disclosed herein, it is preferable that the constituent Fc regions do not comprise any non-disulphide bonded cysteine residues. Accordingly, in certain embodiments the Fc regions do not comprise a free cysteine residue.

Any Fc variant, or FcRn-binding fragment thereof, that binds specifically to FcRn with increased affinity and reduced pH dependence relative to the native Fc region can be used in the FcRn antagonist compositions disclosed herein. In certain embodiments, the variant Fc region comprises amino acid alterations, substitutions, insertions and/or deletions that confer the desired characteristics. In certain embodiments, the variant Fc region or fragment comprises the amino acids Y, T, E, K, F, and Y at EU positions 252, 254, 256, 433, 434, and 436, respectively. Non-limiting examples of amino acid sequences that can be used in variant Fc regions are set forth in Table 1, below.

TABLE 1

Amino acid sequences of non-limiting examples of variant Fc regions

| SEQ ID NO: | Amino Acid Sequence |
|---|---|
| 1 | DKTHTCPPCPAPELLGGPSVFLFPPKPKDTLYITREPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESN GQPENNYKTTPPVLDSDGSFFLYSKLTVDKSRWQQGNVFSC SVMHEALKFHYTQKSLSLSPG |
| 2 | DKTHTCPPCPAPELLGGPSVFLFPPKPKDTLYITREPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESN GQPENNYKTTPPVLDSDGSFFLYSKLTVDKSRWQQGNVFSC SVMHEALKFHYTQKSLSLSPGK |
| 3 | CPPCPAPELLGGPSVFLFPPKPKDTLYITREPEVTCVVVDV SHEDPEVKFNWYVDGVEVHNAKTKPREEQYNSTYRVVSVLT VLHQDWLNGKEYKCKVSNKALPAPIEKTISKAKGQPREPQV YTLPPSRDELTKNQVSLTCLVKGFYPSDIAVEWESNGQPEN NYKTTPPVLDSDGSFFLYSKLTVDKSRWQQGNVFSCSVMHE ALKFHYTQKSLSLSPG |

Amino acids at EU positions 252, 254, 256, 433, and 434 are bold

In certain embodiments, an FcRn-antagonist consists of a variant Fc region, wherein the amino acid sequence of the Fc domains of the variant Fc region comprises the amino acid sequence set forth in SEQ ID NO: 1, 2, or 3. In certain embodiments, the amino acid sequence of the Fc domains of the variant Fc region comprises the amino acid sequence set forth in SEQ ID NO: 1. In certain embodiments, the amino acid sequence of the Fc domains of the variant Fc region comprises the amino acid sequence set forth in SEQ ID NO: 2. In certain embodiments, the amino acid sequence of the Fc domains of the variant Fc region comprises the amino acid sequence set forth in SEQ ID NO: 3.

In certain embodiments an FcRn-antagonist consists of a variant Fc region, wherein the amino acid sequence of the Fc domains of the variant Fc region consists of the amino acid sequence set forth in SEQ ID NO: 1, 2, or 3. In certain embodiments, the amino acid sequence of the Fc domains of the variant Fc region consists of the amino acid sequence set forth in SEQ ID NO: 1. In certain embodiments, the amino acid sequence of the Fc domains of the variant Fc region consists of the amino acid sequence set forth in SEQ ID NO: 2. In certain embodiments, the amino acid sequence of the Fc domains of the variant Fc region consists of the amino acid sequence set forth in SEQ ID NO: 3.

In certain embodiments an FcRn-antagonist consists of a variant Fc region, wherein said variant Fc region consists of two Fc domains which form a homodimer, wherein the amino acid sequence of each of the Fc domains is selected from the group consisting of SEQ ID NO: 1, SEQ ID NO: 2, and SEQ ID NO: 3. In certain embodiments an FcRn-antagonist consists of a variant Fc region, wherein said variant Fc region consists of two Fc domains which form a homodimer, wherein the amino acid sequence of each of the Fc domains is SEQ ID NO: 1. In certain embodiments an FcRn-antagonist consists of a variant Fc region, wherein said variant Fc region consists of two Fc domains which form a homodimer, wherein the amino acid sequence of each of the Fc domains is SEQ ID NO: 2. In certain embodiments an FcRn-antagonist consists of a variant Fc region, wherein said variant Fc region consists of two Fc domains which form a homodimer, wherein the amino acid sequence of each of the Fc domains is SEQ ID NO: 3.

In certain embodiments, the variant Fc region has altered (e.g., increased or decreased) binding affinity for an additional Fc receptor. The variant Fc region can have altered (e.g., increased or decreased) binding affinity for one or more of Fcγ receptors e.g., FcγRI (CD64), FcγRIIA (CD32a), FcγRIIB (CD32b), FcγRIIIA (CD16a), and FcγRIIIB (CD16b). Any art-recognized means of altering the affinity for an additional Fc receptor can be employed. In certain embodiments, the amino acid sequence of the variant Fc region is altered.

In certain embodiments, the variant Fc region comprises a non-naturally occurring amino acid residue at one or more positions selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217, the contents of which are incorporated by reference herein in their entirety).

In certain embodiments, the variant Fc region comprises at least one non-naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241R. 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217, the contents of which are incorporated by reference herein in their entirety).

Other known Fc variants that may be used in the FcRn antagonists disclosed herein include without limitations those disclosed in Ghetie et al., 1997, *Nat. Biotech.* 15:637-40; Duncan et al, 1988, *Nature* 332:563-564; Lund et al., 1991, *J. Immunol.*, 147:2657-2662; Lund et al, 1992, *Mol. Immunol.*, 29:53-59; Alegre et al, 1994, *Transplantation* 57:1537-1543; Hutchins et al., 1995, *Proc Natl. Acad Sci USA*, 92:11980-11984; Jefferis et al, 1995, *Immunol Lett.*, 44:111-117; Lund et al., 1995, *FASEB J.*, 9:115-119; Jefferis et al, 1996, *Immunol Lett.*, 54:101-104; Lund et al, 1996, *J. Immunol.*, 157:4963-4969; Armour et al., 1999, *Eur J Immunol* 29:2613-2624; Idusogie et al, 2000, *J. Immunol.*, 164:4178-4184; Reddy et al, 2000, *J. Immunol.*, 164:1925-1933; Xu et al., 2000, *Cell Immunol.*, 200:16-26; Idusogie et al, 2001, *J. Immunol.*, 166:2571-2575; Shields et al., 2001, *J Biol. Chem.*, 276:6591-6604; Jefferis et al, 2002, *Immunol Lett.*, 82:57-65; Presta et al., 2002, *Biochem Soc Trans.*, 30:487-490); U.S. Pat. Nos. 5,624,821; 5,885,573; 5,677, 425; 6,165,745; 6,277,375; 5,869,046; 6,121,022; 5,624, 821; 5,648,260; 6,528,624; 6,194,551; 6,737,056; 6,821, 505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351, the contents of which are incorporated by reference herein in their entirety.

In certain embodiments, the variant Fc region is a heterodimer, where the constituent Fc domains are different from each other. Methods of producing Fc heterodimers are known in the art (see e.g., U.S. Pat. No. 8,216,805, which is incorporated by reference herein in its entirety). In certain embodiments, the variant Fc region is a single chain Fc region, where the constituent Fc domains are linked together by a linker moiety. Methods of producing single chain Fc regions are known in the art (see e.g., US 2009/0252729A1 and US 2011/0081345A1, which are each incorporated by reference herein in their entirety).

It is believed that pathogenic IgG antibodies observed in autoimmune diseases are either the pathogenic triggers for these diseases or contribute to disease progression and mediate disease through the inappropriate activation of cellular Fc receptors. Aggregated autoantibodies and/or autoantibodies complexed with self antigens (immune complexes) bind to activating Fc receptors, causing numerous autoimmune diseases (which occur in part because of immunologically mediated inflammation against self tissues) (see e.g., Clarkson et al., *New Engl J Med* 314 (9), 1236-1239 (2013)); US 2004/0010124A1; US 2004/0047862A1; and US 2004/0265321A1, which are each incorporated by reference herein in their entirety). Accordingly, to treat antibody-mediated disorders (e.g. autoimmune diseases), it would be advantageous to both remove the deleterious autoantibodies and to block the interaction of the immune complexes of these antibodies with activating Fc receptors (e.g., Fcγ receptors, such as CD16a).

Accordingly, in certain embodiments, the variant Fc region of the FcRn antagonist exhibits increased binding to CD16a (e.g., human CD16a). This is particularly advantageous in that it allows the FcRn antagonist to additionally antagonize the immune complex-induced inflammatory response of autoantibodies being targeted for removal by FcRn inhibition. Any art recognized means of increasing affinity for CD16a (e.g., human CD16a) can be employed. In certain embodiments, the FcRn-antagonist comprises a variant Fc-region comprising an N-linked glycan (e.g., at EU position 297). In this case it is possible to increase the binding affinity of the FcRn-antagonist for CD16a by altering the glycan structure. Alterations of the N-linked glycan of Fc regions are well known in the art. For example, afucosylated N-linked glycans or N-glycans having a bisecting GlcNAc structure have been shown to exhibit increased affinity for CD16a. Accordingly, in certain embodiments, the N-linked glycan is afucosylated. Afucosylation can be achieved using any art-recognized means. For example, an FcRn-antagonist can be expressed in cells lacking fucosyl transferase, such that fucose is not added to the N-linked glycan at EU position 297 of the variant Fc region (see e.g., U.S. Pat. No. 8,067,232, the contents of which is incorporated by reference herein in its entirety). In certain embodiments, the N-linked glycan has a bisecting GlcNAc structure. The bisecting GlcNAc structure can be achieved using any art recognized means. For example, an FcRn-antagonist can be expressed in cells expressing beta1-4-N-acetylglucosaminyltransferase III (GnTIII), such that bisecting GlcNAc is added to the N-linked glycan at EU position 297 of the variant Fc region (see e.g., U.S. Pat. No. 8,021,856, the contents of which is incorporated by reference herein in its entirety). Additionally or alternatively, alterations of the N-linked glycan structure can also be achieved by enzymatic means in vitro.

In certain embodiments, the instant disclosure provides FcRn-antagonist compositions wherein a portion of the FcRn-antagonist molecules contained therein comprise altered glycan structures. In certain embodiments, the FcRn-antagonist composition comprises a plurality of FcRn-antagonist molecules disclosed herein, wherein at least 50% (optionally, at least 60, 70, 80, 90, 95, or 99%) of the molecules comprise an Fc region or FcRn-binding fragment thereof having an afucosylated N-linked glycan. In certain embodiments, the FcRn-antagonist composition comprising a plurality of FcRn-antagonist molecules disclosed herein, wherein at least 50% (optionally, at least 60, 70, 80, 90, 95, or 99%) of the molecules comprise an Fc region or FcRn-binding fragment thereof comprising an N-linked glycan having a bisecting GlcNAc.

In certain embodiments, the variant Fc region does not comprise an N-linked glycan. This can be achieved using any art recognized methods. For example, the Fc variant can be expressed in a cell that is incapable of N-linked glycosylation. Additionally or alternatively, the amino acid sequence of the Fc variant can be altered to prevent or inhibit N-linked glycosylation (e.g., by mutation of the NXT sequon). Alternatively, the Fc variant can be synthesized in an acellular system (e.g., chemically synthesized).

In certain embodiments, FcRn-antagonist molecules may be modified, e.g., by the covalent attachment of a molecule (e.g., a binding or imaging moiety) to the FcRn-antagonist such that covalent attachment does not prevent the FcRn-antagonist from specifically binding to FcRn. For example, but not by way of limitation, the FcRn-antagonist may be modified by glycosylation, acetylation, pegylation, phosphorylation, amidation, derivatization by known protecting blocking groups, proteolytic cleavage, linkage to a cellular ligand or other protein, etc.

In certain embodiments, the FcRn antagonist comprises a variant Fc region linked to a half-life extender. As used herein, the term "half-life extender" refers to any molecule that, when linked to an FcRn antagonist disclosed herein, increases the half-life of an FcRn antagonist. Any half-life extender may be linked (either covalently or non-covalently) to the FcRn antagonist. In certain embodiments, the half-life extender is polyethylene glycol or human serum albumin. In certain embodiments, the FcRn antagonist is linked to a binding molecule that specifically binds to a half-life extender present in a subject, such as a blood-carried molecule or cell, such as serum albumin (e.g., human serum albumin), IgG, erythrocytes, etc.

The FcRn antagonists disclosed herein have excellent manufacturability. For example, they can be expressed at high levels in mammalian cells (e.g., at 6 g/L in CHO cells in a 10 L stirred tank bioreactor). Moreover, after Protein A purification, the resultant purified FcRn antagonist composition has a very high percentage of FcRn antagonist monomers, and contains an extremely low level of FcRn antagonist protein aggregates and degradation products. Accordingly, in certain embodiments, the instant disclosure provides an FcRn antagonist composition comprising a plurality of FcRn antagonist molecules as disclosed herein, wherein greater than 95% the of the FcRn antagonist molecules in the composition are monomers (e.g., greater than 95, 96, 97, 98, 99, 99.1, 99.2, 99.3, 99.4, 99.5, 99.6, 99.7, 99.8, 99.9%). In certain embodiments, the instant disclosure provides an FcRn antagonist composition comprising a plurality of FcRn antagonist molecules disclosed herein, wherein less than 5% the of the FcRn antagonist molecules in the composition are present in aggregates, (e.g., less than 5, 4, 3, 2, 1, 0.9, 0.8, 0.7, 0.6, 0.5, 0.4, 0.3, 0.2, 0.1%). In certain embodiments, the instant disclosure provides an FcRn antagonist composition comprising a plurality of FcRn antagonist molecules disclosed herein, wherein the composition is substantially free of FcRn antagonist molecule degradation products.

Methods for production of FcRn antagonists useful in the instant invention are disclosed in, for example, U.S. Pat. No. 10,316,073, the contents of which is incorporated by reference herein in its entirety.

The FcRn antagonist compositions can be used alone or in combination with one or more additional therapeutic agents. In certain embodiments, the additional therapeutic agent is an anti-inflammatory agent. Any anti-inflammatory agent can be used in combination with the FcRn antagonists disclosed herein. Anti-inflammatory agents include corticosteroids, e.g., prednisone, prednisolone, methylprednisolone, cortisone, hydrocortisone, betamethasone, triamcinolone, and dexamethasone. In certain embodiments, the additional therapeutic agent is rituximab, daclizumab, basiliximab, muronomab-CD3, infliximab, adalimumab, omalizumab, efalizumab, natalizumab, tocilizumab, eculizumab, golimumab, canakinumab, ustekinumab, or belimumab. In certain embodiments, the additional therapeutic agent is a leucocyte depleting agent (e.g., B-cell or T-cell depleting agent). Any leucocyte depleting agent can be used in combination with the FcRn antagonist compositions disclosed herein. In certain embodiments, the leucocyte depleting agent is a B-cell depleting agent. In certain embodiments, the leucocyte depleting agent is an antibody against a cell surface marker. Suitable cell surface markers include, without limitation, CD10, CD19, CD20, CD21, CD22, CD23, CD24, CD37, CD53, CD70, CD72, CD74, CD75, CD77, CD79a, CD79b, CD80, CD81, CD82, CD83, CD84, CD85, or CD86. In certain exemplary embodiments, the B-cell depleting agent is an antibody that binds CD20 (e.g., Rituxan). The FcRn antagonist and the additional therapeutic agent(s) can be administered to the subject simultaneously or sequentially, via the same or different route(s) of administration.

Efgartigimod

Efgartigimod (ARGX-113) is a modified human immunoglobulin (Ig) gamma (IgG) 1-derived Fc of the za allotype that binds with nanomolar affinity to human FcRn. Efgartigimod encompasses IgG1 residues D220-K447 (EU numbering scheme) and has been engineered using ABDEG™ technology to increase its affinity for FcRn at both physiological and acidic pH. Vaccaro C et al., *Nat Biotechnol.* 2005; 23 (10): 1283. See also U.S. Pat. No. 10,316,073, the contents of which is incorporated by reference herein in its entirety. The increased affinity for FcRn of efgartigimod at both acidic and physiological pH results in a blockage of FcRn-mediated recycling of IgGs.

Efgartigimod has a molecular weight of about 54 kDa, which is about one-third the molecular weight of full-length IgG (MW ca. 150 kDa). Thus, 10 mg efgartigimod is about 185 nmol, such that a dose of 10 mg efgartigimod/kg body weight corresponds to about 185 nmol efgartigimod/kg body weight and a dose of 25 mg efgartigimod/kg of body weight corresponds to about 462.5 nmol efgartigimod/kg body weight. In contrast, a dose of 10 mg full-length IgG antibody/kg body weight corresponds to about 67 nmol/kg body weight. Furthermore, a 1000 mg fixed dose of efgartigimod corresponds to a fixed dose of about 18500 nmol of efgartigimod while a 2000 mg fixed dose of efgartigimod corresponds to a fixed dose of about 37000 nmol of efgartigimod.

Due to its increased affinity for FcRn at both acidic and neutral pH, efgartigimod blocks the FcRn/IgG complex from forming, which results in degradation of endogenous IgGs, including autoantibodies that cause IgG-mediated autoimmune diseases. This blocking of FcRn by efgartigimod results in a rapid and profound reduction in autoantibody levels, which underlies the therapeutic strategy for the treatment of autoimmune indications where IgG autoantibodies are expected to have a central role in the disease pathology, e.g., conditions such as pemphigus (PV and PF).

rHuPH20

Efgartigimod is under development for both the intravenous (IV) and subcutaneous (SC) administration route. For SC administration, in certain embodiments efgartigimod may be administered alone. Alternatively, for SC administration, in certain embodiments efgartigimod may be administered co-formulated with hyaluronidase, for example, in particular, rHuPH20. The co-formulated material will allow dosing of higher volumes.

rHuPH20 is the active ingredient of Halozyme's commercial product HYLENEX® recombinant (hyaluronidase human injection), referred to as HYLENEX®, which was approved by FDA for marketed use in the US in December 2005. HYLENEX® is a tissue permeability modifier indicated as an adjuvant in SC fluid administration for achieving hydration, to increase the dispersion and absorption of other injected drugs, and in SC urography, for improving resorption of radiopaque agents.

rHuPH20 is a recombinant enzyme human hyaluronidase produced by genetically engineered Chinese hamster ovary (CHO) cells containing a deoxyribonucleic plasmid encoding a soluble fragment of human hyaluronidase (posterior head protein 20 [PH20]).

The HZ202 rHuPH20 DS is currently registered in HYLENEX® and other biologic drug products co-formulated with rHuPH20 DS. As such, in certain embodiments HZ202 rHuPH20 DS is used in the efgartigimod/rHuPH20 co-formulated product for SC administration (i.e., efgartigimod PH20 SC).

SC injection volumes are typically limited to 2.5 mL due to concerns regarding injection pain associated with larger volumes. It has been demonstrated that rHuPH20 offers a solution to the volume limitation associated with fast SC injections. rHuPH20 acts locally and transiently to depolymerize hyaluronan, a gel-like substance found in the subcutaneous layer of the skin. This results in decreased resistance to fluid flow and may increase dispersion and absorption of injected medicines and fluids, allowing for larger volume to be injected with limited swelling or pain. It has been shown that rHuPH20 allows for the fast absorption of a relatively large volume (10 mL) when administered SC. Shpilberg O et al., *Br J Cancer.* 2013; 109 (6): 1556-1561. Very little injection site swelling was observed when 10 mL of IgG solution was administered SC using rHuPH20 at 2,000 U/mL, whereas a large injection site swelling was observed when 10 mL of IgG solution was injected without rHuPH20. Shpilberg O et al., *Br J Cancer.* 2013; 109 (6): 1556-1561.

rHuPH20 is transiently acting and is not systematically absorbed. It has been demonstrated to exert no long-term local effects. rHuPH20 has a half-life in the skin of less than 30 minutes. Hyaluronan levels in subcutaneous tissues return to normal within 24 to 48 hours because of the rapid natural turnover of hyaluronan.

rHuPH20 is approved for SC administration in co-formulations with other active ingredients (RITUXAN HYCELA®/MABTHERA® SC [rituximab] for Non-Hodgkin's lymphoma (NHL) and chronic lymphocytic leukemia (CLL) and HERCEPTIN HYLECTA™/HERCEPTIN® SC [trastuzumab] in the US and Europe with an enzyme concentration of 2,000 U/mL and an injectable volume that ranges from 5 to 13.4 mL.

Methods

Provided herein are methods for treating pemphigus using an FcRn antagonist. In certain embodiments, the pemphigus is pemphigus vulgaris (PV). In certain embodiments, the pemphigus is pemphigus foliaceus (PF). In certain embodiments, the pemphigus can include both PV and PF. In certain embodiments, the FcRn antagonist is efgartigimod. An important goal and feature of the methods disclosed herein is the reduction or even the elimination of the use of potentially toxic agents such as corticosteroids (e.g., prednisone) and Rituxan in the treatment of pemphigus. Another important goal and feature of the methods disclosed herein is rapid onset of disease control. Yet another important goal and feature of the methods disclosed herein is achievement of long-lasting complete remission on minimal treatment, preferably without the use of potentially toxic agents such as corticosteroids (e.g., prednisone) and Rituxan.

An aspect of the disclosure is a method of treating pemphigus, comprising administering to a subject in need thereof an effective amount of a human neonatal Fc receptor (FcRn) antagonist, wherein the subject has (a) newly diagnosed pemphigus, (b) relapsing pemphigus, or (c) refractory pemphigus.

Relapsing pemphigus refers to the appearance of at least 3 new pemphigus lesions in a 4-week period that do not heal within a week, or extension of established lesions.

Refractory pemphigus refers to pemphigus that is not controlled on current therapy. In some embodiments, refractory pemphigus refers to pemphigus that is not controlled on corticosteroids. In some embodiments, refractory pemphigus refers to pemphigus that is not controlled on rituximab. In some embodiments, refractory pemphigus refers to pemphigus that is not controlled on rituximab plus corticosteroids. In some embodiments, refractory pemphigus refers to pemphigus that is not controlled on maximum corticosteroids. In some embodiments, refractory pemphigus refers to pemphigus that is not controlled on maximum rituximab. In some embodiments, refractory pemphigus refers to pemphigus that is not controlled on maximum rituximab plus maximum corticosteroids. In certain embodiments, refractory pemphigus refers to failure to reach disease control (see below) with full therapeutic doses of systemic treatments, e.g., prednisone 1.5 mg/kg/day for 3 weeks.

In some embodiments, the pemphigus comprises pemphigus vulgaris (PV), pemphigus foliaceus (PF), or both PV and PF. In some embodiments, the pemphigus comprises pemphigus vulgaris (PV). In some embodiments, the pemphigus comprises pemphigus foliaceus (PF). In some embodiments, the pemphigus comprises both pemphigus vulgaris (PV) and pemphigus foliaceus (PF). In some embodiments, the pemphigus consists of pemphigus vulgaris (PV). In some embodiments, the pemphigus consists of pemphigus foliaceus (PF). In some embodiments, the pemphigus consists of both pemphigus vulgaris (PV) and pemphigus foliaceus (PF).

In certain embodiments, the pemphigus may be characterized as mild, mild-to-moderate, moderate, severe (extensive), or moderate-to-severe pemphigus as classified by Pemphigus Disease Area Index (PDAI). In certain embodiments, the pemphigus may be characterized as mild pemphigus (e.g., a PDAI score of <15). In other embodiments, the pemphigus may be characterized as moderate pemphigus (e.g., a PDAI score of 15 to <45). In other embodiments, subject to be treated has severe pemphigus (e.g., a PDAI score of ≥ 45).

In some embodiments, the FcRn antagonist is administered once weekly until disease control. As used herein, "disease control" refers to no new lesions and established lesions beginning to heal.

In some embodiments, the FcRn antagonist is administered once weekly until complete remission. As used herein, "complete remission" refers to absence of new lesions and complete healing of established lesions (except for post-inflammatory hyperpigmentation or erythema from resolving lesions).

In some embodiments, the FcRn antagonist is administered intravenously. In some embodiments, the FcRn antagonist is administered intravenously once weekly at a dose of about 10 mg/kg to about 25 mg/kg. In some embodiments, the FcRn antagonist is administered intravenously once weekly at a dose of about 10 mg/kg. In some embodiments, the FcRn antagonist is administered intravenously once weekly at a dose of about 15 mg/kg. In some embodiments, the FcRn antagonist is administered intravenously once weekly at a dose of about 20 mg/kg. In some embodiments, the FcRn antagonist is administered intravenously once weekly at a dose of about 25 mg/kg. In some embodiments, the FcRn antagonist is administered intravenously once weekly at a dose of 10 mg/kg to 25 mg/kg. In some embodiments, the FcRn antagonist is administered intravenously once weekly at a dose of 10 mg/kg. In some embodiments, the FcRn antagonist is administered intravenously once weekly at a dose of 15 mg/kg. In some embodiments, the FcRn antagonist is administered intravenously once weekly at a dose of 20 mg/kg. In some embodiments, the FcRn antagonist is administered intravenously once weekly at a dose of 25 mg/kg.

In some embodiments, the FcRn antagonist is administered subcutaneously. In some embodiments, the FcRn antagonist is administered subcutaneously once weekly at a fixed dose of about 750 mg to about 1750 mg. In some embodiments, the FcRn antagonist is administered subcutaneously once weekly at a fixed dose of about 750 mg. In some embodiments, the FcRn antagonist is administered subcutaneously once weekly at a fixed dose of about 1000 mg. In some embodiments, the FcRn antagonist is administered subcutaneously once weekly at a fixed dose of about 1250 mg. In some embodiments, the FcRn antagonist is administered subcutaneously once weekly at a fixed dose of about 1500 mg. In some embodiments, the FcRn antagonist is administered subcutaneously once weekly at a fixed dose of about 1750 mg.

In some embodiments, the FcRn antagonist is administered subcutaneously once weekly at a fixed dose of 750 mg to 1750 mg. In some embodiments, the FcRn antagonist is administered subcutaneously once weekly at a fixed dose of 750 mg. In some embodiments, the FcRn antagonist is administered subcutaneously once weekly at a fixed dose of 1000 mg. In some embodiments, the FcRn antagonist is administered subcutaneously once weekly at a fixed dose of 1250 mg. In some embodiments, the FcRn antagonist is administered subcutaneously once weekly at a fixed dose of 1500 mg. In some embodiments, the FcRn antagonist is administered subcutaneously once weekly at a fixed dose of 1750 mg.

In some embodiments, the FcRn antagonist is administered subcutaneously once weekly at a dose of about 10 mg/kg to about 25 mg/kg. In some embodiments, the FcRn antagonist is administered subcutaneously once weekly at a dose of about 10 mg/kg. In some embodiments, the FcRn antagonist is administered subcutaneously once weekly at a dose of about 15 mg/kg. In some embodiments, the FcRn antagonist is administered subcutaneously once weekly at a dose of about 20 mg/kg. In some embodiments, the FcRn antagonist is administered subcutaneously once weekly at a dose of about 25 mg/kg.

In some embodiments, the FcRn antagonist is administered subcutaneously once weekly at a dose of 10 mg/kg to 25 mg/kg. In some embodiments, the FcRn antagonist is administered subcutaneously once weekly at a dose of 10 mg/kg. In some embodiments, the FcRn antagonist is administered subcutaneously once weekly at a dose of 15 mg/kg. In some embodiments, the FcRn antagonist is administered subcutaneously once weekly at a dose of 20 mg/kg. In some embodiments, the FcRn antagonist is administered subcutaneously once weekly at a dose of 25 mg/kg.

In some embodiments, the FcRn antagonist is administered in an induction phase and a consolidation phase. In certain embodiments, during the induction phase, the FcRn antagonist is administered once weekly or more frequently, e.g., twice a week or every other day. In certain embodiments, during the induction phase, the FcRn antagonist is administered less frequently than once weekly, e.g., once every other week. In certain embodiments, (i) during the induction phase the FcRn antagonist is administered once weekly and corticosteroid 0.5 mg prednisone/kg/day or equivalent is administered until disease control, and (ii) during the consolidation phase the FcRn antagonist dose is decreased and/or the FcRn antagonist dosing interval is lengthened, e.g., to once biweekly, and/or the corticosteroid dose is decreased and/or the corticosteroid dosing interval is lengthened, to an end-of-consolidation dose or dosing interval effective to prevent new lesions from appearing.

In certain embodiments, (i) during the induction phase the FcRn antagonist is administered once weekly and corticosteroid 0.5 mg prednisone/kg/day or equivalent is administered until disease control, and (ii) during the consolidation phase the FcRn antagonist dose is decreased and/or the FcRn antagonist dosing interval is lengthened, e.g., to once biweekly, to an end-of-consolidation dose or dosing interval effective to prevent new lesions from appearing.

In certain embodiments, (i) during the induction phase the FcRn antagonist is administered once weekly and corticosteroid 0.5 mg prednisone/kg/day or equivalent is administered until disease control, and (ii) during the consolidation phase the corticosteroid dose is decreased and/or the corticosteroid dosing interval is lengthened, to an end-of-consolidation dose or dosing interval effective to prevent new lesions from appearing.

In certain embodiments, (i) during the induction phase the FcRn antagonist is administered once weekly and corticosteroid 0.5 mg prednisone/kg/day or equivalent is administered until disease control, and (ii) during the consolidation phase the FcRn antagonist dose is decreased and/or the FcRn antagonist dosing interval is lengthened, e.g., to once biweekly, and the corticosteroid dose is decreased and/or the corticosteroid dosing interval is lengthened, to an end-of-consolidation dose or dosing interval effective to prevent new lesions from appearing.

In some embodiments, during the induction phase the FcRn antagonist is administered intravenously at a dose of about 10 mg/kg to about 25 mg/kg. In some embodiments, during the induction phase the FcRn antagonist is administered intravenously at a dose of about 10 mg/kg. In some embodiments, during the induction phase the FcRn antagonist is administered intravenously at a dose of about 15 mg/kg. In some embodiments, during the induction phase the FcRn antagonist is administered intravenously at a dose of about 20 mg/kg. In some embodiments, during the induction phase the FcRn antagonist is administered intravenously at a dose of about 25 mg/kg.

In some embodiments, during the induction phase the FcRn antagonist is administered intravenously at a dose of 10 mg/kg to 25 mg/kg. In some embodiments, during the induction phase the FcRn antagonist is administered intravenously at a dose of 10 mg/kg. In some embodiments, during the induction phase the FcRn antagonist is administered intravenously at a dose of 15 mg/kg. In some embodiments, during the induction phase the FcRn antagonist is administered intravenously at a dose of 20 mg/kg. In some embodiments, during the induction phase the FcRn antagonist is administered intravenously at a dose of 25 mg/kg.

In some embodiments, during the induction phase the FcRn antagonist is administered subcutaneously at a fixed dose of about 750 mg to about 1750 mg. In some embodiments, during the induction phase the FcRn antagonist is administered subcutaneously at a fixed dose of about 750 mg. In some embodiments, during the induction phase the FcRn antagonist is administered subcutaneously at a fixed dose of about 1000 mg. In some embodiments, during the induction phase the FcRn antagonist is administered subcutaneously at a fixed dose of about 1250 mg. In some embodiments, during the induction phase the FcRn antagonist is administered subcutaneously at a fixed dose of about 1500 mg. In some embodiments, during the induction phase the FcRn antagonist is administered subcutaneously at a fixed dose of about 1750 mg.

In some embodiments, during the induction phase the FcRn antagonist is administered subcutaneously at a fixed dose of 750 mg to 3000 mg. In some embodiments, during the induction phase the FcRn antagonist is administered subcutaneously at a fixed dose of 750 mg to 1750 mg. In some embodiments, during the induction phase the FcRn antagonist is administered subcutaneously at a fixed dose of 750 mg. In some embodiments, during the induction phase the FcRn antagonist is administered subcutaneously at a fixed dose of 1000 mg. In some embodiments, during the induction phase the FcRn antagonist is administered subcutaneously at a fixed dose of 1250 mg. In some embodiments, during the induction phase the FcRn antagonist is administered subcutaneously at a fixed dose of 1500 mg. In some embodiments, during the induction phase the FcRn antagonist is administered subcutaneously at a fixed dose of 1750 mg. In some embodiments, during the induction phase the FcRn antagonist is administered subcutaneously at a fixed dose of 2000 mg.

In some embodiments, during the induction phase the FcRn antagonist is administered subcutaneously at a dose of about 10 mg/kg to about 25 mg/kg. In some embodiments, the induction phase the FcRn antagonist is administered subcutaneously at a dose of about 10 mg/kg. In some embodiments, the induction phase the FcRn antagonist is administered subcutaneously at a dose of about 15 mg/kg. In some embodiments, the induction phase the FcRn antagonist is administered subcutaneously at a dose of about 20 mg/kg. In some embodiments, during the induction phase the FcRn antagonist is administered subcutaneously at a dose of about 25 mg/kg.

In some embodiments, during the induction phase the FcRn antagonist is administered subcutaneously at a dose of 10 mg/kg to 25 mg/kg. In some embodiments, the induction phase the FcRn antagonist is administered subcutaneously at a dose of 10 mg/kg. In some embodiments, the induction phase the FcRn antagonist is administered subcutaneously at a dose of 15 mg/kg. In some embodiments, the induction phase the FcRn antagonist is administered subcutaneously at a dose of 20 mg/kg. In some embodiments, during the induction phase the FcRn antagonist is administered subcutaneously at a dose of 25 mg/kg.

In some embodiments, during the consolidation phase the FcRn antagonist dosing interval is once weekly or less frequently. For example, in various certain embodiments, during the consolidation phase the FcRn antagonist dosing interval is once every 7, 8, 9, 10, 11, 12, 13, 14, 15, 16, 17, 18, 19, 20, or 21 days; or once every 2, 3, 4, 5 or 6 weeks. In various certain embodiments, during the consolidation phase the FcRn antagonist dosing interval is once every 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, or 7 to 21 days. In various certain embodiments, during the consolidation phase the FcRn antagonist dosing interval is once every 8 to 9, 8 to 10, 8 to 11, 8 to 12, 8 to 13, 8 to 14, 8 to 15, 8 to 16, 8 to 17, 8 to 18, 8 to 19, 8 to 20, or 8 to 21 days. In various certain embodiments, during the consolidation phase the FcRn antagonist dosing interval is once every 9 to 10, 9 to 11, 9 to 12, 9 to 13, 9 to 14, 9 to 15, 9 to 16, 9 to 17, 9 to 18, 9 to 19, 9 to 20, or 9 to 21 days. In various certain embodiments, during the consolidation phase the FcRn antagonist dosing interval is once every 10 to 11, 10 to 12, 10 to 13, 10 to 14, 10 to 15, 10 to 16, 10 to 17, 10 to 18, 10 to 19, 10 to 20, or 10 to 21 days. In various certain embodiments, during the consolidation phase the FcRn antagonist dosing interval is once every 11 to 12, 11 to 13, 11 to 14, 11 to 15, 11 to 16, 11 to 17, 11 to 18, 11 to 19, 11 to 20, or 11 to 21 days. In various certain embodiments, during the consolidation phase the FcRn antagonist dosing interval is once every 12 to 13, 12 to 14, 12 to 15, 12 to 16, 12 to 17, 12 to 18, 12 to 19, 12 to 20, or 12 to 21 days. In various certain embodiments, during the consolidation phase the FcRn antagonist dosing interval is once every 13 to 14, 13 to 15, 13 to 16, 13 to 17, 13 to 18, 13 to 19, 13 to 20, or 13 to 21 days. In various certain embodiments, during the consolidation phase the FcRn antagonist dosing interval is once every 14 to 15, 14 to 16, 14 to 17, 14 to 18, 14 to 19, 14 to 20, or 14 to 21 days. In various certain embodiments, during the consolidation phase the FcRn antagonist dosing interval is once every 15 to 16, 15 to 17, 15 to 18, 15 to 19, 15 to 20, or 15 to 21 days. In various certain embodiments, during the consolidation phase the FcRn antagonist dosing interval is once every 16 to 17, 16 to 18, 16 to 19, 16 to 20, or 16 to 21 days. In various certain embodiments, during the consolidation phase the FcRn antagonist dosing interval is once every 17 to 18, 17 to 19, 17 to 20, or 17 to 21 days. In various certain embodiments, during the consolidation phase the FcRn antagonist dosing interval is once every 18 to 19, 18 to 20, or 18 to 21 days. In various certain embodiments, during the consolidation phase the FcRn antagonist dosing interval is once every 19 to 20, or 19 to 21 days.

In some embodiments, during the consolidation phase the FcRn antagonist dosing interval is once weekly or every 2 weeks.

In some embodiments, the method further comprises a maintenance phase, wherein
(iii) during the maintenance phase the end-of-consolidation dose or dosing interval for the FcRn antagonist and/or the prednisone is continued until complete clearance of lesions.

In some embodiments, during the maintenance phase the FcRn antagonist dosing interval is once weekly or less frequently. For example, in various certain embodiments, during the maintenance phase the FcRn antagonist dosing interval is once every 7, 8, 9, 10, 11, 12, 13, 14, 15, 16, 17, 18, 19, 20, or 21 days; or once every 2, 3, 4, 5, or 6 weeks. In various certain embodiments, during the maintenance phase the FcRn antagonist dosing interval is once every 7 to 8, 7 to 9, 7 to 10, 7 to 11, 7 to 12, 7 to 13, 7 to 14, 7 to 15, 7 to 16, 7 to 17, 7 to 18, 7 to 19, 7 to 20, or 7 to 21 days. In various certain embodiments, during the maintenance phase the FcRn antagonist dosing interval is once every 8 to 9, 8 to 10, 8 to 11, 8 to 12, 8 to 13, 8 to 14, 8 to 15, 8 to 16, 8 to 17, 8 to 18, 8 to 19, 8 to 20, or 8 to 21 days. In various certain embodiments, during the maintenance phase the FcRn antagonist dosing interval is once every 9 to 10, 9 to 11, 9 to 12, 9 to 13, 9 to 14, 9 to 15, 9 to 16, 9 to 17, 9 to 18, 9 to 19, 9 to 20, or 9 to 21 days. In various certain embodiments, during the maintenance phase the FcRn antagonist dosing interval is once every 10 to 11, 10 to 12, 10 to 13, 10 to 14, to 15, 10 to 16, 10 to 17, 10 to 18, 10 to 19, 10 to 20, or 10 to 21 days. In various certain embodiments, during the maintenance phase the FcRn antagonist dosing interval is once 10 every 11 to 12, 11 to 13, 11 to 14, 11 to 15, 11 to 16, 11 to 17, 11 to 18, 11 to 19, 11 to 20, or 11 to 21 days. In various certain embodiments, during the maintenance phase the FcRn antagonist dosing interval is once every 12 to 13, 12 to 14, 12 to 15, 12 to 16, 12 to 17, 12 to 18, 12 to 19, 12 to 20, or 12 to 21 days. In various certain embodiments, during the maintenance phase the FcRn antagonist dosing interval is once every 13 to 14, 13 to 15, 13 to 16, 13 to 17, 13 to 18, 13 to 19, 13 to 20, or 13 to 21 days. In various certain embodiments, during the maintenance phase the FcRn antagonist dosing interval is once every 14 to 15, 14 to 16, 14 to 17, 14 to 18, 14 to 19, 14 to 20, or 14 to 21 days. In various certain embodiments, during the maintenance phase the FcRn antagonist dosing interval is once every 15 to 16, 15 to 17, 15 to 18, 15 to 19, 15 to 20, or 15 to 21 days. In various certain embodiments, during the maintenance phase the FcRn antagonist dosing interval is once every 16 to 17, 16 to 18, 16 to 19, 16 to 20, or 16 to 21 days. In various certain embodiments, during the maintenance phase the FcRn antagonist dosing interval is once every 17 to 18, 17 to 19, 17 to 20, or 17 to 21 days. In various certain embodiments, during the maintenance phase the FcRn antagonist dosing interval is once every 18 to 19, 18 to 20, or 18 to 21 days. In various certain embodiments, during the maintenance phase the FcRn antagonist dosing interval is once every 19 to 20, or 19 to 21 days.

In some embodiments, during the maintenance phase the FcRn antagonist dosing interval is once weekly. In some embodiments, during the maintenance phase the FcRn antagonist dosing interval is once biweekly.

In some embodiments, the pemphigus goes into complete remission. In some embodiments, the complete remission is achieved at a corticosteroid dose of ≤about 5 mg prednisone/kg/day or equivalent. In some embodiments, the complete remission is achieved at a corticosteroid dose of ≤about 3 mg prednisone/kg/day or equivalent. In some embodiments, the complete remission is achieved at a corticosteroid dose of ≤about 2 mg prednisone/kg/day or equivalent. In some embodiments, the complete remission is achieved at a corticosteroid dose of ≤about 1 mg prednisone/kg/day or equivalent. In some embodiments, the complete remission is achieved at a corticosteroid dose of ≤about 0.5 mg prednisone/kg/day or equivalent. In some embodiments, the complete remission is achieved at a corticosteroid dose of ≤about 0.4 mg prednisone/kg/day or equivalent. In some embodiments, the complete remission is achieved at a corticosteroid dose of ≤about 0.3 mg prednisone/kg/day or equivalent. In some embodiments, the complete remission is achieved at a corticosteroid dose of ≤about 0.2 mg prednisone/kg/day or equivalent. In some embodiments, the complete remission is achieved at a corticosteroid dose of ≤about 0.1 mg prednisone/kg/day or equivalent.

In some embodiments, the complete remission is achieved at a corticosteroid dose of ≤5 mg prednisone/kg/day or equivalent. In some embodiments, the complete remission is achieved at a corticosteroid dose of ≤3 mg prednisone/kg/day or equivalent. In some embodiments, the complete remission is achieved at a corticosteroid dose of ≤2 mg prednisone/kg/day or equivalent. In some embodiments, the complete remission is achieved at a corticosteroid dose of ≤1 mg prednisone/kg/day or equivalent. In some embodiments, the complete remission is achieved at a corticosteroid dose of ≤0.5 mg prednisone/kg/day or equivalent. In some embodiments, the complete remission is achieved at a corticosteroid dose of ≤0.4 mg prednisone/kg/day or equivalent. In some embodiments, the complete remission is achieved at a corticosteroid dose of ≤0.3 mg prednisone/kg/day or equivalent. In some embodiments, the complete remission is achieved at a corticosteroid dose of ≤0.2 mg prednisone/kg/day or equivalent. In some embodiments, the complete remission is achieved at a corticosteroid dose of ≤0.1 mg prednisone/kg/day or equivalent.

In some embodiments, the complete remission is achieved at a corticosteroid dose of ≤about 20 mg prednisone/day or equivalent. In some embodiments, the complete remission is achieved at a corticosteroid dose of ≤about 15 mg prednisone/day or equivalent. In some embodiments, the complete remission is achieved at a corticosteroid dose of ≤about 10 mg prednisone/day or equivalent. In some embodiments, the complete remission is achieved at a corticosteroid dose of ≤about 5 mg prednisone/day or equivalent. In some embodiments, the complete remission is achieved at a corticosteroid dose of ≤about 3 mg prednisone/day or equivalent. In some embodiments, the complete remission is achieved at a corticosteroid dose of ≤about 2 mg prednisone/day or equivalent.

In some embodiments, the complete remission is achieved at a corticosteroid dose of ≤10 mg prednisone/day or equivalent. In some embodiments, the complete remission is achieved at a corticosteroid dose of ≤5 mg prednisone/day or equivalent. In some embodiments, the complete remission is achieved at a corticosteroid dose of ≤3 mg prednisone/day or equivalent. In some embodiments, the complete remission is achieved at a corticosteroid dose of ≤2 mg prednisone/day or equivalent.

In some embodiments, the complete remission is achieved without corticosteroid.

In some embodiments, the complete remission is maintained with a corticosteroid dose of ≤about 20 mg prednisone/day or equivalent. In some embodiments, the complete remission is maintained with a corticosteroid dose of ≤about 15 mg prednisone/day or equivalent. In some embodiments, the complete remission is maintained with a corticosteroid dose of ≤about 10 mg prednisone/day or equivalent. In some embodiments, the complete remission is maintained with a corticosteroid dose of ≤about 5 mg prednisone/day or equivalent. In some embodiments, the complete remission is maintained with a corticosteroid dose of ≤about 2 mg prednisone/day or equivalent. In some embodiments, the complete remission is maintained with a corticosteroid dose of ≤about 1 mg prednisone/kg/day or equivalent. In some embodiments, the complete remission is maintained with a corticosteroid dose of ≤about 0.5 mg prednisone/kg/day or equivalent. In some embodiments, the complete remission is maintained with a corticosteroid dose of ≤about 0.4 mg prednisone/kg/day or equivalent. In some embodiments, the complete remission is maintained with a corticosteroid dose of ≤about 0.3 mg prednisone/kg/day or equivalent. In some embodiments, the complete remission is maintained with a corticosteroid dose of ≤about 0.2 mg prednisone/kg/day or equivalent. In some embodiments, the complete remission is maintained with a corticosteroid dose of ≤about 0.1 mg prednisone/kg/day or equivalent.

In some embodiments, the complete remission is maintained with a corticosteroid dose of ≤20 mg prednisone/day or equivalent. In some embodiments, the complete remission is maintained with a corticosteroid dose of ≤15 mg prednisone/day or equivalent. In some embodiments, the complete remission is maintained with a corticosteroid dose of ≤ 10 mg prednisone/day or equivalent. In some embodiments, the complete remission is maintained with a corticosteroid dose of ≤5 mg prednisone/day or equivalent. In some embodiments, the complete remission is maintained with a corticosteroid dose of ≤2 mg prednisone/day or equivalent. In some embodiments, the complete remission is maintained with a corticosteroid dose of ≤1 mg prednisone/kg/day or equivalent. In some embodiments, the complete remission is maintained with a corticosteroid dose of ≤0.5 mg prednisone/kg/day or equivalent. In some embodiments, the complete remission is maintained with a corticosteroid dose of ≤0.4 mg prednisone/kg/day or equivalent. In some embodiments, the complete remission is maintained with a corticosteroid dose of ≤0.3 mg prednisone/kg/day or equivalent. In some embodiments, the complete remission is maintained with a corticosteroid dose of ≤0.2 mg prednisone/kg/day or equivalent. In some embodiments, the complete remission is maintained with a corticosteroid dose of ≤0.1 mg prednisone/kg/day or equivalent.

In some embodiments, the complete remission is maintained without corticosteroid.

In some embodiments, the subject is rituximab-refractory.

In some embodiments, the subject is corticosteroid-intolerant.

INCORPORATION BY REFERENCE

Each of the various publications cited in the foregoing description and the following examples is incorporated in its entirety herein by reference.

EXAMPLES

The invention will be further understood with reference to the following non-limiting experimental examples.

Example 1: Overview of a Phase 2 Clinical Trial of Efgartigimod in Treatment of Pemphigus Patients This example describes (ARGX-113-1701) a completed open-label, non-controlled, adaptive-design Phase 2 trial to evaluate the safety, PD, PK, efficacy, and conditions of use (dosage, frequency of administration at maintenance) of efgartigimod (variant Fc fragment of human IgG1 capable of blocking the neonatal Fc receptor (FcRn) for the treatment of pemphigus (vulgaris or foliaceus).

As described in more detail below, thirty-four (34) patients suffering from mild to moderate pemphigus vulgaris or foliaceus were enrolled into the trial. In sequential cohorts efgartigimod was dosed at 10 mg/kg or 25 mg/kg intravenously with various dosing frequency, as monotherapy or as add-on to low-dose oral prednisone.

The study enrolled adult male or female patients with clinical diagnosis of PV or PF, that has been confirmed by positive direct immunofluorescence, and positive indirect immunofluorescence and/or enzyme-linked immunosorbent assay (ELISA) with mild to moderate disease severity (Pemphigus Disease Area Index [PDAI]<45). The serum levels of autoantibodies directed against Dsg-3 and/or Dsg-1 antigen were identified at screening. Patients were newly diagnosed patients or relapsing patients off therapy or patients who relapsed despite taking oral prednisone at tapered dose with or without a conventional immunosuppressant. Treatment during the study consisted of efgartigimod monotherapy or efgartigimod in combination with oral prednisone or equivalent.

Efgartigimod demonstrated a favorable safety and tolerability profile in pemphigus patients, consistent with previous studies of efgartigimod. A strong association was shown between serum IgG level reduction, autoantibody level reduction and improvement of pemphigus disease area index (PDAI) scores and clinical outcomes. Efgartigimod, either as monotherapy or combined with prednisone, demonstrated fast onset of action and resulted in disease control in 90% of patients with a median time of 16 days. Optimized prolonged treatment with efgartigimod with low dose corticosteroids at a dose range of 0.06 to 0.48 mg/kg/day led to complete clinical remission within 2 to 41 weeks in 59% of patients.

The results of the trial indicated that efgartigimod was safe and induced a fast onset of action on disease activity and clinical outcomes, overall supporting efgartigimod as a promising therapy for pemphigus.

Example 2: Study Design

PV and PF patients with mild to moderate disease severity (PDAI<45 at baseline) (Rosenbach, M, et al., J Invest Dermatol, 2009. 129 (10): 2404-10) were enrolled in sixteen study centers in Europe and Israel. PV or PF diagnosis had to be confirmed by positive direct immunofluorescence and positive indirect immunofluorescence and/or Dsg-1/3

ELISA. Patients were either newly diagnosed, or relapsing. Patients having a treatment course of oral prednisone (or equivalent) and immunosuppressant at screening were includable, but the immunosuppressant had to be discontinued before baseline. Patients with a history of refractory disease to a second line therapy (e.g. IVIg, rituximab, plasma exchange/immunoadsorption) were excluded. In addition, use of therapies other than oral prednisone and conventional immunosuppressants, that could interfere with the clinical course of the disease (e.g. IV prednisolone bolus, dapsone, sulfasalazine, tetracyclines, nicotinamide, plasmapheresis/plasma exchange, immunoadsorption and IVIg) within 2 months prior to baseline visit were not permitted, neither the use of rituximab and other CD20-targeting biologics within 6 months prior to baseline visit. Patients with total IgG level<6 g/L in serum at screening were also excluded.

Figure 1:
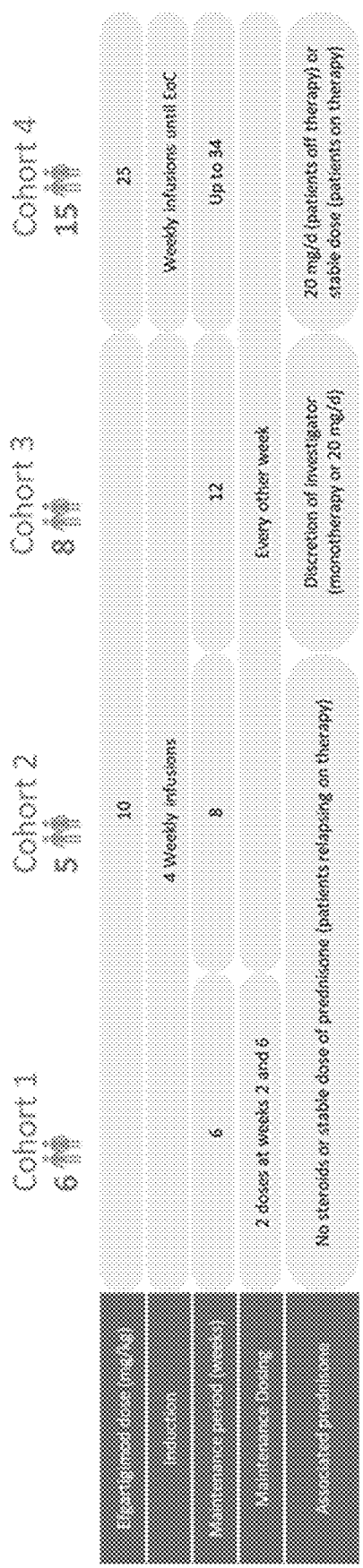
FIG. 1 depicts a schematic design of a completed Phase 2 trial (1701 study) of efgartigimod in patients with pemphigus vulgaris and foliaceus.

An open-label, non-controlled trial was conducted using an adaptive design with 4 sequential cohorts, in which efgartigimod, administered IV over a period of two hours, was tested at two different dosages (10 and 25 mg/kg body weight). At least 4 evaluable patients were to be enrolled in each cohort 1 to 3, and at least 10 evaluable patients in cohort 4. FIG. 1 presents a schematic of the design of this study. No pre-medication was required prior to efgartigimod infusion. Variable durations of the induction phase as defined by weekly infusions, and variable durations of the maintenance phase with a variable frequency of infusions (biweekly or four-weekly) were tested.

Overall, the trial included a 2-week screening period, a treatment period of 9 (cohort 1) to 34 weeks (cohort 4) as specified for each cohort, and a treatment-free follow-up period (8 weeks for cohort 1 and 10 weeks for cohorts 2 to 4). Before each administration, the total IgG serum level from the previous visit was verified, and no efgartigimod treatment was permitted if total IgG was <1.2 g/L, until recovery above this level. An Independent Data Monitoring Committee (IDMC) provided recommendations on the changes in treatment regimen between cohorts, based on safety and efficacy data from the previous cohorts. A minimum of 4 evaluable patients was included in each cohort.

During the treatment period, eligible patients were to receive efgartigimod via IV infusions and dosing schedule as follows. Cohort 1 patients had a treatment period of 9 weeks by receiving 4 weekly 10 mg/kg infusions and two 10 mg/kg maintenance infusions with a 2- and 4-week interval, respectively. Cohort 2 patients had a treatment period of 11 weeks and received 4 weekly 10 mg/kg infusions and 4 biweekly (i.e., dosing every other week) 10 mg/kg maintenance infusions. Cohort 3 patients had a treatment period of 15 weeks and received 4 weekly 10 mg/kg infusions and 6 biweekly 10 mg/kg maintenance infusions. Patients in cohort 4 receive weekly 25 mg/kg infusions until reaching end of consolidation (EoC), with a minimum of 5 weekly infusions, followed by biweekly 25 mg/kg maintenance infusions until the end of treatment at week 34. EoC is defined as the time at which no new lesions have developed for a minimum of 2 weeks and the majority (approximately 80%) of established lesions has healed.

In cohorts 1-3, efgartigimod was used from baseline either as monotherapy (in newly diagnosed patients and relapsing patients off therapy) or as add-on treatment to prednisone (in newly diagnosed patients on a first stable course of prednisone and in patients relapsing at a tapered prednisone dose). Under the latter circumstances, newly diagnosed patients received prednisone 20 mg/day and relapsing patients continued prednisone at the same tapered dose. In cohort 4, efgartigimod treatment was systematically initiated in association with prednisone, i.e., 20 mg/day in all newly diagnosed patients and relapsing patients off therapy, or at the tapered dose at which relapse occurred. In cohort 4, the oral prednisone dose could be tapered as of end of consolidation (EoC). Conversely, prednisone could be increased to 40 mg/day or at higher tapered doses according to clinical judgment, before study withdrawal in case of disease progression. No other systemic treatments for pemphigus were permitted during the study, whereas topical corticosteroids, analgesics, and supportive care for corticosteroid therapy (e.g., vitamin D, proton-pump inhibitors, specific diets) were allowed.

Descriptive statistical methods were used to analyze safety and efficacy data. Summaries were provided by cohort and/or efgartigimod dose.

As mentioned above, oral prednisone was the only treatment that was allowed in the study as concomitant treatment and rescue therapy. It consisted of addition of 20 mg/day of prednisone to efgartigimod treatment in newly diagnosed and off-therapy patients, and of an increase to the previous prednisone dose in relapsing patients. Patients under rescue treatment were kept in the study, unless disease progression led the patients to discontinue the study.

Example 3: Safety and Efficacy Assessment

The primary endpoint was safety, assessed throughout the course of the study, including the frequency and severity of treatment-emergent adverse events (TEAEs), serious adverse events (SAEs), vital signs, ECG (electrocardiogram) parameters, physical examination abnormalities and routine clinical laboratory assessments (hematology, biochemistry, urinalysis). As additional safety parameter, total IgG levels in serum were measured at each visit.

Efficacy endpoints included pemphigus disease activity index (PDAI) assessment; time to DC, defined as no new lesions, established lesions starting to heal; time until relapse, defined as the appearance of 3 or more new lesions a month that do not heal spontaneously within 1 week, or as the extension of established lesions, evaluated from any visit following DC; time to EoC, defined as the time at which no new lesions have developed for a minimum of 2 weeks, and approximately 80% of lesions have healed; time to complete CR, defined by the absence of new lesions and established lesions completely healed (except for post-inflammatory hyperpigmentation or erythema from resolving lesions); and time to complete clinical remission under minimal therapy (CRmin), defined by a prednisone dose of 10 mg/day or less for at least 8 weeks.

Other secondary endpoints included the evaluation of the pharmacodynamic (total IgG and subtypes, anti-Dsg-1 and -3 autoantibodies) and pharmacokinetics parameters., and immunogenicity (incidence of anti-drug antibodies (ADA)). Measurement of serum levels of anti-Dsg-1 and anti-Dsg-3 autoantibodies was performed with anti-Desmoglein-1 and -3 IgG ELISA test kits (Euroimmun, Germany), respectively.

Example 4: Pemphigus Study Population and Patient Disposition

Figure 2:
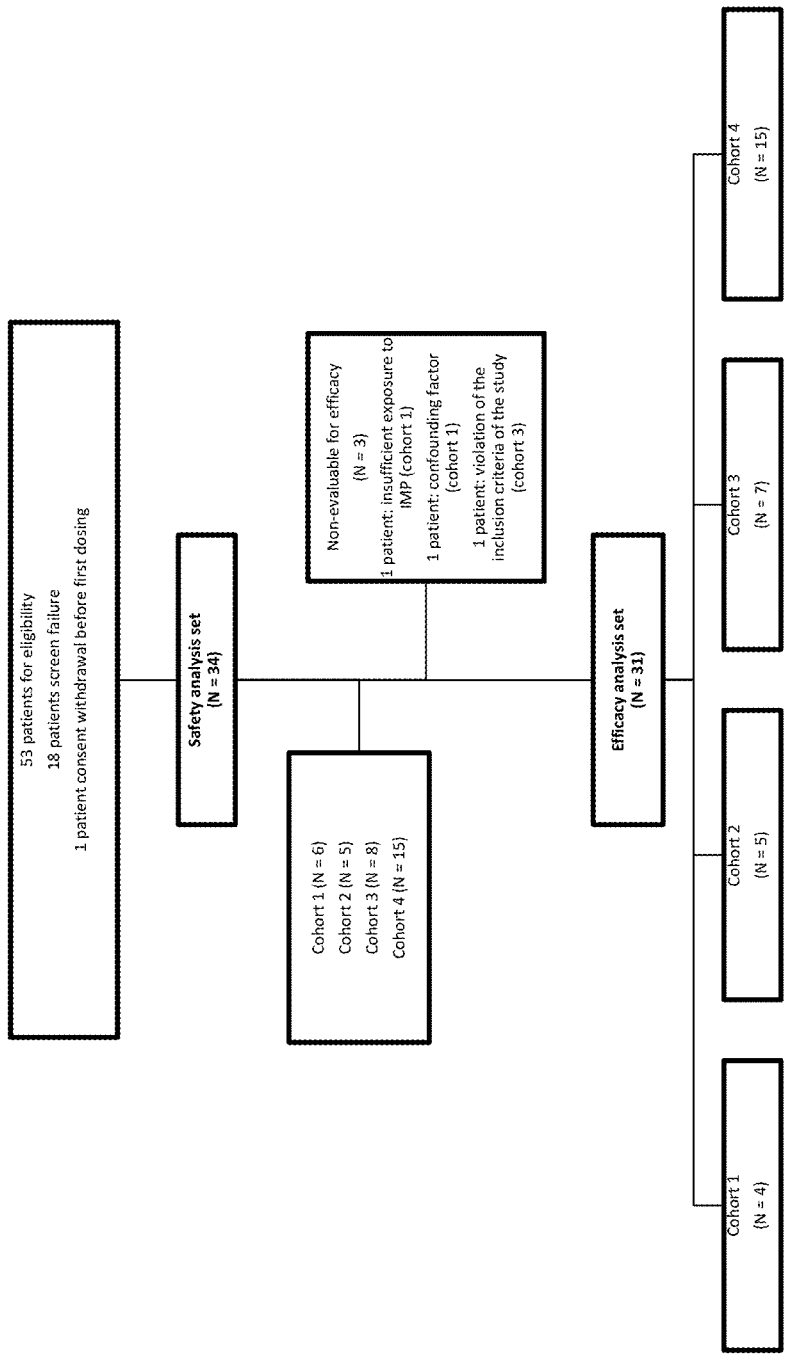
FIG. 2 is a flow chart indicating patients' disposition for safety dataset analysis and efficacy dataset analysis and their assignments to cohorts in the Phase 2 trial (1701 study) of efgartigimod in patients with pemphigus vulgaris and foliaceus.

Fifty-three (53) patients were screened for eligibility, 35 were eligible to participate, and 34 were enrolled in the trial (one patient withdrew consent before baseline), which constituted the safety analysis set (FIG. 2). Twelve study centers in 5 countries (Germany, Hungary, Israel, Italy, Ukraine)

treated at least 1 patient for the study. Six patients were assigned to cohort 1, 5 patients were assigned to cohort 2, 8 patients were assigned to cohort 3, and 15 patients were assigned to cohort 4.

Results in this study include those from a first interim analysis (data cutoff Nov. 7, 2019, report date Feb. 21, 2020), those from a second (later) interim analysis (data cutoff Mar. 25, 2020, report date Jul. 30, 2020), a third (later) interim analysis (data cutoff Jun. 24, 2020), and a final analysis (data cutoff Oct. 28, 2020). Unless indicated otherwise, data presented in the Examples are from the final analysis.

Example 5: Interim Analyses

Figure 3:
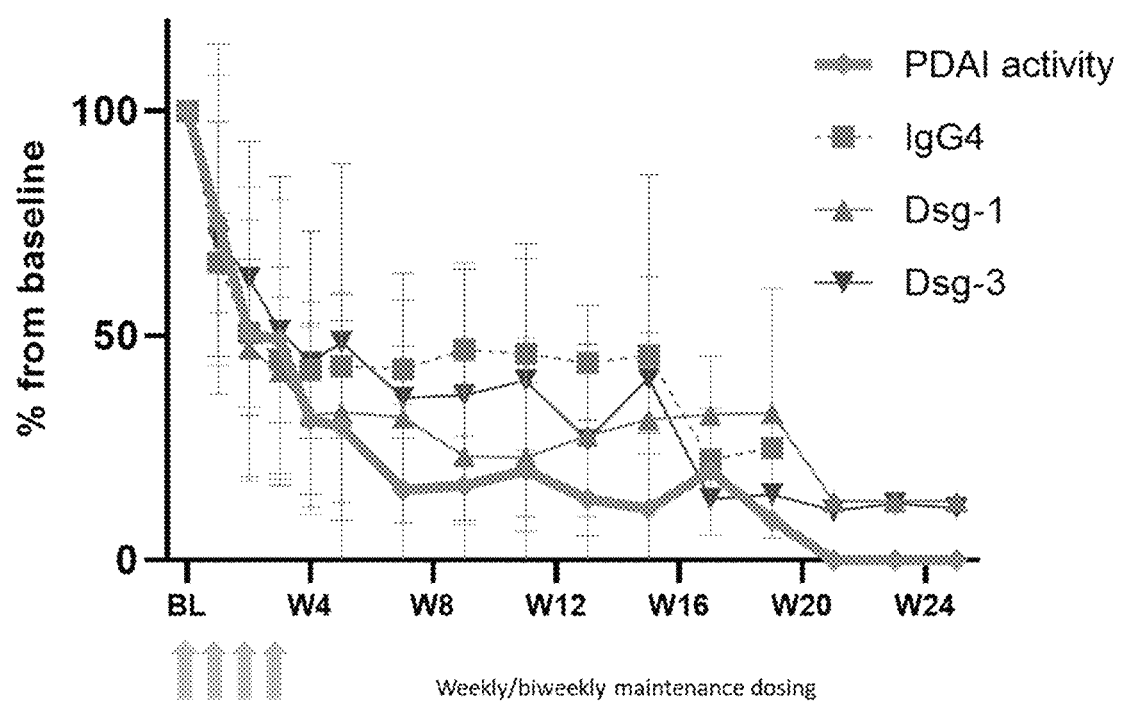
FIG. 3 is a summary slide of the first interim results of a Phase 2 trial (1701 study) of efgartigimod in pemphigus patients. Cut-off date on the data from the Phase 2 trial is: 7 Nov. 2019. The patient population included pemphigus vulgaris (PV) patients of the mucosal dominant (N=8), mucocutaneous (N=10), and cutaneous (N=1) subtypes, as well as pemphigus foliaceus (PF) patients (N=4). Patients exhibited a decrease in Pemphigus Disease Area Index (PDAI) activity which correlated with a reduction of pathogenic IgG4 autoantibodies (DSG-1 and DSG-3) following initial induction dosing of efgartigimod and subsequent weekly or biweekly maintenance dosing with efgartigimod.

As summarized in FIG. 3, an initial Interim analysis of results from this Phase 2 study (data cutoff Nov. 7, 2019) indicated the following:
(i) 23 patients enrolled in adaptive trial evaluating 10 mg/kg and 25 mg/kg IV efgartigimod with multiple dosing regimens established a clear correlation between pathogenic IgG reduction and Pemphigus Disease Area Index score improvement;
(ii) 83% of patients overall achieved disease control, with 78% within four weeks;
(iii) Rapid disease control was associated with both monotherapy and combination with low-dose prednisone;
(iv) 70% (5/7) of patients who received optimized dosing of efgartigimod with concomitant corticosteroids achieved clinical remission (CR); five CRs were observed within 2-10 weeks; and 39% of all patients on combination therapy achieved CR; and
(v) Demonstrated potential to taper patients off concomitant corticosteroids after achieving CR.

A. Demographics and Baseline Characteristics

Interim patient demographics and baseline characteristics by analysis population are presented in Table 2A.

TABLE 2A

Demographics and Baseline Characteristics-Safety Analysis Set-Data from initial interim analysis (cut-off date on the data from the Phase 2 trial is: 7 Nov. 2019)

| Parameter | Safety Analysis Set Locked Data (N = 16) n (%) | Safety Analysis Set All Available Data (N = 26) n (%) |
|---|---|---|
| Age at Screening (years) | | |
| n | 16 | 26 |
| mean (std) | 52.8 (14.21) | 49.7 (14.58) |
| median | 51.0 | 49.0 |
| range (min, max) | 29, 78 | 22, 78 |
| Gender | | |
| Male | 4 (25.0) | 9 (34.6) |
| Female | 12 (75.0) | 17 (65.4) |
| Pemphigus Vulgaris | 15 (93.8) | 21 (80.8) |
| Mucosal-dominant | 6 (40.0) | 8 (38.1) |
| Mucocutaneous | 8 (53.3) | 12 (57.1) |
| Cutaneous | 1 (6.7) | 1 (4.8) |
| Pemphigus Foliaceus | 1 (6.3) | 5 (19.2) |
| Baseline PDAI severity | | |
| Mild (PDAI <15) | 5 (31.3) | 9 (34.6) |
| Moderate (PDAI 15-44) | 11 (68.8) | 17 (65.4) |
| Newly diagnosed | 6 (37.5) | 11 (42.3) |
| Relapsing | 10 (62.5) | 15 (57.7) |
| ARGX-113 monotherapy at baseline | 11 (68.8) | 12 (46.2) |
| Patient took prednisone at baseline | 5 (31.3) | 14 (53.8) |

Patient demographics and baseline characteristics for a second interim analysis are presented in Table 2B. As of the cut-off date of Jun. 24, 2020, 26 patients with PV and 8 patients with PF were enrolled, of which 22 were females and 12 males. PV subtypes included mucosal-dominant (n=9), mucocutaneous (n=14) and cutaneous (n=3). 12 patients with mild baseline PDAI (<15) and 22 with moderate baseline PDAI (15-44) entered the study. Newly diagnosed patients comprised 14 patients and relapsing patients accounted for 20 patients. 11 patients began the trial with efgartigimod monotherapy while 23 started in association with low-dose prednisone at baseline.

TABLE 2B

Demographics and Baseline Characteristics-Safety and Efficacy Analysis Sets-Data from final analysis (cut-off date on the data from the Phase 2 trial is: 24 Jun. 2020)

| Baseline characteristics | Safety Analysis Set (N = 34) | Efficacy Analysis Set (N = 31) |
|---|---|---|
| Age (mean ± SD) | 51.5 ± 15.3 | 52.4 ± 15.5 |
| Sex (n (%)) | | |
| Male | 12 (35) | 10 (32) |
| Female | 22 (65) | 21 (68) |
| Pemphigus vulgaris (n (%)) | 26 (77) | 24 (77) |
| Mucosal-dominant | 9 (35) | 9 (38) |
| Mucocutaneous | 14 (54) | 12 (50) |
| Cutaneous | 3 (11) | 3 (12) |
| Pemphigus foliaceus (n (%)) | 8 (24) | 7 (23) |
| Disease History (n (%)) | | |
| Newly diagnosed | 14 (41) | 12 (39) |
| Relapsing | 20 (59) | 19 (61) |
| Baseline PDAI severity (n (%)) | | |
| Mild (PDAI <15) | 12 (35) | 12 (39) |
| Moderate (PDAI 15-44) | 22 (65) | 19 (61) |
| Baseline PDAI score (mean ± SD) (min, median, max score) | | |
| Overall population | 20.9 ± 11.5 (2.0, 20.4, 39.9) | 20.1 ± 11.8 (2.0, 19.0, 39.9) |
| Treatment initiated at Baseline (n (%)) | | |
| Efgartigimod monotherapy | 11 (32) | 8 (26) |
| Efgartigimod + CS | 23 (68) | 23 (74) |

B. Exposure

Extent of exposure (number of days of exposure to study drug and number of injections received by each patient) are presented by efgartigimod dose administered and overall for the Safety Analysis Set in Table 3.

In cohorts 1 to 3 patients received a dose of 10 mg/kg and in cohort 4 patients received a dose of 25 mg/kg.

TABLE 3

Trial ARGX-113-1701 Exposure-Safety Analysis Set-Data from initial interim analysis (cut-off date on the data from the Phase 2 trial is: 7 Nov. 2019)

| | Cohort 1 (10 mg/kg) (N = 6) | Cohort 2 (10 mg/kg) (N = 5) | Cohort 3 (10 mg/kg) (N = 8) | Cohort 4 (25 mg/kg) (N = 7) |
|---|---|---|---|---|
| Overall Exposure to study drug per patient (days) | | | | |
| n | 6 | 5 | 8 | 7 |
| mean (SD) | 38.3 (28.63) | 54.8 (32.75) | 100.1 (18.69) | 84.9 (61.43) |
| median | 39.0 | 78.0 | 106.0 | 85.0 |
| range (min, max) | 8, 66 | 16, 79 | 54, 110 | 8, 184 |
| Overall Exposure to study drug per patient (mg) | | | | |
| n | 6 | 5 | 8 | 7 |
| mean (SD) | 2939.33 (1616.196) | 3979.20 (1196.764) | 6489.38 (2274.694) | 16213.16 (9216.324) |
| median | 3025.00 | 3456.00 | 7132.50 | 13704.50 |
| range (min, max) | 1056.0, 5000.0 | 2880.0, 5600.0 | 2500.0, 9030.0 | 3100.0, 28800.0 |
| Overall Number of Infusions received per patient | | | | |
| n | 6 | 5 | 8 | 7 |
| mean (SD) | 4.0 (1.55) | 6.2 (2.49) | 9.3 (1.75) | 9.3 (5.22) |
| median | 4.0 | 8.0 | 10.0 | 10.0 |
| range (min, max) | 2, 6 | 3, 8 | 5, 10 | 2, 18 | n = number of patients; SD = standard deviation

C. Clinical Efficacy

Analyses of efficacy in this study were secondary objectives. All efficacy analyses were carried out using the efficacy analysis set. Efficacy assessments included an assessment of the extent of disease and evaluation of consensual clinical endpoints.

D. PDAI Activity Score

The change from baseline of the PDAI activity score at the end of each treatment phase (induction, maintenance, treatment-free follow up) for cohorts 1-3 is presented in Table 4. The changes from baseline of the PDAI activity at each visit by cohort is illustrated in FIG. 4 depicting the clinical efficacy assessed by the pemphigus disease area index (PDAI) activity in all 4 cohorts. Most patients demonstrated strong PDAI score improvements: In cohort 1 there was a correlation in IgG reduction with anti-Dsg reduction with PDAI score improvement, early DC (mono/combo) and suboptimal efgartigimod dosing in maintenance; in cohort 2 there was improved maintenance with efgartigimod dosing every other week. In cohort 3 all patients ultimately associated with prednisone, maintenance further improved symptoms, and EoC/CR was noted when associated with oral prednisone. In cohort 4, strong PDAI score improvements were noted, there was a high rate of EoC, and CR when prednisone was not tapered before CR.

FIG. 5 depicts clinical efficacy as assessed by PDAI activity in moderate severity patient cohorts 1-4. Most patients demonstrated strong PDAI score improvements: cohort 1 comprised three moderate patients (3 PV, 0 PF); cohort 2 comprised two moderate patients (2 PV, 0 PF); cohort 3 comprised four moderate patients (4 PV, 0 PF); and cohort 4 comprised five moderate patients (1 PV, 4 PF). The proposed patient population for the pemphigus Phase 3 trial is moderate to severe PV/PF.

FIG. 6 depicts PDAI activity scores over time in A) cohort 1, B) cohort 2, C) cohort 3, and D) cohort 4, as determined in the final analysis of the study.

TABLE 4

PDAI Activity Score Reduction: Percent Change from Baseline in Cohorts 1-3-Efficacy Analysis Set-Data from initial interim analysis (cut-off date on the data from th ePhase 2 trial is: 7 Nov. 2019)

| | | Cohort 1 (10 mg/kg) | Cohort 2 (10 mg/kg) | Cohort 3 (10 mg/kg) |
|---|---|---|---|---|
| End of induction phase*1 | N | 3 | 3 | 7 |
| | mean (std) | −53.77 (18.691) | 88.20 (280.274) | −58.26 (65.130) |
| | median | −46.50 | −54.40 | −83.30 |
| | range (min, max) | −75.0, −39.8 | −92.1, 411.1 | −100.0, 80.0 |
| | 95% CI | −100.2, −7.3 | −608.0, 784.4 | −118.5, 2.04 |
| End of maintenance phase*2 | N | 3 | 3 | 7 |
| | mean (std) | −23.83 (30.534) | −56.20 (43.139) | −15.49 (184.246) |
| | median | −25.50 | −69.80 | −91.70 |
| | range (min, max) | −53.5, 7.5 | −90.9, −7.9 | −100.0, 400.0 |
| | 95% CI | −99.7, 52.0 | −163.4, 51.0 | −185.9, 154.94 |

TABLE 4-continued

PDAI Activity Score Reduction: Percent Change from Baseline in Cohorts
1-3-Efficacy Analysis Set-Data from initial interim analysis (cut-off date
on the data from th ePhase 2 trial is: 7 Nov. 2019)

|  |  | Cohort 1 (10 mg/kg) | Cohort 2 (10 mg/kg) | Cohort 3 (10 mg/kg) |
|---|---|---|---|---|
| End of treatment-free follow-up*3 | N | 3 | 2 | 6 |
|  | mean (std) | 9.90 (80.158) | −76.30 (8.910) | −33.05 (130.366) |
|  | median | −16.80 | −76.30 | −89.15 |
|  | range (min, max) | −53.5, 100.0 | −82.6, −70.0 | −100.0, 230.0 |
|  | 95% CI | −189.2, 209.0 | −156.3, 3.7 | −169.9, 103.84 |

*1 End of induction phase cohorts 1 to 3 (visit 5)
*2 End of maintenance phase*2 (cohort 1-M2; cohort 2-M4; cohort 3-M6)
*3 End of treatment-free follow-up (cohort 1-FU2; cohorts 2 and 3-FU3)
CI = confidence interval Within the induction period comprising 4 weekly infusions (cohorts 1, 2 and 3), PDAI activity was reduced, ranging from median change −46.5% (range −39.8%, −75%) in cohort 1 to median change −83.3% (range −100%, +80.0%) in cohort 3 after 4 weeks. At the end of the maintenance period, the PDAI activity in cohort 1 (2 infusions with a 2-week then a 4-week interval) tended to be higher than at the end of induction (median change −25.5% at the end of maintenance and median change −46.5% at the end of induction). In cohort 2 (4 infusions every other week), the PDAI activity was decreased to a greater extent at the end of maintenance compared to the end of induction (median change −69.8% at the end of maintenance compared to median change −54.4% at the end of induction). In cohort 3 (6 infusions every other week), PDAI activity was further decreased compared to the preceding cohorts, with a median change of −91.7% at the end of maintenance (compared to end of induction median change −83.3%).

During the treatment-free follow up, the PDAI activity in cohort 1 tended to return to its baseline value (median change −16.8%), whereas in cohorts 2 and 3 the PDAI activity remained stable at a similar level compared to the end of maintenance (median change −76.30% and −89.2%, respectively).

Figure 4A:
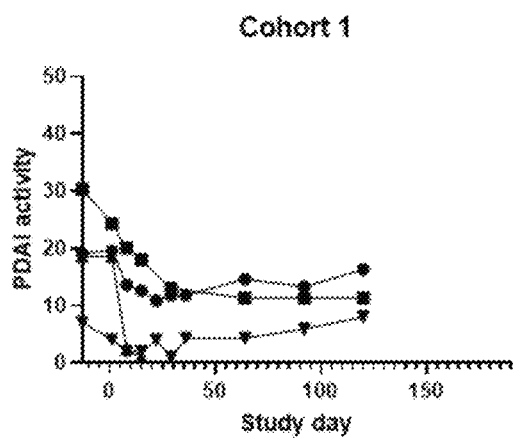
FIGS. 4A-4D depict the clinical efficacy of efgartigimod as assessed by the Pemphigus Disease Area Index (PDAI) activity in 4 patient cohorts of the Phase 2 trial (initial interim results in 1701 study; cut-off date on the data from the Phase 2 trial is: 7 Nov. 2019). Cohort 1:10 mg/kg i.v., induction of efgartigimod=4 infusions (3 weeks), maintenance=2 infusions (6 weeks). Cohort 2: Screening: allow suitable oral prednisone to stabilize disease activity at screening, to be continued at stable dose at induction (optional measure). Induction: Same dose (10 mg/kg i.v.) and frequency. Maintenance: two additional administrations, extend maintenance duration to 8 weeks (biweekly administration for 8 weeks). Follow-up: one additional follow-up visit (week 2) and prolongation to 10 weeks. Cohort 3: Screening: Allow suitable oral prednisone to stabilize disease activity at screening, may be further increased at any post-baseline visit (all patients). Induction: Same dose (10 mg/kg i.v.) and frequency. Maintenance: 2 additional administrations, extend maintenance duration to 12 weeks (dosing every two weeks for 12 weeks). Treatment-free follow-up 10 weeks.
Figure 4B:
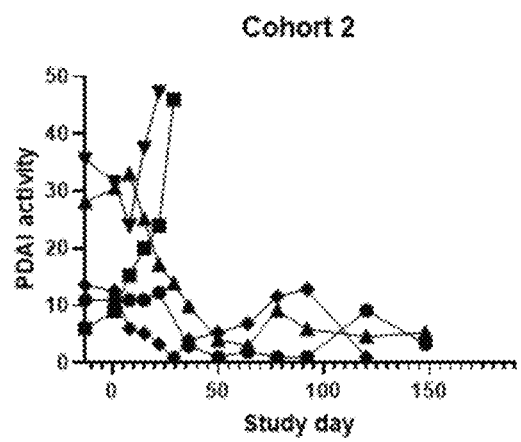
Figure 4C:
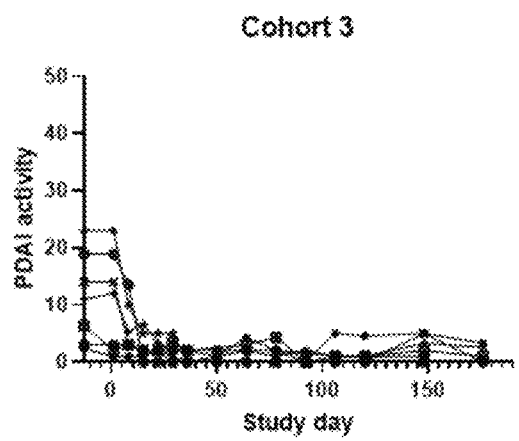
Figure 4D:
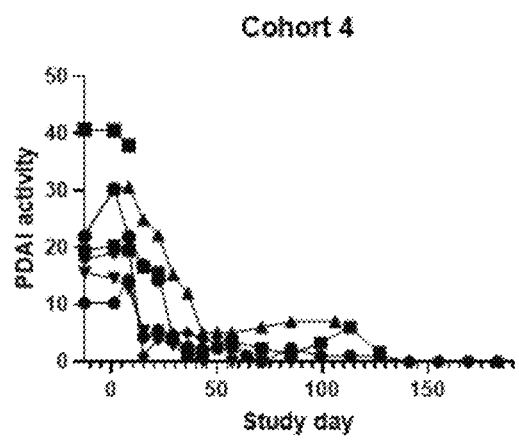

In cohort 4, the treatment regimen consisting of an induction treatment period with weekly administration until end of consolidation and maintenance treatment period with administration every other week until week 34 was different as compared to cohorts 1-3. Accordingly, no direct comparison of the periods with cohorts1-3 can be made. The time course of PDAI activity in cohort 4 is presented in FIG. 4D, showing a median change of PDAI activity of −73.7% (range −51.5%, −80.3%) after 4 weeks.

E. Clinical Outcomes

Clinical outcomes include assessment of disease control (DC), complete clinical remission (CR), and relapse.

E.1. Disease Control

In the efficacy analysis population (n=31), 28 patients (90.3%) reached DC during the study and 24 patients (77.4%) had DC within the 4-week induction period (Table 5). DC distributed equally between patients of mild and moderate severity, newly diagnosed and relapsing, and under monotherapy and concomitant prednisone. The median time to DC was as early as 15.0 days (range: 8-30 days) for patients in cohorts 1 to 3 and 29 days (range 9-30 days) in cohort 4. Conversely, 2 patients in cohort 2 experienced disease progression, which resulted in early discontinuation in both cases.

TABLE 5

Trial ARGX-113-170-Incidence of Disease Control (Overall and During 4-weeks Induction Period) and Time to Disease Control-Efficacy Analysis Set-Data from initial interim analysis (cut-off date on the data from the Phase 2 trial is: 7 Nov. 2019)

| Subgroup | Cohort 1 (10 mg/kg) n (%) | Cohort 2 (10 mg/kg) n (%) | Cohort 3 (10 mg/kg) n (%) | Cohort 4 (25 mg/kg) n (%) | Overall n (%) |
|---|---|---|---|---|---|
| A |  |  |  |  |  |
| Overall | 4 | 5 | 7 | 7 | 23 |
| Achieved DC | 4 (100.0) | 3 (60.0) | 7 (100.0) | 5 (71.4) | 19 (82.6) |
| No DC | 0 | 2 (40.0) | 0 | 2 (28.6) | 4 (17.4) |
| Disease Severity at baseline |  |  |  |  |  |
| Mild (PDAI <15) | 1 (25.0) | 2 (40.0) | 3 (42.9) | 2 (28.6) | 8 (34.8) |
| Moderate (PDAI 15-44) | 3 (75.0) | 1 (20.0) | 4 (57.1) | 3 (42.9) | 11 (47.8) |
| Disease history |  |  |  |  |  |
| Relapsing Patients | 4 (100.0) | 1 (20.0) | 5 (71.4) | 3 (42.9) | 13 (56.5) |
| Newly Diagnosed Patients | 0 | 2 (40.0) | 2 (28.6) | 2 (28.6) | 6 (26.1) |

TABLE 5-continued

Trial ARGX-113-170-Incidence of Disease Control (Overall and During 4-weeks Induction Period) and Time to Disease Control-Efficacy Analysis Set-Data from initial interim analysis (cut-off date on the data from the Phase 2 trial is: 7 Nov. 2019)

ARGX-113

| | | | | | |
|---|---|---|---|---|---|
| monotherapy at baseline | 3 (75.0) | 3 (60.0) | 2 (28.6) | 0 5 (71.4) | 8 (34.8) |
| Patient took Prednisone at baseline | 1 (25.0) | 0 | 5 (71.4) | | 11 (47.8) |

B

| | | | | | |
|---|---|---|---|---|---|
| Disease control during 4-weeks Induction period | 4 4 (100.0) | 5 2 (40.0) | 7 7 (100.0) | 7 5 (71.4) | 23 18 (78.3) |
| Achieved DC No DC | 0 | 3 (60.0) | 0 | 2 (28.6) | 5 (21.7) |

| Summary Statistics for Time Variable Days to Control (days) | Cohort 1 to 3 (10 mg/kg) | Cohort 4 (25 mg/kg) |
|---|---|---|

C

| | | |
|---|---|---|
| Median time to DC | 15.0 | 22.5 |
| Range | (8-92) | (15-30) | n = number of patients

E.2. Complete Clinical Remission (CR)

CR was assessed in cohorts 3 and 4. In cohort 3, CR was based on a PDAI activity score of 0, in cohort 4 CR was assessed by the investigator. CR was observed in cohorts 3 and 4 where efgartigimod treatment was prolonged (11 weeks in cohort 3, up to 34 weeks in cohort 4) compared to previous cohorts, and prednisone was associated in all patients. In these two cohorts, 7 patients achieved CR: 5 patients (71.4%) in cohort 3, and 7 (46.7%) patients in cohort 4 (Table 6). Notably, 3 patients with a moderate disease severity reached CR in cohort 3.

Median time to CR was 36 days in cohort 3 (range: 13-93 days). In cohort 4, time to CR for the two patients was 44 and 72 days. The prednisone dose at the time of CR was found to be a contributing factor for achieving CR. Indeed, all patients reaching CR received a daily prednisone dose ranging from 0.06 to 0.48 mg/kg (median cohort 3:0.27 mg/kg/day, median cohort 4:0.28 mg/kg/day). Consequently, the combination of efgartigimod and a prednisone dose as low as 0.25-0.50 mg/kg per day may be sufficient for achieving CR.

TABLE 6

Trial ARGX-113-1701-Incidence of CR and Concomitant Prednisone Equivalent Dose at the Time of CR-Cohorts 3 and 4-Efficacy Analysis Set-Data from initial interim analysis (cut-off date on the data from the Phase 2 trial is: 7 Nov. 2019)

| Subgroup | Cohort 3 (10 mg/kg) n (%) | Cohort 4 (25 mg/kg) n (%) |
|---|---|---|

A

| | | |
|---|---|---|
| Overall | 7 | 7 |
| Achieved CR | 5 (71.4) | 2 (28.6) |
| No Clinical Remission | 2 (28.6) | 5 (71.4) |
| Disease Severity at baseline | | |
| Mild (PDAI <15) | 2 (28.6) | 2 (28.6) |
| Moderate (PDAI 15-44) | 3 (42.9) | 0 |
| Disease history | | |
| Relapsing Patients | 3 (42.9) | 1 (14.3) |
| Newly Diagnosed Patients | 2 (28.6) | 1 (14.3) |

| Parameter | Cohort 3 (10 mg/kg) (N = 7) | Cohort 4 (25 mg/kg) (N = 7) |
|---|---|---|

B

Prednisone Equivalent Dose (mg/day) on day before CR

| | | |
|---|---|---|
| n | 5 | 2 |
| mean (std) | 17.00 (6.71) | 20.00 (0.00) |
| median | 20.00 | 20.00 |
| range (min, max) | 5.00, 20.00 | 20.00, 20.00 |

Prednisone Equivalent Dose (mg/kg/day) on day before CR

| | | |
|---|---|---|
| N | 5 | 2 |
| mean (std) | 0.26 (0.15) | 0.34 (0.04) |
| median | 0.27 | 0.340.31, 0.36 |
| range (min, max) | 0.06, 0.48 | | n = number of patients

E.3. Relapse

Relapse is assessed in patients who reach DC (N=19) and was reported in 8 patients (42.1%; Table 7). It occurred more frequently early after DC (N=7) than later after CR (N=1). For patients in cohorts 1 to 3, median time to relapse after DC was 141 days (N=7; range 10-169) and 1 patient in cohort 4 had a relapse 63 days after DC. At the time of relapse, 3 patients were treated without concomitant prednisone, and 5 patients were on prednisone treatment at the mean dose of 0.14±0.06 mg/kg per day (median 0.17 mg/kg/day; range 0.07-0.20 mg/kg/day).

Relapse, which may occur immediately after DC is reached, relapse was actually only observed under bi-weekly efgartigimod regimen (N=4) or during the efgartigimod treatment-free follow up (N=4), whereas no patient on weekly efgartigimod administration had a relapse. According to these findings, it can be hypothesized that a weekly dosage regimen of efgartigimod is optimal for preventing relapse.

TABLE 7

Trial ARGX-113-1701-Incidence of Relapse and Concomitant Prednisone Equivalent Dose at the Time of Relapse-Efficacy Analysis Set-Data from initial interim analysis (cut-off date on the data from the Phase 2 trial is: 7 Nov. 2019)

| Subgroup | Cohort 1 (10 mg/kg) n (%) | Cohort 2 (10 mg/kg) n (%) | Cohort 3 (10 mg/kg) n (%) | Cohort 4 (25 mg/kg) n (%) | Overall n (%) |
|---|---|---|---|---|---|
| A | | | | | |
| Overall | 4 | 3 | 7 | 5 | 19 |
| Patient with relapse | 2 (50.0) | 2 (66.7) | 3 (42.9) | 1 (20.0) | 8 (42.1) |
| No relapse | 2 (50.0) | 1 (33.3) | 4 (57.1) | 4 (80.0) | 11 (57.9) |
| Disease Severity at baseline | | | | | |
| Mild (PDAI <15) | 1 (25.0) | 2 (66.7) | 1 (14.3) | 0 | 4 (21.1) |
| Moderate (PDAI 15-44) | 1 (25.0) | 0 | 2 (28.6) | 1 (20.0) | 4 (21.1) |
| Disease history | | | | | |
| Relapsing Patients | 2 (50.0) | 0 | 3 (42.9) | 1 (20.0) | 6 (31.6) |
| Newly Diagnosed Patients | 0 | 2 (66.7) | 0 | 0 | 2 (10.5) |

| Parameter | Cohort 1-3 (10 mg/kg) (N = 14) | Cohort 4 (25 mg/kg) (N = 7) |
|---|---|---|
| B Prednisone Equivalent Dose (mg/day) on day before Relapse | | |
| n | 7 | 1 |
| mean (std) | 5.86 (6.96) | 10.00 (NA) |
| median | 5.00 | 10.00 |
| range (min, max) | 0.00, 16.00 | 10.00, 10.00 |
| Prednisone Equivalent Dose (mg/kg/day) on day before Relapse | | |
| N | 7 | 2 |
| mean (std) | 0.07 (0.08) | 0.46 (0.13) |
| median | 0.07 | 0.46 |
| range (min, max) | 0.00, 0.18 | 0.36, 0.55 | n = number of patients

Efficacy Conclusions on Interim Clinical Outcomes

In summary, the pharmacodynamic effects (effects on IgG, anti Dsg-1 and -3 autoantibodies), clinical effects on the activity (PDAI), and clinical outcomes of the disease (disease control, clinical remission) support a potential beneficial effect on the treatment of PV and PF, in combination with low dose prednisone.

The therapeutic dose regimen to reach the optimal pharmacodynamic effect and clinical efficacy was weekly infusions 10 mg/kg efgartigimod (which translates into 1000 mg efgartigimod PH20 SC).

In conclusion, in this Phase 2 study, efgartigimod was observed to be a potential effective and safe treatment for PV and PF.

Example 6: Pharmacodynamics in Pemphigus Patients from Phase 2 Pemphigus Trial (ARGX-113-1701)

(a) Total IgG

Mean percent change from baseline of total IgG levels versus study days is presented in FIG. 7 and a summary of total IgG level reductions at the end of the induction phase, maintenance phase, and treatment-free follow-up phase is shown in Table 8.

Within the induction period comprising 4 weekly infusions in cohorts 1, 2 and 3, total IgG levels were reduced ranging from mean change from baseline of −55.0% to −67.9%. At the end of the maintenance period, total IgG levels in cohort 1 (2 infusions with a 2-week then a 4-week interval) had almost returned to baseline with a mean change from baseline of −4.37%. In cohorts 2 (4 infusions every other week) and 3 (6 infusions every other week) IgG levels remained suppressed to mean changes from baseline of −50.67% and −49.21% at the end of the maintenance phase, respectively. This indicated a more efficient suppression of total IgG levels after infusions every other week compared to the 2-week and 4-week interval of cohort 1.

At the end of the treatment-free follow up, the total IgG levels in cohort 1 (8 weeks after last dosing) were increased to +23.30% from baseline, and had almost returned to baseline to −9.65% and −6.25% from baseline respectively in cohorts 2 and 3 (both 10 weeks after last dosing).

In cohort 4, the treatment regimen consisting of an induction treatment period with weekly administration until end of consolidation and maintenance treatment period with administration every other week until week 34 was different as compared to cohorts 1-3. Accordingly, no direct comparison of the periods with cohorts 1-3 can be made. The time course of total IgG reduction in cohort 4 is presented in FIG. 7A, showing a mean change of −69.85% after 4 weeks. There is an apparent correlation between total IgG levels depicted in FIG. 7A and the PDAI activity score, depicted in FIGS. 7B and 7C.

The reduction of total IgG in PV in the Phase 2 study is shown in FIG. 8. PD profiles are shown for four weekly administrations of efgartigimod at 25 mg/kg. FIG. 8A shows the PD profile in PV, and FIG. 8B the PD profiles in healthy volunteers (HV) and PV. Similar PD profiles were observed between PV and HV, in line with expectations based on HV and modeling.

FIGS. 9A and 9B depict PD profiles for four weekly administrations of efgartigimod at 10 mg/kg. FIG. 9A shows the PD profile in PV, and FIG. 9B shows PD profiles in HV, PV, myasthenia gravis (MG) and ITP.

FIGS. 10A and 10B depict serum levels of total IgG in A) cohort 1-3, B) cohort 4. Data is from results of the Phase 2 trial (1701 study) of efgartigimod in pemphigus patients, date cut-off Jun. 24, 2020.

FIGS. 11A-11H depict serum levels of IgG subclasses IgG1, IgG2, IgG3, IgG4 in cohort 1-3 (A-D) and in cohort 4 (E-H). Data is from Phase 2 trial (1701 study) of efgartigimod in pemphigus patients, date cut-off Jun. 24, 2020.

TABLE 8

Total IgG Reduction: Percent Change from Baseline in Cohorts 1-3-Efficacy Analysis Set.

| | | Cohort 1 (10 mg/kg) | Cohort 2 (10 mg/kg) | Cohort 3 (10 mg/kg) |
|---|---|---|---|---|
| End of induction phase$^a$ | n | 2 | 3 | 7 |
| | mean (SD) | −55.00 (1.980) | −67.90 (5.205) | −63.44 (8.445) |
| | median | −55.00 | −66.70 | −60.70 |
| | range (min, max) | −56.4, −53.6 | −73.6, −63.4 | −74.4, −53.8 |
| | 95% CI | −72.8, −37.2 | −80.8, −55.0 | −71.3, −55.6 |
| End of maintenance phase$^b$ | n | 3 | 3 | 7 |
| | mean (SD) | −4.37 (8.372) | −50.67 (5.501) | −49.21 (10.006) |
| | median | −9.10 | −52.90 | −50.50 |
| | range (min, max) | −9.3, 5.3 | −54.7, −44.4 | −63.5, −36.8 |
| | 95% CI | −25.2, 16.4 | −64.3, −37.0 | −58.5, −40.0 |
| End of treatment-free follow-up$^c$ | n | 3 | 2 | 4 |
| | mean (SD) | 23.30 (22.761) | −9.65 (30.476) | −6.25 (22.809) |
| | median | 29.10 | −9.65 | −7.45 |
| | range (min, max) | −1.8, 42.6 | −31.2, 11.9 | −30.0, 19.9 |
| | 95% CI | −33.2, 79.8 | −283.5, 264.2 | −42.5, 30.0 |

$^a$End of induction phase for cohorts 1 to 3 at Visit 5.
$^b$End of maintenance phase (cohort 1-M2; cohort 2-M4; cohort 3-M6)
$^c$End of treatment-free follow-up (cohort 1-FU2; cohorts 2 and 3-FU3)
n = number of patients; CI = confidence interval In summary, pemphigus patients treated with efgartigimod exhibited an approximate 40% reduction in total serum IgG level following the first infusion as compared to baseline. The median pharmacodynamic (PD) effect at 10 mg/kg following 4 weekly infusions at day 29 was 62% reduction of total IgG, while for the 25 mg/kg dose it was 66%.

(b) Anti-Dsg Antibodies

Mean levels for anti-Dsg-3 and anti-Dsg-1 levels versus study days is presented in FIG. 12A-D. Serum levels of anti-Dsg-1-and-Dsg-3-specific IgG, the pathogenic autoantibodies in pemphigus which are predominantly of the IgG4 subclass, decreased in a similar fashion as total IgGs. A rapid clearance of pathogenic antibodies was observed and reached a median 61% reduction from baseline for anti-Dsg1 and 49% reduction for anti-Dsg3 antibodies at the end of the induction phase in all patients in the efficacy analysis set.

A clear association between pathogenic anti-Dsg-1/-3 autoantibody level reduction and improvement in the PDAI score was observed throughout the trial. At the end of 4 weeks of fixed dosing, the median reduction in PDAI activity scores was 75% (FIGS. 6A-6E). These observations were consistent regardless of pemphigus subtypes or disease history suggesting a potential broad utility of efgartigimod in pemphigus.

Due to variable numbers and frequencies of maintenance visits in cohorts 1 to 3, the median PD effect varied. The median PD effect in cohort 1 at the second maintenance visit was 9% IgG level reduction, in cohort 2 at the fourth maintenance visit 53% reduction, and in cohort 3 at the sixth maintenance visit 51% reduction. Patients in cohort 4 who achieved EoC and switched to biweekly dosing of efgartigimod had a sustained IgG level reduction at the level of approximately 50% for as long as biweekly infusions were maintained.

Similarly, the suppression of pathogenic antibodies could be maintained, albeit more heterogenous for anti-Dsg 3 antibodies. Extended treatment with efgartigimod in cohorts 3 and 4 translated into sustained PDAI activity reduction. 7 patients from cohort 3 completed the study with a median 78% PDAI activity score reduction (ranging between increase of 230 and reduction of 100) from baseline, and 4 patients from cohort 4 demonstrated a median 93% reduction (range 79, 100) from baseline at the end of study.

At the end of the treatment-free follow up (week 8 or week 10 post last drug administration), IgG levels rose back to normal, ranging between 39% reduction and 43% increase from baseline. For anti-Dsg1 autoantibodies the median change from baseline was 80% reduction and for anti-Dsg3 antibodies 43% reduction, overall depicting longer suppression of pathogenic antibodies as opposed to total IgG levels.

Example 7: Efgartigimod Monotherapy

Eight patients who received efgartigimod monotherapy at baseline exhibited a median 61% reduction in PDAI activity score (ranging between increase of 411 and reduction of 100) at the end of 4 weeks of fixed dosing as compared to a median 92% drop (ranging between increase of 50 and reduction of 100) in patients who additionally received prednisone at baseline. While concomitant low dose prednisone appeared to afford deeper PDAI activity score reduction, the evident effect of efgartigimod monotherapy suggested a large contribution of efgartigimod alone to clinical efficacy and a potential synergy of efgartigimod and low-dose corticosteroids.

Example 8: Final Clinical Outcomes

Fast onset of efgartigimod effects resulted in a rapid DC in 28 out of 31 patients (90%) with a median time to DC of 16 days (range 6, 92) (Table 9). DC was achieved in comparable proportions in PV and PF, in mild and moderate disease, in newly diagnosed and relapsing patients, and in patients receiving efgartigimod monotherapy or efgartigimod with concomitant prednisone at baseline. Prolonged maintenance therapy led to 13 complete clinical remissions (5 patients in cohort 3 and 8 patients in cohort 4). Occurrence of relapse was assessed in patients who reached DC (n=28) and was reported in 10 patients (36%).

TABLE 9

Incidence of disease control, clinical remission, and relapses in overall population and by subgroups from the efficacy analysis set.

|  | Disease Control | Clinical Remission | Relapse (from DC) |
|---|---|---|---|
| Overall, n (%) | 31 | 22 | 28 |
| yes | 28 (90) | 13 (59) | 10 (36) |
| no | 3 (10) | 9 (41) | 18 (64) |
| Median time to (range) | 16 (6-92) | 43 (13-287) | 87 (10-211) |
| Pemphigus Vulgaris, n/N (%) | 22/24 (92) | 9/15 (60) | 8/22 (36) |
| Pemphigus Foliaceus, n/N (%) | 6/7 (86) | 4/7 (57) | 2/6 (33) |
| Disease history, n/N (%) |  |  |  |
| Relapsing patients | 18/19 (95) | 7/13 (54) | 7/18 (39) |
| Newly Diagnosed patients | 10/12 (83) | 6/9 (67) | 3/10 (30) |

Fast onset of action of efgartigimod and high rate of EoC, triggering steroid tapering, overall led to a low prednisone consumption. Baseline median prednisone equivalent dose was 0.26 mg/kg/day (range 0.06, 0.54) for cohort 1-3 patients and 0.31 mg/kg/day (range 0.06, 0.61) for cohort 4 patients. At the time of EoC, only assessed in cohort 4, median concomitant prednisone dose was 0.28 mg/kg per day (range 0.22, 0.40 mg/kg/day, n=11). The median daily prednisone dose at the time cohort 3 and 4 patients achieved CR was 0.27 mg/kg/day (range 0.06-0.48).

Example 9: Pharmacokinetic Parameters

Pharmacokinetic parameters in patients treated IV with 10 mg/kg or 25 mg/kg of efgartigimod were in line with PK data in healthy volunteers dosed with 10 or 25 mg/kg [Ulrichts, P., et al., *Neonatal Fc receptor antagonist efgartigimod safely and sustainably reduces IgGs in humans*. J Clin Invest, 2018. 128 (10): p. 4372-4386.] and with PK data from other studies with 10 mg/kg [Howard, J. F., Jr., et al., *Randomized phase 2 study of FcRn antagonist efgartigimod in generalized myasthenia gravis*. Neurology, 2019. 92 (23): p. e2661-e2673 and Newland, A. C., et al., *Phase 2 study of efgartigimod, a novel FcRn antagonist, in adult patients with primary immune thrombocytopenia*. Am J Hematol, 2020. 95 (2): p. 178-187]. No clear deviation from proportionality could be observed. Negligible accumulation of efgartigimod was apparent after weekly or biweekly dosing as shown by consistent $C_{max}$ and $C_{trough}$. After the first weekly infusion of 10 or 25 mg/kg, mean $C_{max}$ observed at the end of the infusion was 178 µg/mL and 586 µg/mL, and median $C_{trough}$ observed at the end of the dosing interval was 9.34 µg/mL and 26.0 g/mL, respectively.

Example 10: Onset of Action, Depth of Response, and Conditions of Use for Achieving Complete Clinical Remission Data presented in this example are from the second interim analysis of Study ARGX-113-1701.

Clinical efficacy in pemphigus can be interpreted from PDAI score improvement, achieving defined clinical outcomes, the prednisone dose that is required to achieve or sustain clinical improvements, and prevention of relapse.

Rapid PDAI activity score improvements and achieving early DC (i.e., within 4 weeks) indicate fast onset effects of treatment with efgartigimod. Whereas, overall, 90% (28 of 31) of patients across treatment cohorts achieved DC and 77% (24 of 41) of patients across treatment cohorts achieved DC within 4 weeks, it was also noted that for a majority of the patients (N=16) DC was achieved after only 1 or 2 drug administrations, i.e., observed before or at visit 3. The median time to achieve DC was 15 days for patients treated with efgartigimod alone or 22 days in patients treated with efgartigimod in combination with oral prednisone.

An overall summary of clinical outcomes observed in each cohort is presented in Table 10. Clinical outcomes that were assessed in cohorts 1-3 included DC and relapse. First observed in cohort 3, patients also achieved complete healing of all lesions. A complete healing of all lesions was defined as CR and corresponds to a PDAI activity score of 0. Since in cohorts 1-3, according to the protocol, CR was not a clinical outcome recorded by the investigators, the occurrences of CR in cohort 3 are reported based on the recorded PDAI activity score. For cohort 4, the assessment of EoC and CR were added as clinical outcomes.

TABLE 10

Summary of Clinical Outcomes in Cohorts 1-4

| Outcome | Cohort 1 (N = 4) | Cohort 2 (N = 5) | Cohort 3 (N = 7) | Cohort 4 (N = 15)[a] |
|---|---|---|---|---|
| DC | 4 (100%) | 3 (60%) | 7 (100%) | 14 (93%) |
| EoC | NA | NA | NA | 11 (73%) |
| CR[b] | NA | NA | 5 (71%) | 7 (47%) |

CR = complete clinical remission; DC = disease control; EoC = end of consolidation; N = number of patients; NA = not applicable.
[a] Nine patients with an ongoing treatment at the time of interim analysis.
[b] CR calculated for cohort 3, investigator-assessed for cohort 4.

Since the prednisone dose at the time of CR was found to be a contributing factor for achieving CR, the rate of achieving CR was analyzed in patients receiving at least biweekly efgartigimod treatment in combination with intermediate oral prednisone dose (i.e., between 0.25 and 0.50 mg/kg/day). In total, 10 patients were treated with this dose regimen of which 70% (7 out of 10 patients) achieved CR; 3 patients in cohort 3 and 4 patients in cohort 4. Of note, 6 of the 7 patients who achieved CR on the treatment combination of at least biweekly efgartigimod dosing and oral prednisone equivalent dose between 0.25 and 0.50 mg/kg/day had received a stable non-tapered prednisone dose until CR was achieved.

In cohort 3, 3 patients treated with at least biweekly efgartigimod and prednisone 0.25-0.50 mg/kg/day achieved CR. The other 4 patients were treated without prednisone during the efgartigimod treatment phase (N=1), with prednisone 0.06-0.14 mg/kg/day (N=2), or prednisone was tapered while the patient was on weekly efgartigimod treatment (N=1; prednisone taper from 0.54 mg/kg/day to 0.13 mg/kg/day in 4 steps in 30 days; PDAI activity improvement).

In cohort 4, with a prolonged treatment duration and more standardized prednisone use, 93% (14 out of 15 patients) achieved DC, 73% (11 out of 15 patients) achieved EoC, and 47% (7 out of 15) achieved CR at the time of interim analysis. In addition to the 4 patients who achieved CR with at least biweekly efgartigimod and prednisone 0.25-0.50 mg/kg/day treatment combination, 3 patients achieved CR with slightly lower prednisone doses between 0.19 and 0.24 mg/kg/day.

CR on minimal therapy was defined as the absence of new or established lesions while the patient was receiving minimal therapy. Minimal therapy was defined as prednisone (or equivalent) at a dose of 10 mg/d or less and/or minimal adjuvant therapy for at least 2 months). CR on minimal therapy was the next disease outcome parameter after achievement of DC, EoC, and CR at any prednisone dose. For that reason, the daily prednisone doses and duration were analyzed for patients who had achieved CR. At the time of the second interim analysis, 3 patients had achieved CR on minimal therapy (one patient in cohort 3 and two patients in cohort 4). In addition, other patients had a sustained CR with a prednisone dose higher than 10 mg/day or for less than 8 weeks, had achieved EoC without achieving CR and prednisone was tapered to 10 mg/day or below, or had achieved EoC with a prednisone dose higher than 10 mg/day. A small number of patients had only achieved DC, had an insufficient clinical improvement, or discontinued the trial early.

Example 11: Discussion and Summary of Phase 2 Clinical Trial

During the efgartigimod induction phase, a sharp decrease of total serum IgG, IgG subclasses, and anti-Dsg1/3 autoantibodies was observed, by about 70% after a weekly treatment course of 2-3 weeks. In contrast, the B-cell depleting antibody rituximab demonstrates a slow and progressive decline in autoantibody titers within months, illustrating the critical differences in the modes of action between treatments. Blockade of FcRn with an FcRn antagonist, e.g., efgartigimod, causes an immediate degradation of autoantibodies responsible for keratinocyte detachment and keratinocyte destruction, while removal of autoantibody-producing B cells with a B-cell depleting agent, e.g., rituximab, has no immediate impact on circulating autoantibodies that have a typical half-life of about 3 weeks.

The utility of IVIg to saturate FcRn and thereby eliminate pathogenic antibodies has been rationalized in several studies. Grando, S A, et al., *Int Immunopharmacol*, 2020. 82:106385; Amagai, M, et al., *J Am Acad Dermatol*, 2009. 60 (4): 595-603. Moreover, because FcRn-deficient mice are resistant to experimental pemphigus (Li, N, et al., *J Clin Invest*, 2005. 115 (12): 3440-50) and expression of FcRn in keratinocytes has been documented (Cauza, K, et al., *J Invest Dermatol*, 2005. 124 (1): 132-9), it is plausible that protection from pathogenic autoantibodies via FcRn inhibition is mediated not only via induction of autoantibody degradation but also via direct blockade of FcRn in keratinocytes. Thus overall, because the disease activity is directly linked to the presence of pathogenic antibodies with multitudes of pathogenic actions, strategies precisely aiming at efficient depletion of pathogenic antibodies can have a profound impact on patients' response to therapy. In line with that, in all cohorts of the study, DC was achieved as fast as within 1-4 weeks in the vast majority of patients, with or without concomitant prednisone therapy. DC was similarly observed in patients with PV and PF, newly diagnosed and relapsing, and mild and moderate pemphigus.

The adaptive nature of the trial has led to the clear observation that the lowering of serum IgG was well maintained while on biweekly maintenance phase of efgartigimod, whereas the four-weekly dosing was insufficient to keep pathogenic autoantibodies suppressed enough and led to a recovery of IgG serum levels after 4 to 8 weeks. In the cohorts with prolonged efgartigimod treatment (cohort 3:11 weeks; cohort 4:34 weeks), CR could be reached within weeks (median: 6 weeks, range: 2 to 41 weeks), providing encouraging and supporting data to test the rate of CR and time to CR in a larger cohort of pemphigus patients in a phase 3 trial.

Notably, CR occurred optimally when associated with prednisone doses ranging from 0.06 to 0.48 mg/kg/day (median: 0.28 mg/kg/day), indicating an additive effect of prednisone to efgartigimod. Corticosteroids are known to regulate gene expression and broadly suppress many inflammatory genes acting on leukocyte movement, leukocyte function, and humoral factors as well as cytokine signaling. Moreover, beyond its well-described immunosuppressive effects, prednisone has been shown also to up-regulate expression of genes encoding keratinocyte adhesion molecules such as E-cadherin and desmogleins. Nguyen, V T, et al., *J Biol Chem*, 2004. 279 (3): 2135-46. Altogether, additive effects of prednisone in pemphigus patients receiving efgartigimod could be diversified.

Whereas anti-Dsg-1 and anti-Dsg 3 autoantibody reductions generally followed the course of total IgG level reductions, anti-Dsg 3 antibody levels were found to correlate less with IgG serum levels in some patients, without leading to increases in PDAI. This is in line with previous reports indicating that circulating anti-Dsg 3 antibody levels do not necessarily correlate with disease activity. Colliou, N, et al., *Sci Transl Med*, 2013. 5 (175): 175ra30. Treatment discontinuation resulted in a progressive return to normal IgG levels within 4 to 6 weeks, although many patients remained in disease remission or with a disease of low grade. Intriguingly, in several patients, autoantibody levels remained suppressed in the treatment-free follow-up while total IgG surged up as expected.

In this Phase 2 clinical trial, relapses occurred in 36% of the patients; they mainly consisted of early relapses, i.e., occurring before CR, and were observed during increased administration intervals of 2 or more weeks. Late relapses, i.e., after CR, occurred at biweekly dosage or during treatment-free follow-up. In contrast, no relapse occurred when patients were maintained at weekly efgartigimod dosage, suggesting that a weekly administration of efgartigimod beyond CR achievement may support prevention of the relapses.

Example 12: Rationale for Phase 3 Trials with Subcutaneous Administration

As pemphigus is a chronic disease, current therapies require chronic administration. In Phase 3 trials described in below, efgartigimod is administered with rHuPH20 via the subcutaneous (SC) route in a flat dose in a new highly concentrated formulation, which is more convenient for patients.

In order to allow for a convenient SC administration with efgartigimod to achieve the targeted exposure and PD effect, efgartigimod is co-formulated with rHuPH20. This compound is being used in co-formulations with approved therapeutic antibodies to facilitate SC injection with volumes larger than 2 mL. The use of rHuPH20 in combination with other therapeutic proteins typically increases the absorption rate of these proteins, albeit to different extents increased rate of absorption of efgartigimod by rHuPH20 is expected to increase the overall exposure to efgartigimod after SC administration allowing administration of a SC dose in an acceptable volume and duration of administration that targets an exposure that results in a close to the maximal PD effect.

A dose of 1000 mg efgartigimod SC is comparable to 10 mg/kg efgartigimod administered as IV infusion with respect to effect on IgG levels. The 10 mg/kg IV dose: 1) resulted in transient clinical efficacy in a Phase 2 trial in patients with ITP and a prolonged clinical effect in a Phase 2 trial in patients with generalized myasthenia gravis (gMG) following 4 weekly infusions; 2) was shown to result in close to saturated PD effect: Dosing higher or more frequently than weekly is not expected to result in an improved PD effect (i.e., further lowering of autoantibodies) and/or clinical effect and may be associated with a less optimal risk/benefit ratio. Dosing lower is expected to result in a lower PD effect and thus is likely to result in a less consistent and/or incomplete clinical response, which is undesirable given the serious and chronic manifestations of pemphigus; and 3) demonstrated a favorable safety profile in Phase 2 studies in patients with gMG and patients with ITP.

Example 13: Design of Phase 3 Clinical Trial with Subcutaneous Administration-ARGX-113-1904

ARGX-113-1904 is a randomized, double-blinded, placebo-controlled trial to investigate the efficacy, safety, and tolerability of efgartigimod PH20 SC in adult patients with pemphigus (vulgaris or foliaceus). The trial is given the acronym ADDRESS.

Efgartigimod PH20 SC is administered on day 1 and day 8 at a dose of 2000 mg, followed by weekly administrations of 1000 mg until complete remission on minimal therapy (CR on minimal therapy). Patients will also be administered placebo with the same regimen.

This trial intends to demonstrate that efgartigimod PH20 SC with an add-on therapy of low doses of oral prednisone is a possible treatment modality for PV and PF, the administration of which will lead to early disease remission at minimal prednisone dose. The efficacy, safety, patient outcome measures, tolerability, immunogenicity, PK, and PD of efgartigimod PH20 SC is evaluated in patients with PV or PF.

Overall Design

This is a prospective, multicenter, randomized, double-blinded, placebo-controlled trial to investigate the efficacy, safety, patient outcome measures, tolerability, immunogenicity, PK, and PD of efgartigimod PH20 SC in adult patients aged 18 to 80 years with PV or PF. See FIG. 13 for a diagram of the trial design. Enrolled patients are either those who are newly diagnosed or experiencing flare as follows:

Moderate to severe (PDAI activity score≥15) newly diagnosed and naïve to treatment.

Moderate to severe (PDAI activity score≥15) newly diagnosed while receiving a first course of oral prednisone (or equivalent). According to clinical judgment, the patient has shown no significant improvement of PV or PF signs for at least 2 weeks before baseline and is considered fit to start prednisone treatment at 0.5 mg/kg daily (qd) at baseline.

Moderate to severe (PDAI activity score≥15), experiencing flare, and off prednisone therapy±a conventional immunosuppressant (e.g., azathioprine, cyclophosphamide, methotrexate, mycophenolate mofetil). Conventional immunosuppressants are discontinued before baseline.

Moderate to severe (PDAI activity score≥15), experiencing flare, while receiving a tapered dose of oral prednisone (or equivalent), provided that prednisone (or equivalent) has been given at stable dose±a conventional immunosuppressant (e.g., azathioprine, cyclophosphamide, methotrexate, mycophenolate mofetil) and patients are fit to start prednisone treatment at 0.5 mg/kg qd at baseline. Conventional immunosuppressants are discontinued before baseline.

The trial comprises a screening period of up to 3 weeks, a treatment period of up to 30 weeks, and an 8-week follow-up period for patients who do not enroll into the open-label extension (OLE) trial ARGX-113-1905 (Example 14).

After confirmation of eligibility, patients are randomized in a 2:1 ratio to receive efgartigimod PH20 SC or placebo, as follows:

Efgartigimod PH20 SC is administered on day 1 and day 8 at a dose of 2000 mg, followed by weekly administrations of 1000 mg until CR on minimal therapy is observed. Efgartigimod PH20 SC is administered at on-site visits until complete remission (CR), with a minimum of 6 weekly on-site visits after baseline. After achieving CR, efgartigimod PH20 SC is administered at on-site visits or at home by a nurse until CR on minimal therapy is achieved.

Placebo (vehicle with 2000 U/mL of rHuPH20) SC is administered using the same regimen.

CR is defined as the absence of new lesions and complete healing of established lesions (except for post-inflammatory hyperpigmentation or erythema from resolving lesions). CR on minimal therapy is defined as the absence of new lesions and complete healing of established lesions while the patient is receiving minimal prednisone therapy of ≤10 mg/day for at least 8 weeks. Randomization is stratified by disease status (experiencing flare and newly diagnosed), disease severity (PDAI activity score<30 and PDAI activity score≥30), and body weight (≤77.5 kg and >77.5 kg) at baseline. Patients with severe PV or PF (PDAI activity score≥45) will comprise a maximum of 30% of the overall trial population.

Concomitant Pemphigus Therapy

All patients, regardless of treatment assignment, concomitantly receive oral prednisone (or equivalent such as prednisolone) at a starting dose of 0.5 mg/kg qd. Except for oral prednisone (or equivalent), no other systemic therapies (e.g., immunosuppressants, IVIg, dapsone, immunoadsorption, anti-CD20 biologics) are permitted during the trial.

Patients visit the clinic weekly, until CR and for a minimum of 6 weeks, to receive efgartigimod PH20 SC and to be evaluated for disease activity and disease outcome. After CR, efgartigimod PH20 SC is administered at on-site visits or at home by a nurse until CR on minimal therapy. At any post-baseline visit before disease control (DC) is achieved, the prednisone dose is adjusted by incrementing dosage by 1 or 2 steps according to clinical judgment in case of disease progression or insufficient clinical change. Disease progression and insufficient clinical change are judged as follows:

Disease progression: increase of at least 5 in PDAI activity score compared to baseline score, observed at any post-baseline visit before DC.

Insufficient clinical change: absence of DC after 3 to 4 weeks of the patient being treated at the starting baseline prednisone (or equivalent) dose or after 3 to 4 weeks of any new incremented dose of prednisone.

The prednisone dose escalation rules based on starting dose are as follows:

Stepwise escalation of daily prednisone dose occurs in 1 or 2 steps according to clinical judgment, with a recommendation of 1 step for moderate progression and 2 steps for severe progression.

Adjustment by incrementing dosage by 1 step in case of insufficient clinical change.

Possible further escalation from the previous step by 1 or 2 steps (e.g., 0.75 mg/kg to 1 or 1.25 mg/kg qd or from 1 mg/kg to 1.25 or 1.5 mg/kg qd), according to clinical judgment and under the same recommendation as above.

Maximum escalation to 1.5 mg/kg qd for 3 weeks.

If, after a minimum of 3 weeks of oral prednisone at 1.5 mg/kg qd, DC is not attained, then the patient is considered a treatment failure.

For patients achieving DC with a daily prednisone dose of 0.5 mg/kg, prednisone is maintained at 0.5 mg/kg qd until CR and 2 weeks thereafter. For patients achieving DC with an escalated prednisone dose (i.e., >0.5 mg/kg qd), the prednisone dose is maintained until 2 weeks after achieving DC, then tapering is performed according to the following stepwise procedure: dose reductions by 0.25 mg/kg qd every 2 weeks until the starting dose is reached (i.e., 0.5 mg/kg qd). Then the starting dose (0.5 mg/kg qd) is maintained until a sustained CR is achieved for 2 weeks, or prednisone tapering may be initiated in case of sustained end of consolidation (EoC, defined by the time at which no new lesions have developed for a minimum of 2 weeks and approximately 80% of lesions have healed) for at least 4 weeks. Further tapering is performed thereafter, as long as CR or EoC are sustained. Each new tapered prednisone dose until 20 mg/day is maintained for 2 weeks. Then, the prednisone dose is further tapered by 2.5 mg/day per week. When 10 mg/day is reached, this dose level is maintained until CR on minimal therapy has been achieved. Prednisone can then be further tapered upon clinical judgment by the investigator.

In case of flare in the period between DC and CR on minimal therapy, the prednisone dose is increased. A flare is defined by the appearance of 3 or more new lesions in a 4-week period that do not heal spontaneously within 1 week, or by the extension of established lesions in a patient who had achieved DC. If the flare occurs after CR and efgartigimod PH20 SC was administered at home by a nurse, the patient will resume weekly on-site visits until he/she achieves CR again. Patients who are not controlled by a dose that is 2 dose levels above the dose at which the flare between DC and CR on minimal therapy is observed and that is at least 0.3 mg/kg/day are considered treatment failures. At visits when at least 1 new lesion is observed or established lesions remain extensive without being defined as a flare, the prednisone dose is maintained or may be increased, according to clinical judgment. If the lesion resolves, tapering of the prednisone dose is pursued as planned.

Patients who experience treatment failure, or flare after achieving CR on minimal therapy, are allowed to roll over into the OLE trial ARGX-113-1905 (Example 14) earlier than week 30. Patients who do not roll over into trial ARGX-113-1905 will complete an 8-week treatment-free follow-up period. Patients experiencing an SAE related to prednisone may also benefit from an early roll over to the OLE, according to clinical judgment.

Number of Participants:

A total of 150 patients with PV or PF are randomized as follows:

A total of 126 patients with PV are randomized in a 2:1 ratio to receive efgartigimod PH20 SC or placebo, respectively Up to 24 patients with PF may be randomized in a 2:1 ratio to receive efgartigimod PH20 SC or placebo, respectively Intervention Groups and Duration:

The maximum possible total trial duration for each patient is up to 41 weeks:

Screening period: up to 3 weeks

Treatment period: 30 weeks from baseline

Follow-up period: 8 weeks after the last dose of efgartigimod PH20 SC for patients who do not enroll in the OLE trial The trial is a prospective, multicenter, randomized, double-blinded, placebo-controlled trial to investigate the efficacy, safety, tolerability, immunogenicity, PK, and PD of efgartigimod PH20 SC in adult patients aged 18 to 80 years with moderate to severe pemphigus vulgaris (PV) or pemphigus foliaceus (PF). This trial demonstrates that efgartigimod PH20 SC with an add-on therapy of low doses of oral prednisone is a highly effective treatment modality for PV and PF, the administration of which leads to early disease remission at minimal prednisone dose.

Prednisone Tapering

Two weeks after DC is achieved after an escalated prednisone dose above 0.5 mg/kg qd, prednisone tapering begins. Prednisone tapering is a procedure that is applied by all practitioners, in order to minimize the side effects of corticosteroids while preventing a flare of the disease. In this trial:

Two-week intervals between tapering are defined with a step down of 25% from 1.5 mg to 0.5 mg/kg per day (e.g., from 1.5 to 1.25 mg/kg per day, then 1 mg/kg and 0.75 mg/kg per day). The dosage of prednisone at which CR is achieved (which cannot be lower than the starting dose 0.5 mg/kg per day) is maintained for 2 weeks after CR for observing a sustained CR, or prednisone tapering may be initiated or continued in case of sustained EoC (defined by the time at which no new lesions have developed for a minimum of 2 weeks and approximately 80% of lesions have healed) for at least 4 weeks.

When CR is observed on daily prednisone of no lower than 0.5 mg/kg for 2 weeks, or when sustained EoC is observed, tapering may be initiated. Each new tapered prednisone dose until 20 mg/day is maintained for 2 weeks. Then, the prednisone dose is further tapered by 2.5 mg/day per week. When 10 mg/day is reached, this dose level is maintained until CR on minimal therapy has been achieved.

When CR on minimal therapy is achieved, prednisone can be tapered further upon clinical judgment, with the recommendation of a prednisone decrease by 2.5 mg/day every 4 weeks.

When transient lesions appear, prednisone tapering is temporarily delayed or prednisone may be increased according to clinical judgment. Dose escalation is performed when flare occurs. Taken together, the trial aims to be as close as possible to the real-world clinical practice regarding the prednisone regimen policy, while it allows studying the potential of prednisone sparing when associated with efgartigimod PH20 SC treatment.

Proportion of Patients Who Achieve CR on Minimal Therapy within 30 Weeks as Primary Endpoint and Treatment Duration of 30 Weeks:

A trial duration of 30 weeks was selected based on results from the phase 2 trial ARGX-113-1701 in patients with pemphigus for encompassing the observation of the primary endpoint of CR on minimal therapy in the majority of patients belonging to the active group. The time point at which CR on minimal therapy is anticipated to be achieved for most patients varies between 24 and 30 weeks in patients under active treatment and depends on the body weight of the patients. Accounting for this variation between patients, all patients having achieved CR on minimal therapy within the 30 weeks of the trial are considered as responsive to treatment in the primary endpoint.

Tailored Regimen of Efgartigimod PH20 SC and Rollover to the OLE:

The trial comprises a screening period of up to 3 weeks, a treatment period until CR on minimal therapy of 30 weeks, and an 8-week follow-up period for patients who do not enroll into the OLE trial ARGX-113-1905 (Example 14). A tailored efgartigimod PH20 SC regimen is proposed due to its rapid effect and the variability of disease activity between patients. Patients are administered the efgartigimod PH20 SC with concomitant low dose prednisone regimen subcutaneously until CR on minimal therapy is achieved. Then, efgartigimod PH20 SC administration is stopped, whereas the concomitant treatment by prednisone is pursued with the option for further tapering to achieve CR off therapy.

Inclusion Criteria

Participants are eligible to be included in the trial only if all of the following criteria apply:

Ability to understand the requirements of the trial, to provide written informed consent (including consent for the use and disclosure of research-related health information), willingness and ability to comply with the trial protocol procedures (including required trial visits).

The patient is male or female, and aged 18 years to 80 years at the time of signing the informed consent form (ICF).

The patient has a clinical diagnosis of PV (mucosal, cutaneous, mucocutaneous) or PF which has been confirmed by cutaneous histology, positive direct immunofluorescence (IF), and positive indirect IF and/or ELISA.

The patient meets 1 of the following profiles:

Newly diagnosed disease with PDAI activity score≥15 at baseline and naïve to treatment.

Newly diagnosed disease with PDAI activity score≥15 while receiving a first course of oral prednisone (or equivalent). According to clinical judgment, the patient has shown no significant improvement of PV or PF signs for at least 2 weeks before baseline and is considered fit to start prednisone treatment at 0.5 mg/kg qd at baseline.

Experiencing flare with PDAI activity score≥15, a maximum of 4 years since diagnosis, and off prednisone therapy±a conventional immunosuppressant (eg, azathioprine, cyclophosphamide, methotrexate, mycophenolate mofetil). Conventional immunosuppressants are discontinued before baseline.

Experiencing flare with PDAI activity score≥15, a maximum of 4 years since diagnosis, and receiving a tapered dose of oral prednisone (or equivalent), provided that prednisone has been given at stable dose±a conventional immunosuppressant (e.g., azathioprine, cyclophosphamide, methotrexate, mycophenolate mofetil) for at least 2 weeks and patients are fit to start prednisone treatment at 0.5 mg/kg qd at baseline. Conventional immunosuppressants are discontinued before baseline.

Exclusion Criteria

Participants are excluded from the trial if any of the following criteria apply:

Patient has a confirmed diagnosis of paraneoplastic pemphigus, drug-induced pemphigus, pemphigus vegetans, pemphigus erythematosus, or any other non-PV/non-PF autoimmune blistering disease.

Patients with mild disease severity as defined by PDAI activity score<15 at baseline.

Patients who show a significant improvement of PV or PF in the period from screening to baseline according to clinical judgment (e.g., the patient has achieved DC or a substantial reduction in PDAI activity score during screening period).

The patient has been administered therapy (ies) other than oral prednisone or conventional immunosuppressants (e.g., azathioprine, cyclophosphamide, methotrexate, mycophenolate mofetil) within 2 months before the baseline visit and that can affect clinical disease activity. For example, excluded medications are intravenous methylprednisolone, dapsone, sulfasalazine, tetracyclines, nicotinamide, plasmapheresis/plasma exchange, immunoadsorption, and IVIg.

Use of any monoclonal antibody (including rituximab or another anti-CD20 biologic) within 6 months before the baseline visit.

Known hypersensitivity to any of the components of the administered treatments.

The patient has a known contraindication to oral prednisone.

The patient has a history of refractory disease, as defined by a failure to respond to first-line and second-line therapies.

Trial Intervention(s) Administered

A list of trial interventions is presented in Table 11. Fixed doses of efgartigimod PH20 SC are administered on body sites spared of any cutaneous pemphigus lesions, the abdomen being used as preferred site. If the abdomen is affected by lesions, optional sites (thighs and the arms) may be chosen. The placebo solution for injection contains the same excipients as the efgartigimod PH20 SC solution for injection but without efgartigimod. Masked vials are provided to preserve the study blind. Additionally, patients receive oral prednisone (or equivalent such as prednisolone) as concomitant therapy.

TABLE 11

Trial Interventions-ARGX-113-1904

| Intervention | Efgartigimod PH20 SC | Placebo | Prednisone (or Equivalent) |
|---|---|---|---|
| Type | Biologic | Other: placebo | Non-IMP |
| Dose formulation | Efgartigimod 165 mg/mL + 2000 U/mL rHuPH20 solution for SC injection to be dosed at a fixed dose of 1000 mg per injection | Vehicle + rHuPH20 for SC administration | Prednisone/prednisolone tablets for oral administration |
| Unit dose strength(s) | 165 mg/mL | Placebo | Prednisone 5 mg, 10 mg, 20 mg, 50 mg Prednisolone 5 mg |
| Dosage level(s) | 2 × 1000 mg administered in separate sites on day 1 and day 8 followed by weekly 1000 mg administrations until CR on minimal therapy | 2 × SC administrations in separate sites on day 1 and day 8 followed by weekly single administrations until CR on minimal therapy | Refer to Concomitant Pemphigus Therapy |
| Route of administration | Abdominal SC injection(s); preferred site[a] | Abdominal SC injection(s); preferred site[a] | Oral administration |
| Sourcing | Provided by the sponsor to the trial site | Provided by the sponsor to the trial site | Provided by the sponsor to the trial site, or provided locally |
| Packaging and Labeling | The IMP is provided in glass vials. Each glass vial is labeled as required per country requirement | The IMP is provided in glass vials. Each glass vial is labeled as required per country requirement | Non-IMP is provided in the commercial package, or as magistral preparation upon prescription by the investigator |

IMP = investigational medicinal product; SC = subcutaneous(ly)
[a]IMP is administered on body sites spared of any cutaneous pemphigus lesions, the abdomen being used as preferred site. If the abdomen is affected by lesions, optional sites (thighs or arms) may be chosen.

End of Study (EoS)/Early Termination (ET)

All patients complete week 30/EoS/ET, which is end of study for patients who enroll in the OLE trial ARGX-113-1905.

Treatment-Free Follow-Up Period

Patients who reach week 30, discontinue early, or patients under treatment failure, and who do not roll over to the OLE trial, enter the 8-week treatment-free follow-up period.

Efficacy Assessments

The efficacy of efgartigimod PH20 SC is assessed at on-site visits by the investigator, assessing the following: PDAI, DC, EoC, CR, CR on minimal therapy, CR off therapy, and flare. The investigator records the daily prednisone dose since the last visit, and treatment failures at on-site visits. For home visits, the investigator calls the patient at least every 2 weeks until CR on minimal therapy is achieved to confirm the patient is still in CR.

The clinical activity of pemphigus is assessed using the PDAI.

Example 14: Open Label Phase 3 Extension Clinical Trial with Subcutaneous Administration—ARGX-113-1905

ARGX-113-1905 is an open-label, long-term extension (OLE) follow-up study, evaluating the safety, tolerability, and efficacy of efgartigimod PH20 SC in adult patients with PV or PF. Trial ARGX-113-1905 provides efgartigimod PH20 SC extended treatment and retreatment options for patients who were randomized to the efgartigimod PH20 SC treatment arm in trial ARGX-113-1904 (Example 13), and provides first efgartigimod PH20 SC treatment and retreatment options for patients who were randomized to the placebo treatment arm in trial ARGX-113-1904. The trial is given the acronym ADDRESS+.

At blinded rollover from trial ARGX-113-1904 into trial ARGX-113-1905 patients may be in different clinical stages. Patients may have achieved CR on minimal therapy, patients may have achieved CR without meeting the minimal therapy criterion, patients may have achieved DC or EoC (the time at which no new lesions have developed for a minimum of 2 weeks and approximately 80% of lesions have healed) without having achieved CR, patients may have experienced treatment failure, or patients may have experienced a flare after having achieved CR on minimal therapy.

Trial ARGX-113-1905 evaluates the ability to (further) taper prednisone therapy and achieve CR off therapy, the ability to achieve CR and CR on minimal therapy for patients who had not yet achieved CR on minimal therapy, and the ability to treat flare; and assesses patient outcome measures and the safety, PD, PK, and immunogenicity of efgartigimod PH20 SC over the duration of the trial.

Overall Design

This is a prospective, multicenter, OLE trial on the efficacy, safety, tolerability, immunogenicity, PK, and PD of efgartigimod PH20 SC in adult PV or PF patients, who participated in the antecedent trial ARGX-113-1904. See FIG. 14 for a diagram of the trial design.

Patients at the EoS visit or early termination visit in trial ARGX-113-1904 are given the option to enroll into trial ARGX-113-1905 after confirmation of eligibility while retaining the blinding of trial ARGX-113-1904. For each patient, the date of the baseline visit in trial ARGX-113-1905 is the same as the date of the EoS visit in trial ARGX-113-1904.

Concomitant Pemphigus Therapy

At baseline, patients are treated according to their clinical status at EoS of trial ARGX-113-1904, as follows:

Patients in CR on minimal or off therapy are observed every 4 weeks through on-site visits without efgartigimod PH20 SC treatment. In patients who have achieved CR on minimal therapy (oral prednisone≤10 mg per day for 8 weeks), prednisone tapering may be pursued upon investigator's judgment until patients achieve CR off therapy.

Patients who have achieved CR but not CR on minimal therapy receive weekly efgartigimod PH20 SC administrations of 1000 mg while continuing the add-on therapy of oral prednisone until CR on minimal therapy is achieved. Prednisone tapering may be pursued upon investigator's judgment until patients achieve CR off therapy. Patients are treated through on-site visits, or through home visits with an on-site visit once every 4 weeks.

Patients who have achieved DC but not CR receive weekly on-site administrations of 1000 mg efgartigimod PH20 SC with an add-on therapy of oral prednisone until CR has been achieved, and then continue to receive weekly efgartigimod PH20 SC administrations of 1000 mg until CR on minimal therapy is achieved either on site, or through home visits with an on-site visit once every 4 weeks.

Patients under certain conditions of treatment failure as defined in trial ARGX-113-1904 (i.e., absence of DC with oral prednisone 1.5 mg/kg/day for a minimum of 3 weeks, or flare between DC and achieving CR on minimal therapy that is not controlled by 2 dose levels above the dose at which the flare is observed and that is at least 0.3 mg/kg/day), or patients with flare after having achieved CR on minimal therapy, may rollover prematurely into trial ARGX-113-1905 and are treated with efgartigimod PH20 SC at a dose of 2000 mg on day 1 and day 8, followed by weekly administrations of 1000 mg with an add-on therapy of oral prednisone until CR on minimal therapy. In the absence of DC, patients receive prednisone at the starting dose of 0.5 mg/kg/day. In case of flare, patients receive as starting dose the last dose from ARGX-113-1904, with the recommendation of a minimum of 0.3 mg/kg/day when the flare is of mild severity (PDAI activity score<15) and of 0.5 mg/kg/day when the flare is moderate to severe (PDAI activity score≥15). Dosing of efgartigimod PH20 SC is done during on-site visits or home visits.

Patients who developed a prednisone-related SAE may prematurely rollover into trial ARGX-113-1905 and may be treated with efgartigimod PH20 SC through on-site or home visits according to the clinical statuses as described above. Concomitant prednisone is considered to fit the clinical statuses as described above as far as compatible with the nature and severity of the SAE, with a lower dose to no concomitant prednisone being considered otherwise.

At any post-baseline visit before DC is achieved, the prednisone dose is adjusted by incrementing dosage by 1 or 2 steps according to clinical judgment in case of disease progression or insufficient clinical change. Disease progression and insufficient clinical change is defined as follows:

Disease progression: increase of at least 5 in PDAI activity score compared to baseline score, observed at any post-baseline visit before DC Insufficient clinical change: the absence of DC after 3 to 4 weeks of the patient being treated at the starting baseline prednisone dose or after 3 to 4 weeks of any new incremented dose of prednisone The prednisone dose escalation rules based on starting dose are as follows:

Stepwise escalation of daily prednisone dose occurs in 1 or 2 steps according to clinical judgment, with a recommendation of 1 step for moderate progression and 2 steps for severe progression Adjustment by incrementing dosage by 1 step in case of insufficient clinical change Possible further escalation from the previous step by 1 or 2 steps (e.g., 0.75 mg/kg to 1 or 1.25 mg/kg qd, or from 1 mg/kg to 1.25 or 1.5 mg/kg qd), according to clinical judgment and under the same recommendation as above Maximum escalation to 1.5 mg/kg qd for 3 weeks If DC is not attained after a minimum of 3 weeks of the patient receiving oral prednisone 1.5 mg/kg qd, then the patient is considered a treatment failure and is withdrawn from the trial.

For patients who achieve DC with the daily starting dose at baseline, the prednisone dose is maintained at that starting dose qd until CR and for the next 2 weeks. For patients who achieve DC with an escalated prednisone dose, that dose is maintained until 2 weeks after achieving DC and then is tapered in 25% reductions every 2 weeks until the starting dose has been achieved. This starting dose is maintained until a sustained CR is achieved for 2 weeks, or in case of end of consolidation (EoC) for 4 weeks. Further tapering is performed thereafter, as long as CR or EoC is sustained. Each new tapered prednisone dose until 20 mg/day is maintained for 2 weeks. Then, the prednisone dose is further tapered by 2.5 mg/day per week. When 10 mg/day is reached, this dose level is maintained until CR on minimal therapy has been achieved. The prednisone dose can then be further tapered to reach CR off therapy according to the clinical judgment of the investigator.

Number of Participants:

All participants who were randomized into ARGX-113-1904 (i.e., up to 150 patients with pemphigus vulgaris (PV) or pemphigus foliaceus (PF)) are eligible to rollover to trial ARGX-113-1905

Intervention Groups and Duration:

Up to 60 weeks for patients who receive efgartigimod PH20 SC administrations up to week 52 and with a follow-up period of 8 weeks after the last efgartigimod PH20 SC administration.

At visits when at least 1 new lesion is observed or established lesions remain extensive without being defined as a flare (i.e., the appearance of 3 or more new lesions in a 4-week period that do not heal spontaneously within 1 week, or by the extension of established lesions in a patient who had achieved DC), the prednisone dose is maintained or may be increased, according to clinical judgment. If the lesion resolves, tapering of the prednisone dose is pursued as planned.

In case of flare in the period between DC and CR on minimal therapy, the prednisone dose is increased to achieve DC again. If the flare occurs after CR and IMP was administered at home by a nurse, the patient will resume weekly on-site visits until he/she achieves CR again. Patients who are not controlled by a dose that is 2 dose levels above the dose at which the flare is observed and that is at least 0.3 mg/kg/day, are managed according to clinical judgment, i.e., either receive a further increased prednisone dose or be withdrawn from the trial. Withdrawal of patients with a flare before CR on minimal therapy is defined as treatment failure.

In case of flare after having achieved CR on minimal therapy (i.e., while being off efgartigimod treatment), patients are immediately treated/re-treated with a new cycle of efgartigimod PH20 SC. The first day of new efgartigimod treatment will define a new baseline for assessments of outcomes (DC, CR, etc) and prednisone escalation or tapering schedule.

In the new treatment cycle, patients are administered efgartigimod PH20 SC at a weekly dose of 2000 mg for the first 2 weeks, followed by weekly administrations of 1000 mg until CR on minimal therapy. Oral prednisone is administered at a dose chosen according to clinical judgment, with the recommendation of 0.3 mg/kg qd in the case of mild flare (PDAI activity score<15) and 0.5 mg/kg qd in the case of moderate to severe flare (PDAI activity score≥15). The treatment goal of a new treatment cycle is to first achieve DC again and therefore these patients are treated accordingly.

A new treatment cycle of efgartigimod PH20 SC can be initiated in eligible patients until week 44. In patients requiring a new treatment cycle of efgartigimod PH20 SC between weeks 45 and 49, the initiation is optional and based on clinical judgment and patient consent. A new efgartigimod treatment cycle will not be permitted after week 49 to ensure a minimum of 4 weeks of efgartigimod treatment/cycle.

Except for oral prednisone, no other systemic therapies (e.g., immunosuppressants, IVIg, dapsone, immunoadsorption, anti-CD20 biologics) are permitted during the trial.

SC administration is highly preferred over an IV formulation for pemphigus patients in view of the expected need for prolonged weekly administration. Therefore, efgartigimod with rHuPH20 is administered SC weekly until CR on minimal therapy; retreatment may be initiated in case of flare after having achieved CR on minimal therapy. To achieve a fast PD effect and clinical response a dose of 2000 mg is administered in the first 2 weeks, followed by weekly doses of 1000 mg to maintain the PD effect and related clinical response.

Trial Interventions Administered

A list of trial interventions is presented in Table 12. Fixed doses of efgartigimod PH20 SC are administered on body sites spared of any cutaneous pemphigus lesions, the abdomen being used as preferred site. If the abdomen is affected by lesions, optional sites (the thighs and the arms) may be chosen.

TABLE 12

| Trial Interventions-ARGX-113-1905 | | |
|---|---|---|
| Intervention | Efgartigimod PH20 SC | Prednisone (or Equivalent) |
| Type | Biologic | Non-IMP |
| Dose formulation | Efgartigimod 165 mg/mL + 2000 U/mLrHuPH20 solution for SC injection to be dosed at a fixed dose of 1000 mg per injection | Prednisone/prednisolone tablets for oral administration |
| Unit dose strength(s) | 165 mg/mL | Prednisone 5 mg, 10 mg, 20 mg, 50 mg Prednisolone 5 mg |
| Dosage level(s) | Weekly 1000 mg administrations until CR on minimal therapy, for patients in DC or CR at rollover from ARGX-113-1904. 2 × 1000 mg administered in separate sites on day 1 and day 8 followed by weekly 1000 mg administrations until CR on minimal therapy, for patients under treatment failure in ARGX-113-1904, or patients experiencing flare after CR on minimal therapy. | Refer to Concomitant Pemphigus Therapy |
| Route of administration | Abdominal SC injection(s); preferred site[a] | Oral administration |
| Use | Investigational drug | Non-IMP or concomitant therapy |
| IMP | IMP | Non-IMP |
| Sourcing | Provided by the sponsor to the trial site[a] | Provided by the sponsor to the trial site, or provided locally |
| Packaging and labeling | The IMP is provided in glass vials. Each glass vial is labeled as required per country requirement | Non-IMP is provided in the commercial package, or as magistral preparation upon prescription by the investigator |

CR = complete clinical remission; CR on minimal therapy = complete remission on minimal therapy; DC = disease control; IMP = investigational medicinal product; SC-subcutaneous.
[a]IMP is administered on body sites spared of any cutaneous pemphigus lesions, the abdomen being used as preferred site. If the abdomen is affected by lesions, optional sites (thighs or arms) may be chosen.

The efficacy of efgartigimod PH20 SC is assessed at on-site and home visits by the investigator, assessing by chronological order the following: PDAI, DC, EoC, CR, CR on minimal therapy, CR off therapy, and flare. The investigator records the average daily prednisone dose since the last visit, and treatment failures at on-site visits. For home visits, the investigator calls the patient every 2 weeks until CR on minimal therapy to confirm the patient is still in CR and to determine the prednisone tapering schedule.

Additionally, the clinical activity of pemphigus is assessed using the PDAI.

Efficacy Endpoints
  Proportion of patients who achieve CR on minimal therapy in patients with PV.
  Proportion of patients who achieve CR on minimal prednisone dose in patients with PV and PF Time to DC.
Time to complete clinical remission (CR)
Time to CR on minimal therapy.
Time to CR off therapy.
Time to flare.
Rate of treatment failure
Rate of flare
Cumulative prednisone dose over the trial
PDAI at each visit Pharmacokinetics.
    Efgartigimod serum concentrations
Pharmacodynamics.
    Total IgG and subtype (IgG1, IgG2, IgG3, IgG4) serum levels.
    Anti-Dsg-1 and -3 autoantibody serum levels
Immunogenicity
    ADAs to efgartigimod PH20 SC (both to efgartigimod and to rHuPH20)

We claim:

1. A method of treating pemphigus, comprising administering to a subject in need thereof an effective amount of a human neonatal Fc receptor (FcRn) antagonist, wherein the FcRn antagonist is efgartigimod, thereby treating pemphigus in the subject, wherein the subject has mild, moderate, or severe pemphigus as classified by the Pemphigus Disease Area Index (PDAI).

2. The method of claim 1, whereby disease control or complete remission is achieved.

3. The method of claim 1, wherein the pemphigus comprises pemphigus vulgaris (PV), pemphigus foliaceus (PF), or both PV and PF.

4. The method of claim 1, wherein the FcRn antagonist is administered once weekly or every two weeks until disease control or complete remission is achieved.

5. The method of claim 1, wherein the FcRn antagonist is administered intravenously at a dose of 10 mg/kg to 30 mg/kg once weekly or every two weeks.

6. The method of claim 1, wherein the FcRn antagonist is administered subcutaneously at a fixed dose of 750 mg to 3000 mg once weekly or every two weeks.

7. The method of claim 1, further comprising administering to the subject a corticosteroid at a dose of <0.5 mg prednisone/kg/day or equivalent.

8. The method of claim 1, wherein the FcRn antagonist is administered in an induction phase and a consolidation phase, wherein
   (i) during the induction phase the FcRn antagonist is administered once weekly or biweekly and a corticosteroid is administered at a dose of <0.5 mg prednisone/kg/day or equivalent until disease control, and
   (ii) during the consolidation phase the FcRn antagonist dose is reduced or the FcRn antagonist dosing interval is lengthened, and/or the corticosteroid dose is decreased or the corticosteroid dosing interval is lengthened, to an end-of-consolidation dose or dosing interval effective to prevent new lesions from appearing.

9. The method of claim 8, further comprising a maintenance phase, wherein
   (iii) during the maintenance phase the end-of-consolidation dose or dosing interval for the FcRn antagonist and/or the prednisone or equivalent is continued until complete clearance of lesions.

10. The method of claim 8, wherein during the induction phase the FcRn antagonist is administered intravenously at a dose of 10 mg/kg to 30 mg/kg.

11. The method of claim 8, wherein during the induction phase the FcRn antagonist is administered subcutaneously at a fixed dose of 750 mg to 3000 mg.

12. The method of claim 1, wherein the subject has refractory pemphigus.

13. The method of claim 1, wherein the subject has newly diagnosed pemphigus vulgaris, with a Pemphigus Disease Area Index (PDAI) score of ≥15.

14. The method of claim 1, wherein the subject has relapsing pemphigus vulgaris.

15. The method of claim 1, wherein the subject is corticosteroid-intolerant.

16. The method of claim 1, wherein the FcRn antagonist is administered intravenously at a dose of 10 mg/kg once weekly or every two weeks.

17. The method of claim 1, wherein the FcRn antagonist is administered intravenously at a dose of 25 mg/kg once weekly or every two weeks.

18. The method of claim 1, wherein the FcRn antagonist is administered subcutaneously at a fixed dose of 1000 mg or 2000 mg once weekly or every two weeks.

19. The method of claim 1, wherein disease control or complete remission is achieved without administration of a corticosteroid to the subject.

20. The method of claim 19, wherein disease control is achieved within 1 to 4 weeks of first administration of the FcRn antagonist.

21. The method of claim 19, wherein disease control is achieved within 15 days of first administration of the FcRn antagonist.

* * * * *

SEQUENCE LISTING

```
<160> NUMBER OF SEQ ID NOS: 7

<210> SEQ ID NO 1
<211> LENGTH: 226
<212> TYPE: PRT
<213> ORGANISM: Artificial sequence
<220> FEATURE:
<223> OTHER INFORMATION: Synthetic polypeptide

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly
225

<210> SEQ ID NO 2
<211> LENGTH: 227
<212> TYPE: PRT
<213> ORGANISM: Artificial sequence
<220> FEATURE:
<223> OTHER INFORMATION: Synthetic polypeptide

<400> SEQUENCE: 2
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu Lys Phe His Tyr Thr Gln Lys Ser Leu Ser Leu Ser
    210                 215                 220

Pro Gly Lys
225

<210> SEQ ID NO 3
<211> LENGTH: 221
<212> TYPE: PRT
<213> ORGANISM: Artificial sequence
<220> FEATURE:
<223> OTHER INFORMATION: Synthetic polypeptide

<400> SEQUENCE: 3

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Tyr Ile Thr Arg Glu Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125
```

-continued

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu Lys
                195                 200                 205

Phe His Tyr Thr Gln Lys Ser Leu Ser Leu Ser Pro Gly
    210                 215                 220

<210> SEQ ID NO 4
<211> LENGTH: 216
<212> TYPE: PRT
<213> ORGANISM: Artificial sequence
<220> FEATURE:
<223> OTHER INFORMATION: Synthetic polypeptide

<400> SEQUENCE: 4

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 5
<211> LENGTH: 445
<212> TYPE: PRT
<213> ORGANISM: Artificial sequence
<220> FEATURE:
<223> OTHER INFORMATION: Synthetic polypeptide

<400> SEQUENCE: 5

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
            85                  90                  95

Ala Arg Leu Ala Ile Gly Asp Ser Tyr Trp Gly Gln Gly Thr Met Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
    435                 440                 445

<210> SEQ ID NO 6
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65              70                  75                  80

Ser Ser Leu Gln Pro Glu Asp Phe Ala Thr Tyr Tyr Cys Leu Gln Gly
            85                  90                  95

Thr His Phe Pro His Thr Phe Gly Gln Gly Thr Lys Leu Glu Ile Lys
        100                 105                 110

Arg Thr Val Ala Ala Pro Ser Val Phe Ile Phe Pro Pro Ser Asp Glu
    115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 7
<211> LENGTH: 444
<212> TYPE: PRT
<213> ORGANISM: Artificial sequence
<220> FEATURE:
<223> OTHER INFORMATION: Synthetic polypeptide

<400> SEQUENCE: 7

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

```
Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Val Tyr Tyr Cys
                 85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```